US012788798B2

(12) United States Patent
Katsimpardi et al.

(10) Patent No.: US 12,788,798 B2
(45) Date of Patent: Nov. 10, 2026

(54) USE OF GDF11 TO DIAGNOSE AND TREAT ANXIETY AND DEPRESSION

(71) Applicants: INSTITUT PASTEUR, Paris (FR); MCMASTER UNIVERSITY, Hamilton (CA)

(72) Inventors: Lida Katsimpardi, Paris (FR); Pierre-Marie Lledo, Paris (FR); Bianca Wollenhaupt De Aguiar, Brantford (CA); Taiane De Azevedo Cardoso, Hamilton (CA); Flavio Kapczinski, Hamilton (CA); Bianca Pfaffenseller, Hamilton (CA)

(73) Assignees: INSTITUT PASTEUR, Paris (FR); MCMASTER UNIVERSITY, Hamilton (CA)

(*) Notice: Subject to any disclaimer, the term of this patent is extended or adjusted under 35 U.S.C. 154(b) by 836 days.

(21) Appl. No.: 18/004,801

(22) PCT Filed: Jul. 9, 2021

(86) PCT No.: PCT/IB2021/000495
§ 371 (c)(1),
(2) Date: Jan. 9, 2023

(87) PCT Pub. No.: WO2022/008976
PCT Pub. Date: Jan. 13, 2022

(65) Prior Publication Data

US 2023/0241171 A1 Aug. 3, 2023

Related U.S. Application Data

(60) Provisional application No. 63/050,421, filed on Jul. 10, 2020.

(51) Int. Cl.

| | |
|---|---|
| ***A61K 38/18*** | (2006.01) |
| ***A61P 25/24*** | (2006.01) |
| ***C07K 16/22*** | (2006.01) |
| ***G01N 33/68*** | (2006.01) |

(52) U.S. Cl.
CPC .......... *A61K 38/1841* (2013.01); *A61P 25/24* (2018.01); *C07K 16/22* (2013.01); *G01N 33/6896* (2013.01); *G01N 2800/304* (2013.01)

(58) Field of Classification Search
None
See application file for complete search history.

(56) References Cited

U.S. PATENT DOCUMENTS

2021/0101951 A1* 4/2021 Wagers .................. C07K 14/51

FOREIGN PATENT DOCUMENTS

| | | | |
|---|---|---|---|
| JP | 2018132526 | * | 8/2018 |
| JP | 2018132526 | A | 8/2018 |
| WO | 2019144053 | A1 | 7/2019 |

OTHER PUBLICATIONS

Katsimpardi et al. Systemic GDF11 stimulates the secretion of adiponectin and induces a calorie restriction-like phenotype in aged mice. Aging Cell, 2020, e13038, 1-11.
Katsimpardi et al. Vascular and neurogenic rejuvenation of the aging mouse brain by young systemic factors. Science, 2014, 344, 630-634.
Ozek, et al. Growth Differentiation Factor 11 treatment leads to neuronal and vascular improvements in the hippocampus of aged mice. Sci Rep, 2018, 8, 17293, 1-13.
Leger et al. Object recognition test in mice. Nat Protocols, 2013, 8, 2531-2537.
Santarelli, et al. Requirement of hippocampal neurogenesis for the behavioral effects of antidepressants. Science, 2003, 301, 805-809.
Dong et al. Autophagy involving age-related cognitive behavior and hippocampus injury is modulated by different caloric intake in mice. Int J Clin Exp Med, 2015, 8(7), 11843-11853.
Chinta et al. Cellular senescence and the aging brain. Exp Gerontol, 2015, 68, 3-7.
Jurk, D. et al. Postmitotic neurons develop a p21-dependent senescence-like phenotype driven by a DNA damage response. Aging Cell, 2012, 11, 996-1004.
Krishnamurthy et al. Ink4a/Arf expression is a biomarker of aging. J Clin Invest, 2004, 114(9), 1299-1307.
Chesney et al. Risks of all-cause and suicide mortality in mental disorders: A meta-review. World Psychiatry, (2014), 13(2), 153-160.
Du et al. A Novel and Convenient Method for the Preparation and Activation of PRP without Any Additives: Temperature Controlled PRP. Biomed Res Int. 2018, 1761865, 1-13.
Fries et al. Accelerated aging in bipolar disorder: A comprehensive review of molecular findings and their clinical implications. Neurosci Biobehav Rev. 2020, 112, 107-116.
Katsimpardi and Rubin. Young systemic factors as a medicine for age-related neurodegenerative diseases. Neurogenesis, 2015, 2(1), e1004971-23-e1004971-27.
Li et al. Camelid single-domain antibodies: A versatile tool for in vivo imaging of extracellular and intracellular brain targets. J Control Release. 2016, 243, 1-10.

(Continued)

*Primary Examiner* — Daniel C Gamett
(74) *Attorney, Agent, or Firm* — Arrigo, Lee, Guttman & Mouta-Bellum LLP

(57) ABSTRACT

Provided are methods for the detection of GDF11 in a subject having or suspected of having a mood and/or anxiety disorder, comprising providing a sample from a subject having or suspected of having a mood and/or anxiety disorder; contacting the sample with a GDF11-binding molecule; and detecting bound GDF11. Also provided are methods of diagnosing or characterizing a mood and/or anxiety disorder in a subject, comprising providing a sample from a subject; contacting the sample with a GDF11-binding molecule; detecting bound GDF11; and comparing the levels of detected bound GDF11 to healthy reference levels. Also provided are methods of treating or preventing a mood and/or anxiety disorder and/or accelerated aging in a subject in need thereof, comprising administering to the subject an agent or composition which increases the levels of GDF11 polypeptide in the subject.

10 Claims, 24 Drawing Sheets

Specification includes a Sequence Listing.

(56) References Cited

OTHER PUBLICATIONS

Lopez-Villareal et al. Progression of the functional deficit in a group of patients with bipolar disorder: a cluster analysis based on longitudinal data. Eur Arch Psychiatry Clin Neurosci, 2020, 270, 947-957.

Dattani el al. Mental health. Retrieved May 6, 2021, https://ourworldindata.org/mental-health.

Squassina et al. Mood Disorders, Accelerated Aging, and Inflammation: Is the Link Hidden in Telomeres? Cells. 2019, 8(1), 52, 1-15.

Walker et al. Mortality in mental disorders and global disease burden implications. JAMA Psychiatry, 2015, 72(4), 334-341.

Alting-Mees et al., Monoclonal Antibody Expression Libraries: A Rapid Alternative to Hybridomas, Strategies in Molecular Biology, 1990, 3(1), 1-9.

Souza et al., Proteomic identification and functional validation of activins and bone morphogenetic protein 11 as candidate novel muscle mass regulators. Molecular Endocrinology, 2008, 22(12), 2689-2702.

Holliger and Hudson, Engineered antibody fragments and the rise of single domains. Nature Biotechnology, 2005, 23(9), 126-136.

Carter. Potent antibody therapeutics by design, Nature Reviews Immunology, 2006, 6, 343-357.

Moreira et al., Biological rhythms, metabolic syndrome and current depressive episode in a community sample. Psychoneuroendocrinology, 2016, 72, 34-39.

David et al., Neurogenesis-dependent and -independent effects of fluoxetine in an animal model of anxiety/depression. Neuron, 2009, 62, 479-493.

Hudobenko et al. Growth differentiation factor-11 supplementation improves survival and promotes recovery after ischemic stroke in aged mice, Aging, 2020, 12(9), 1-18.

* cited by examiner e

Clinical parameters

| Variables | Controls n=51 | MDD n=57 | p-value |
|---|---|---|---|
| **Gender** | | | 0.968 |
| Women | 41 (80.4%) | 46 (80.7%) | |
| Men | 10 (19.6%) | 11 (19.3%) | |
| **Age** | 25.94 +/- 5.84 | 26.14 +/- 2.34 | 0.851 |
| **Years of education** | 10.98 +/- 3.08 | 10.35 +/- 3.65 | 0.338 |
| **MADRS score** | 0.00 (0.00; 2.00) | 14.00 (10.00; 21.00) | <0.001 |

Figure 1 (continuation)
f
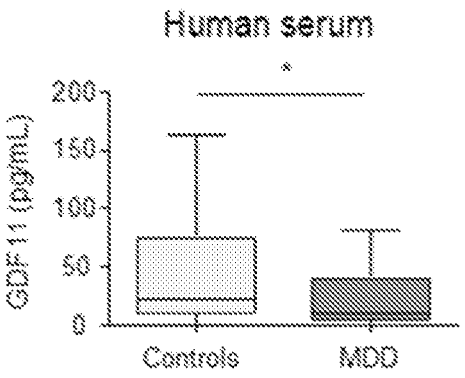
Figure 2
a
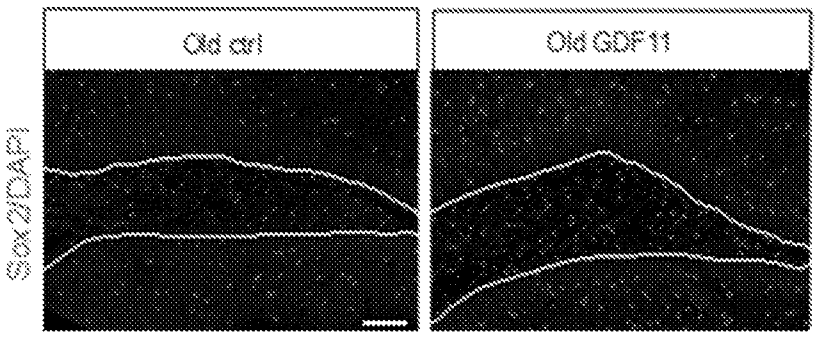

Figure 2 (continuation)
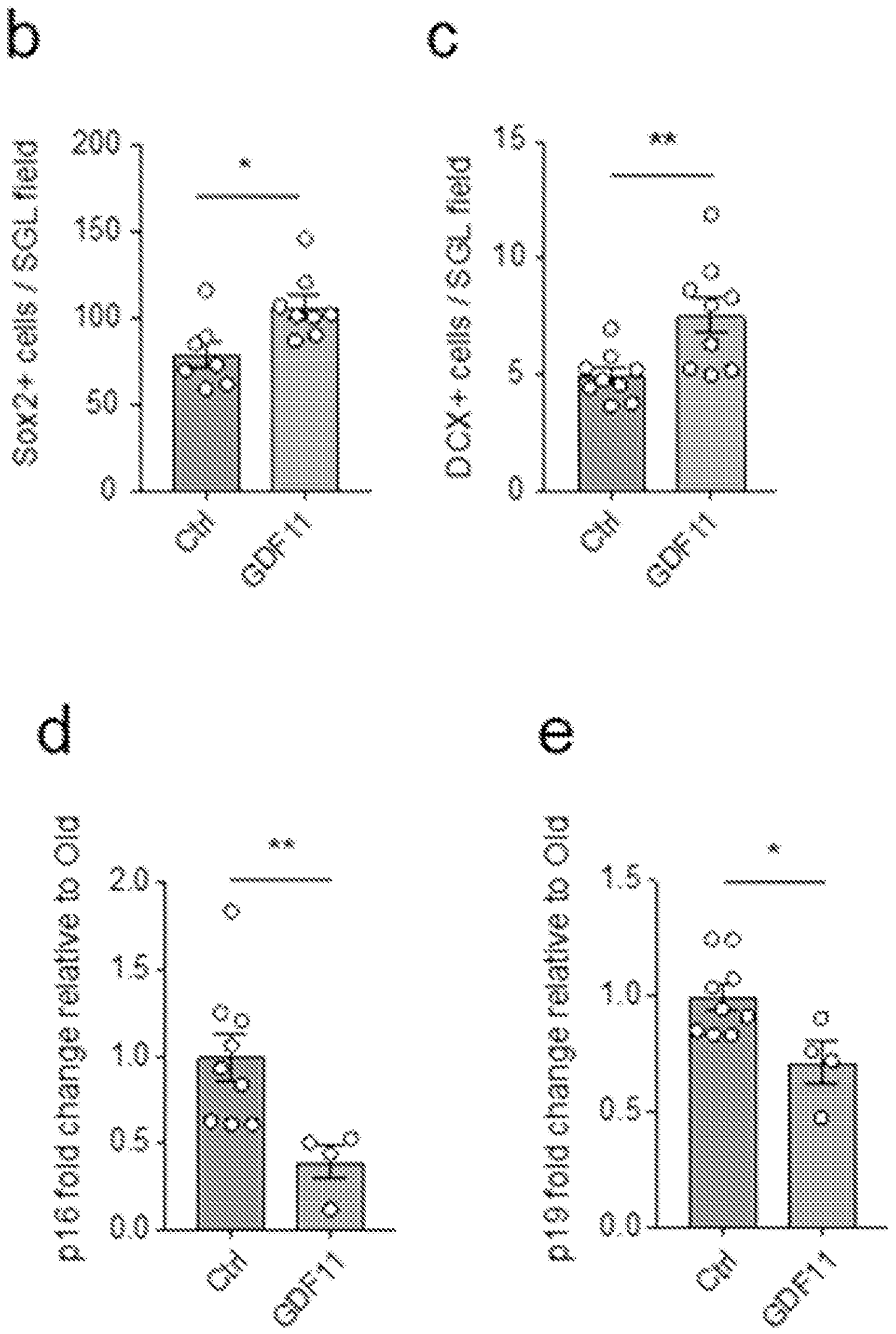

Figure 2 (continuation)
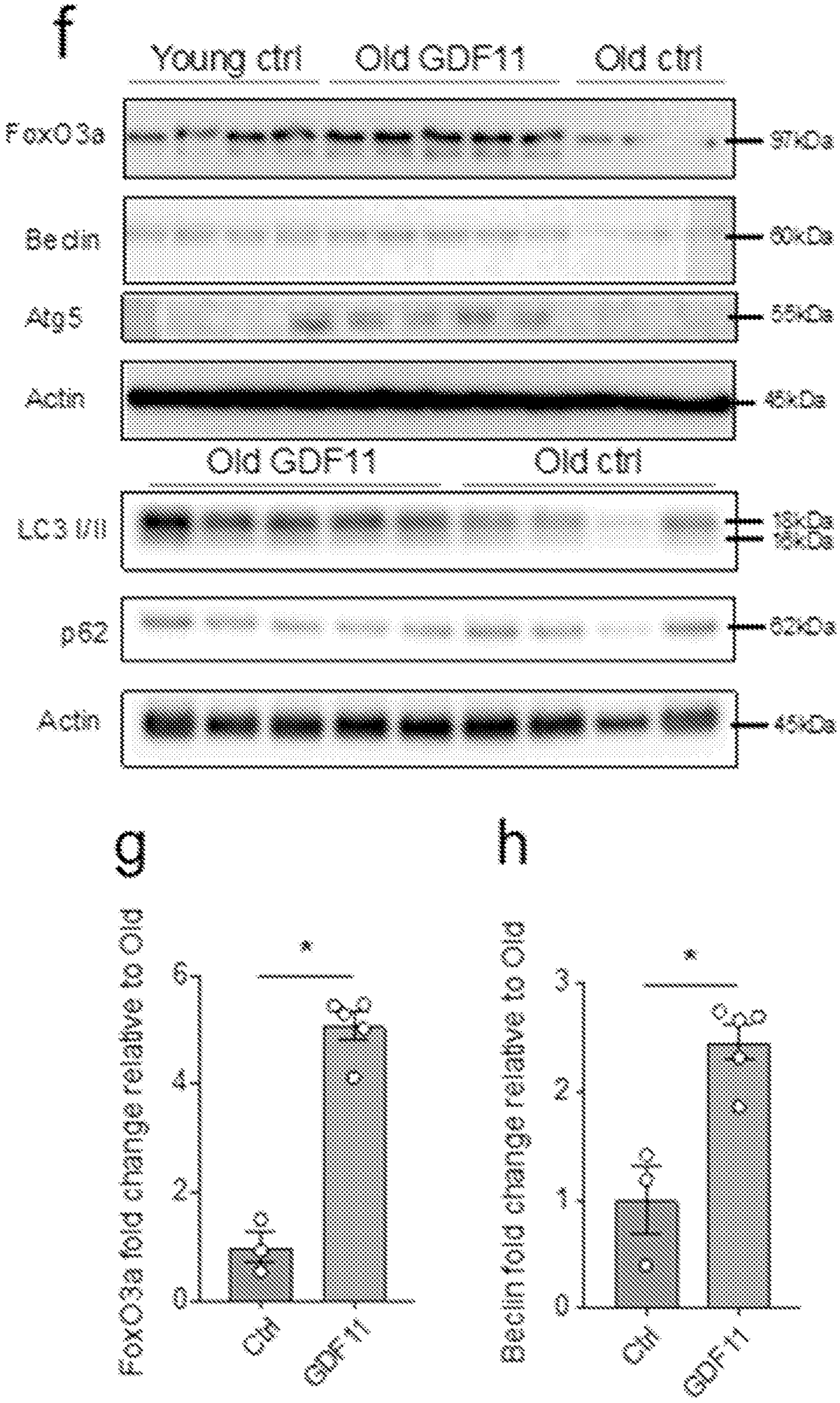

Figure 2 (continuation)
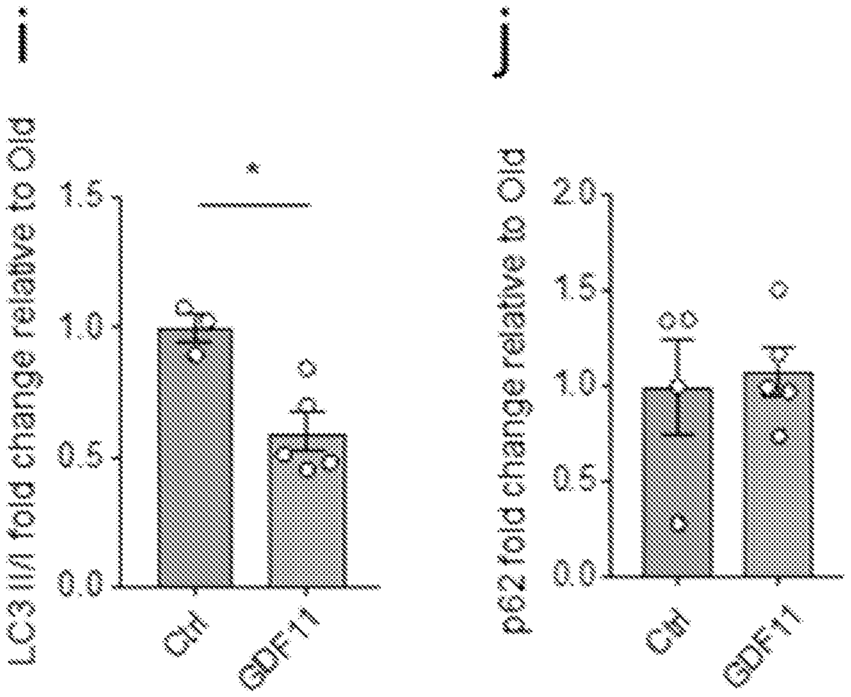
Figure 3
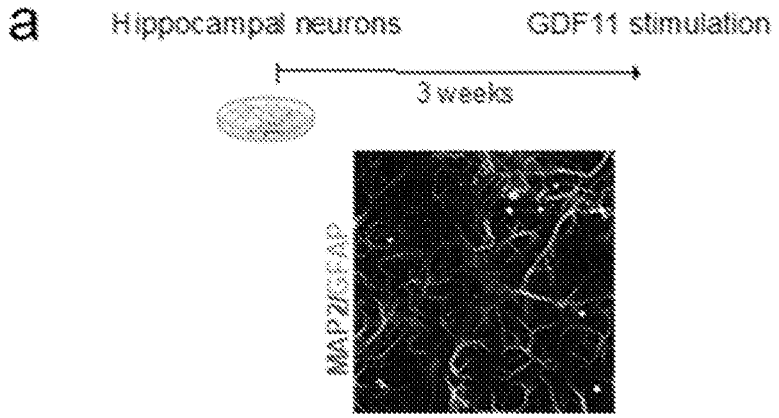

Figure 3 (continuation)
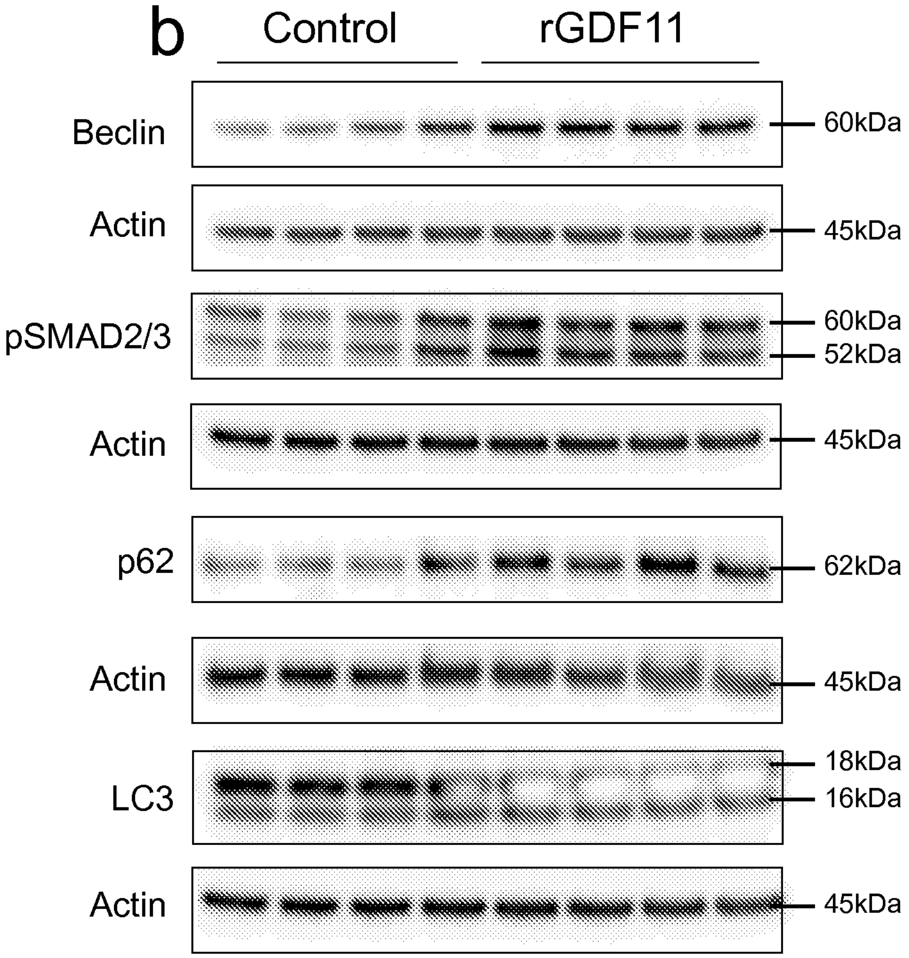

FIGURE 3 (continuation)
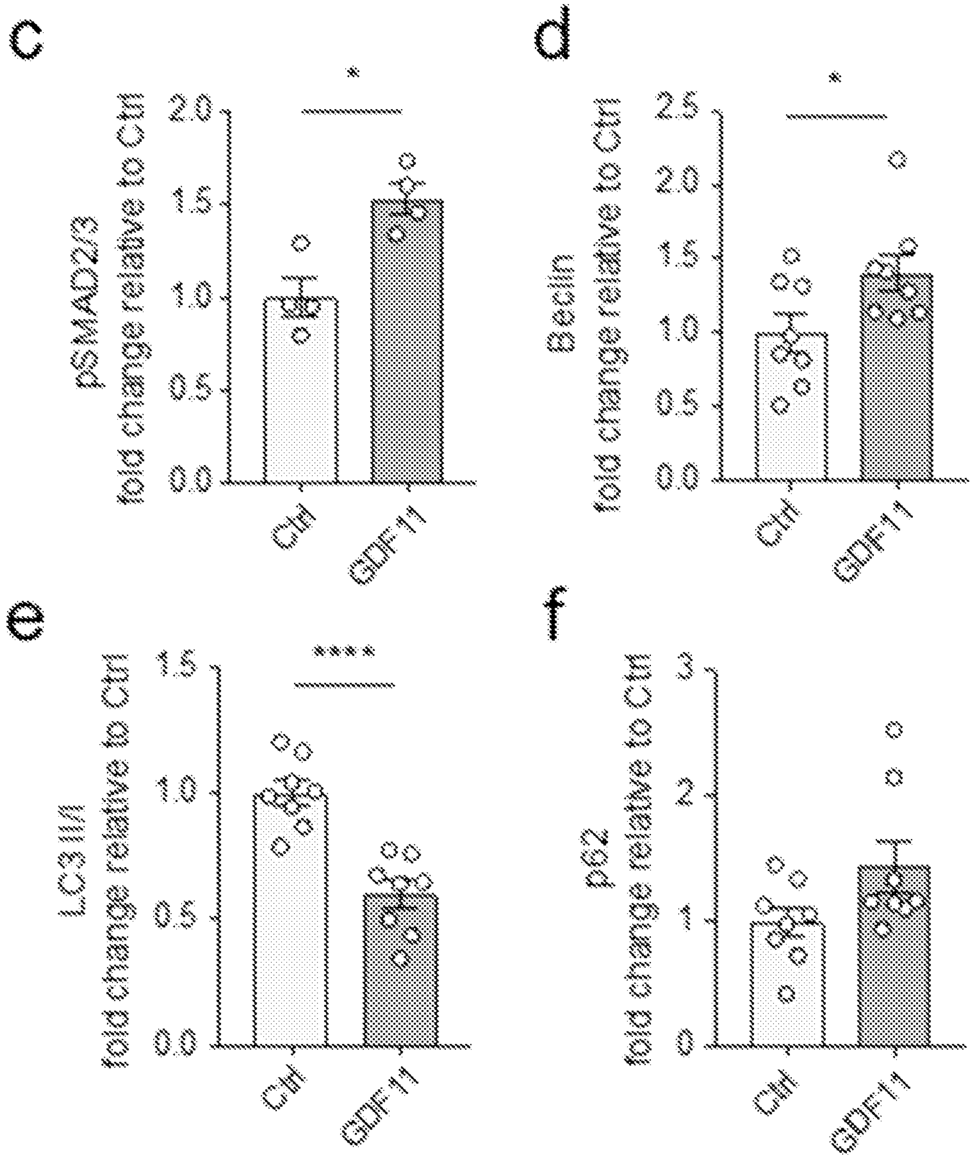
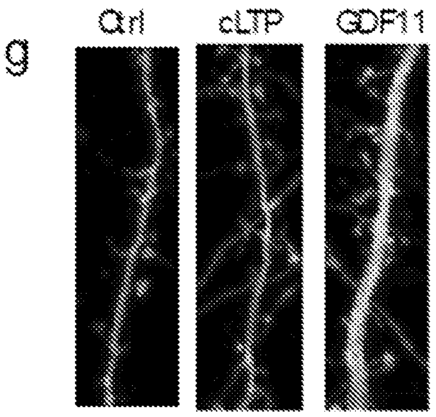

Figure 3 (continuation)
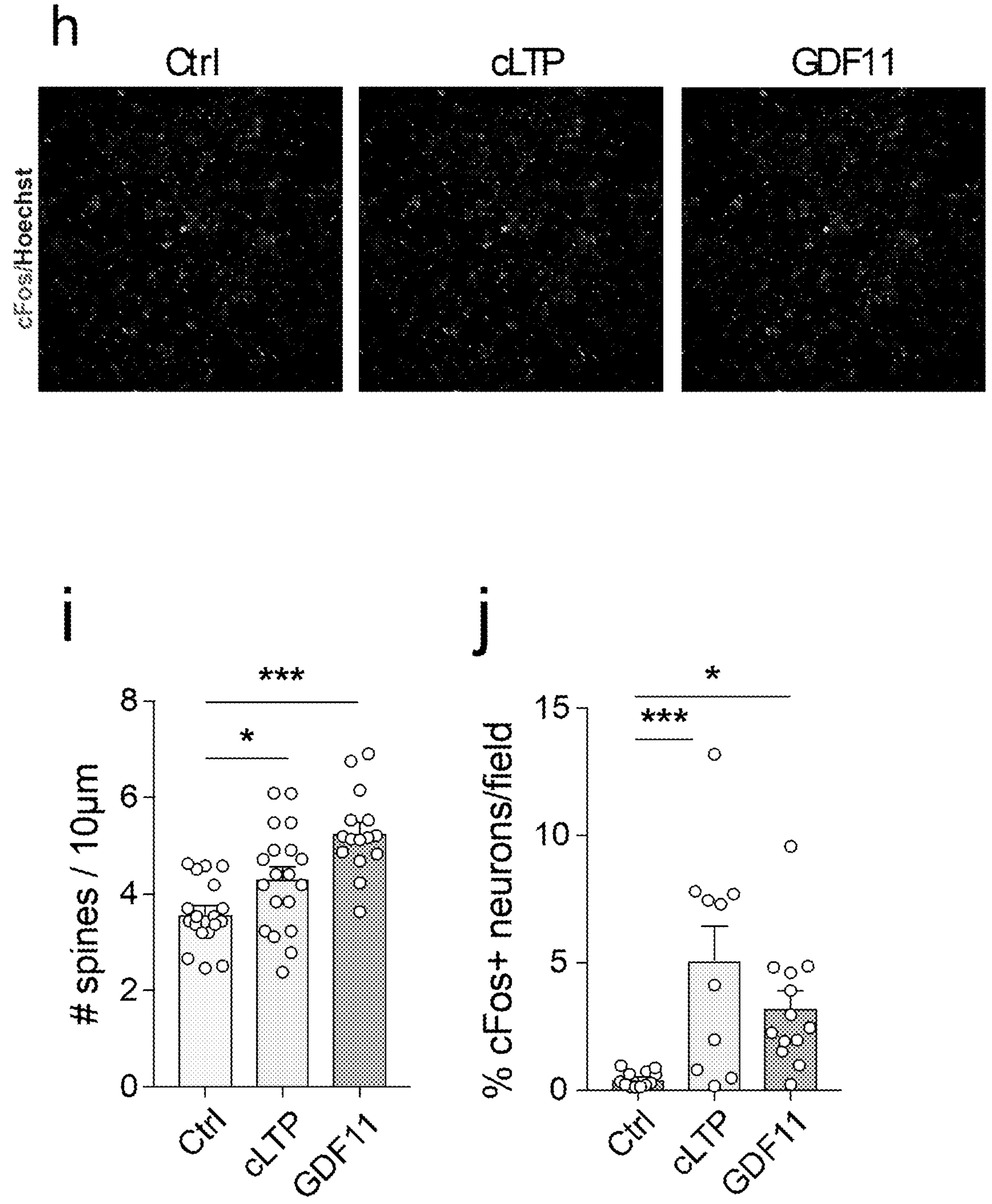

Figure 4 (Continuation)
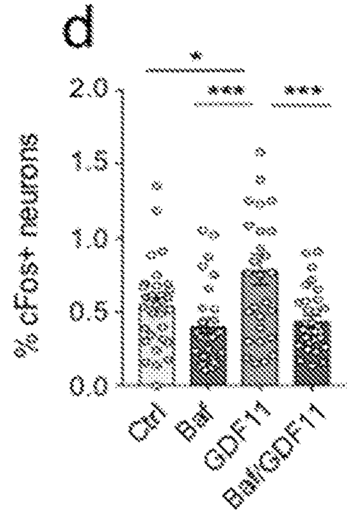
E
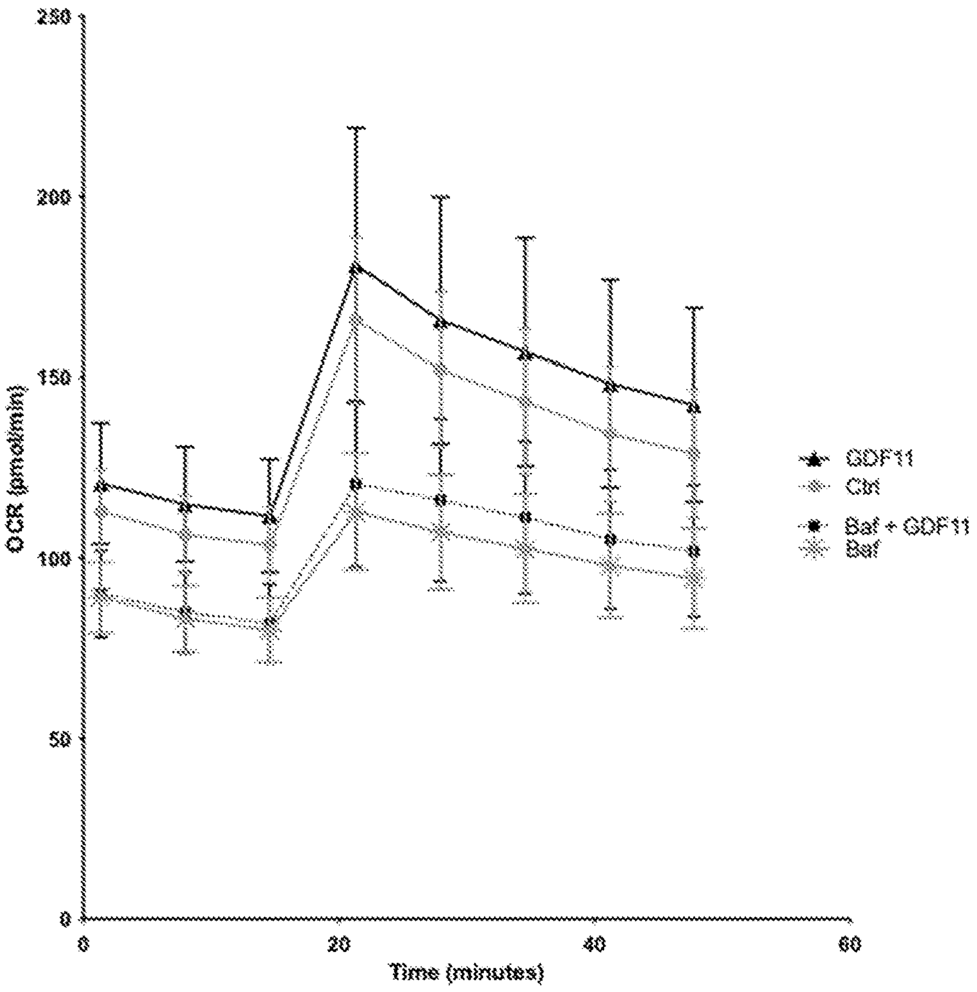

Figure 5 (continuation)
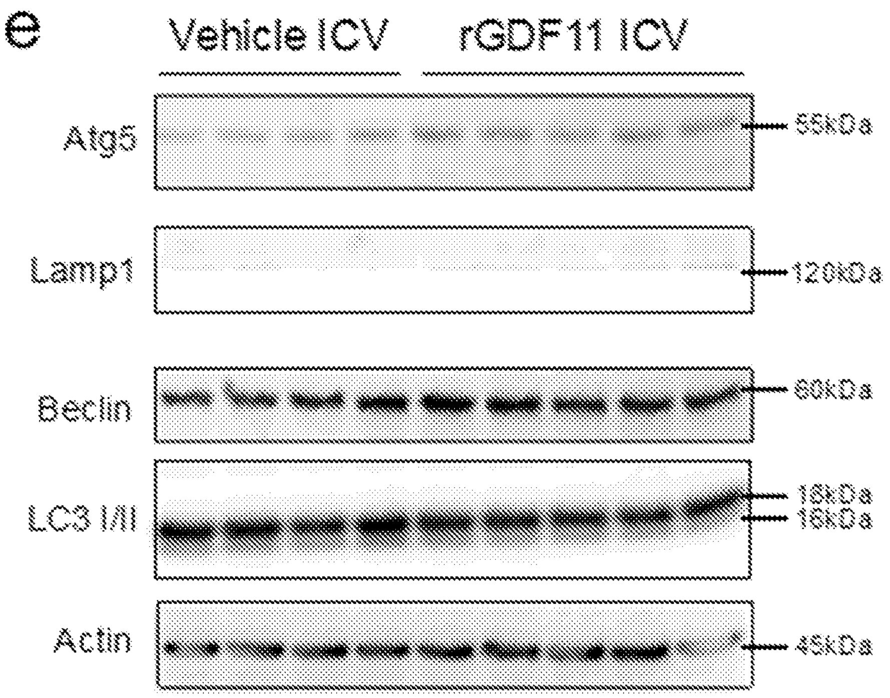
Figure 5 (continuation)
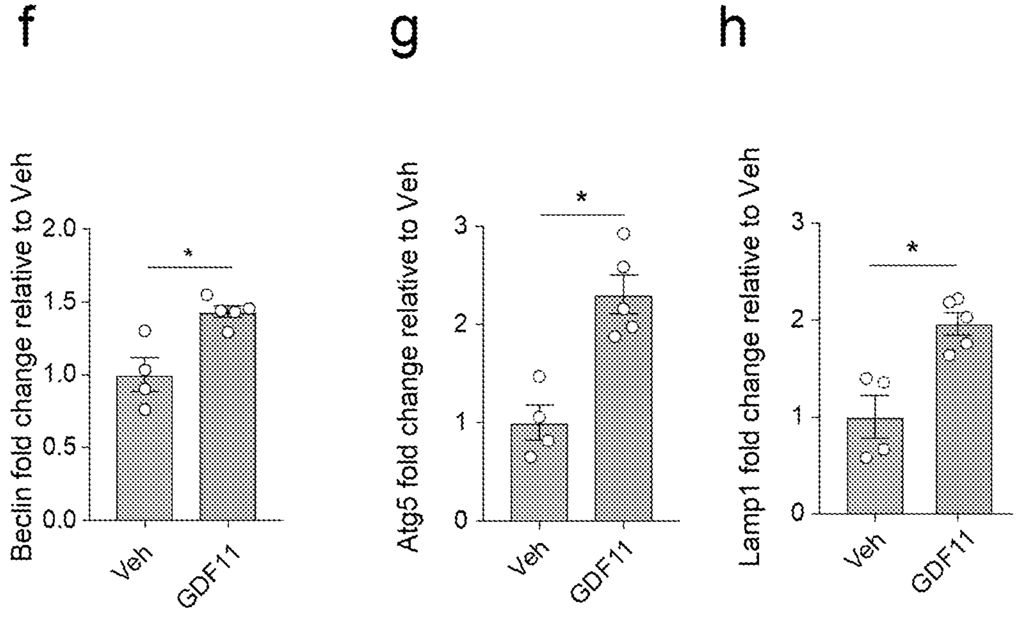

Figure 6 (continuation)
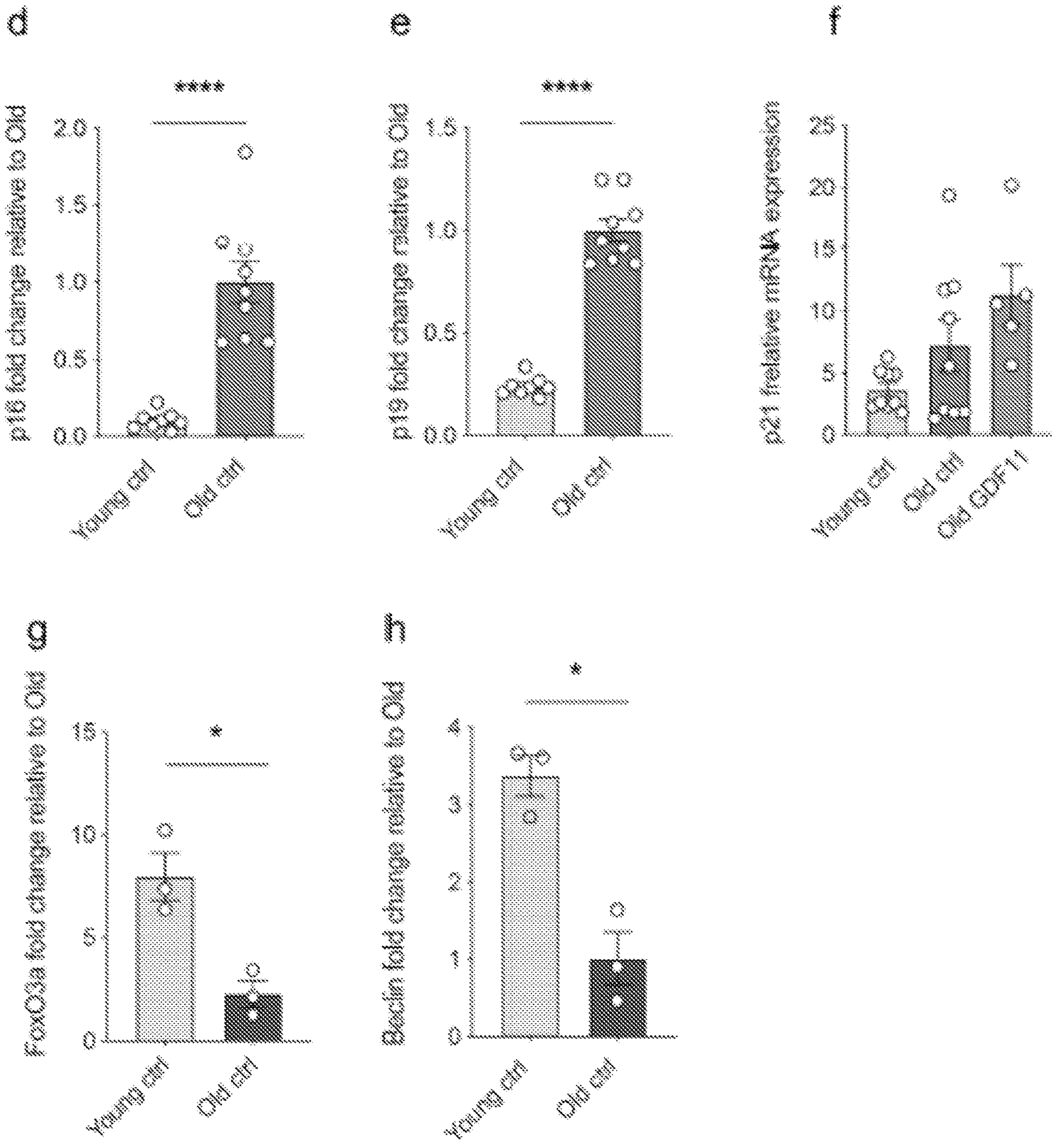

A

| GDF11 levels – ELISA assay | |
|---|---|
| Mean | 98.63 |
| Standard deviation | 101.24 |
| Median | 42.25 |
| Minimum | 7.19 |
| Maximum | 271.39 |

Figure 10 (continuation)
B
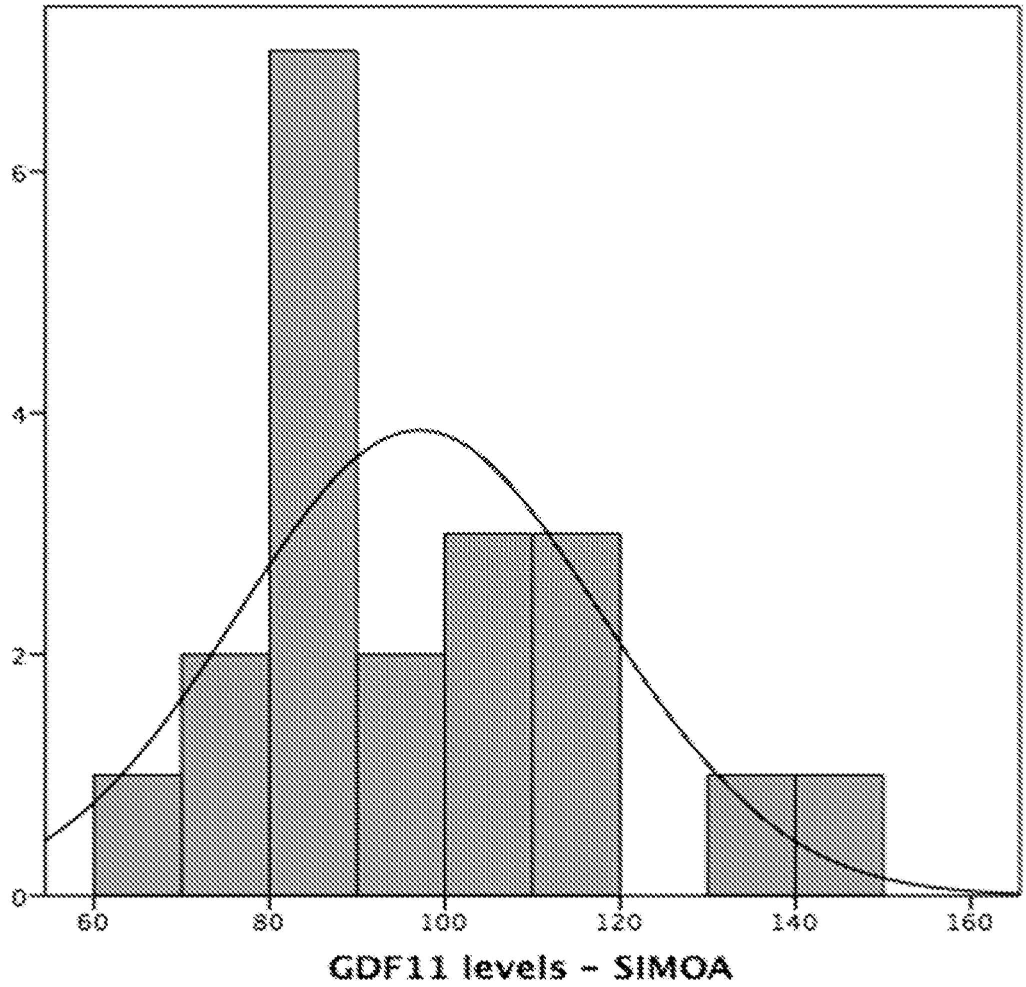
| GDF11 levels – Simoa assay | |
|---|---|
| Mean | 97.10 |
| Standard deviation | 20.69 |
| Median | 90.50 |
| Minimum | 69 |
| Maximum | 144 |

Figure 11 (continuation)
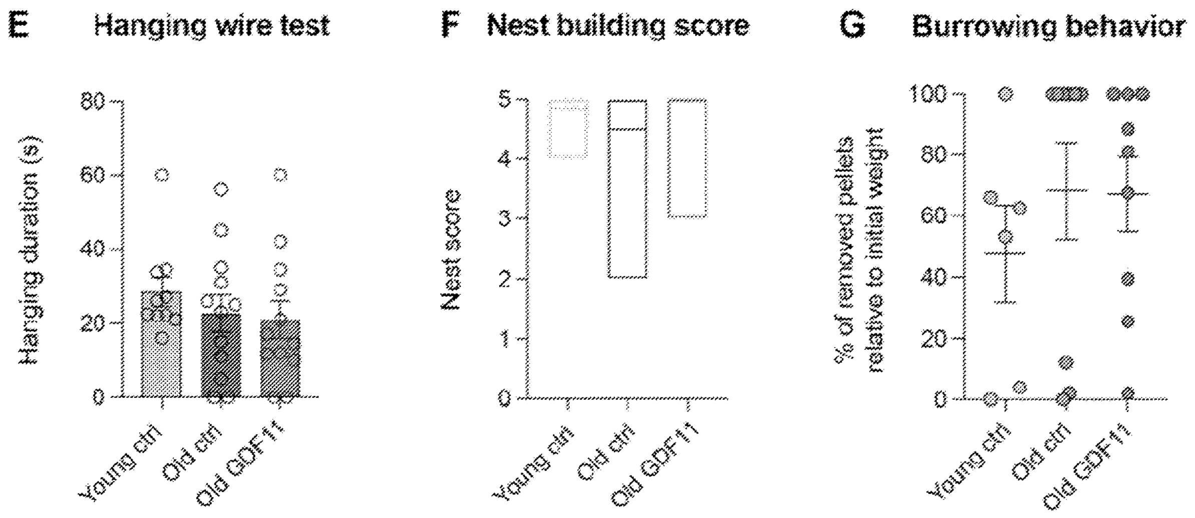

Figure 12 (continuation)
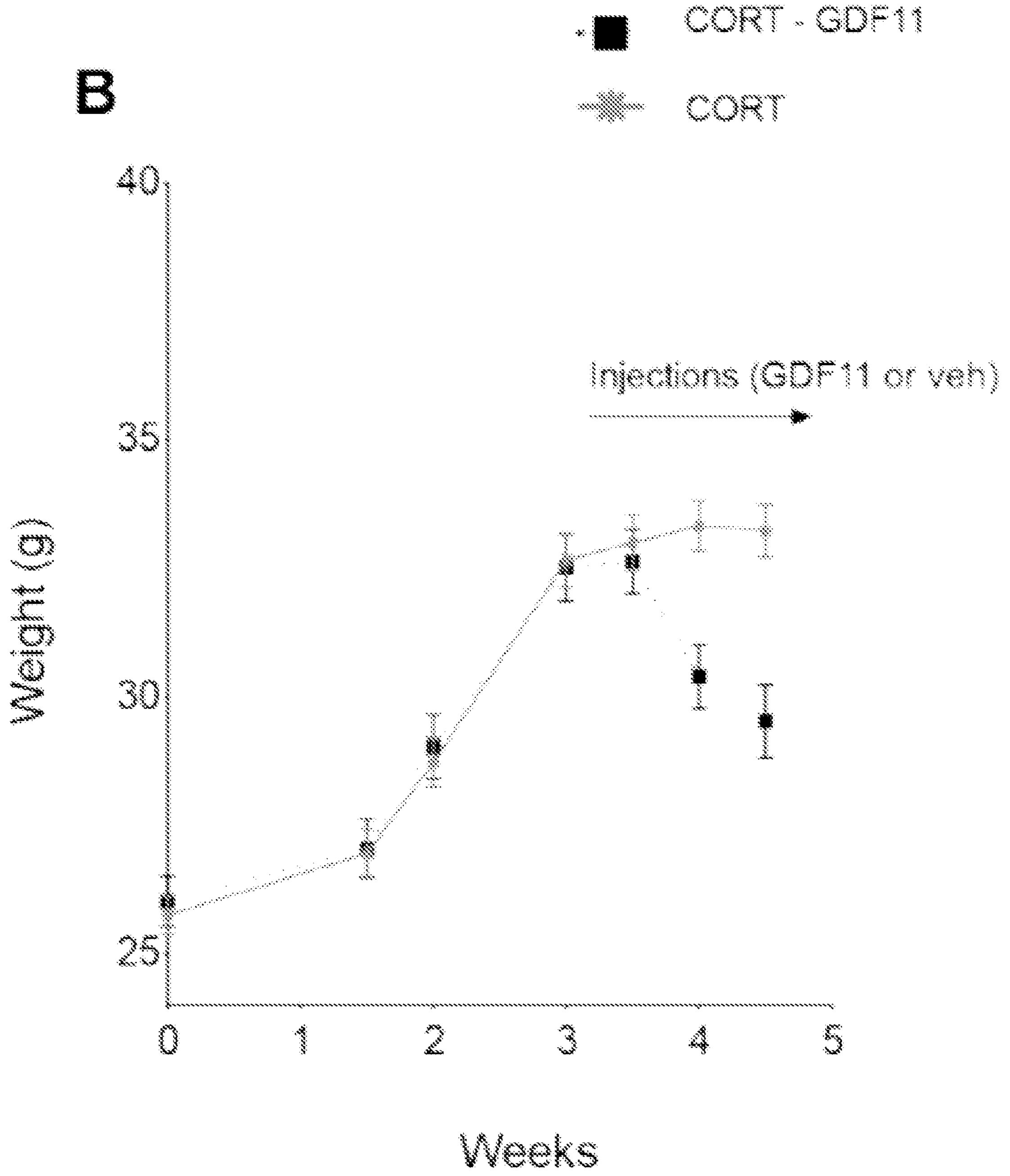

Figure 12 (continuation)
C
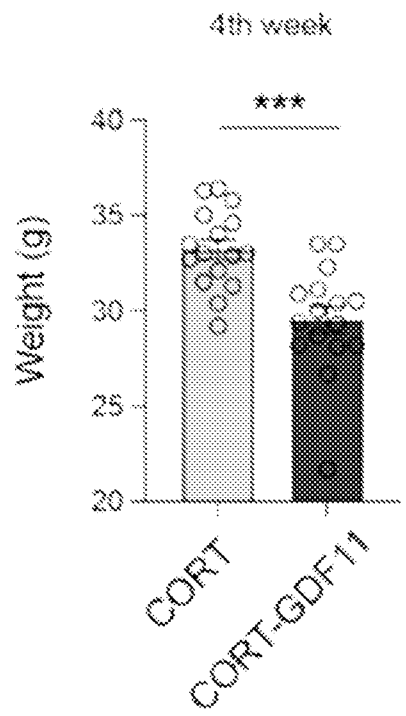
D
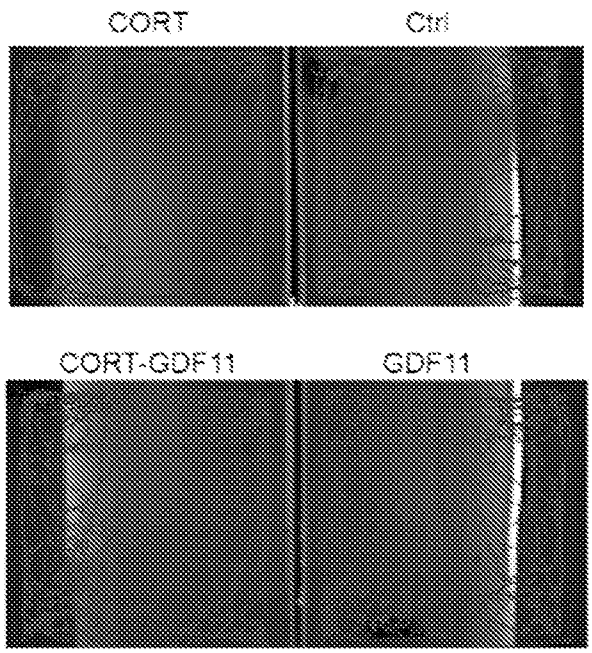

Figure 12 (continuation)
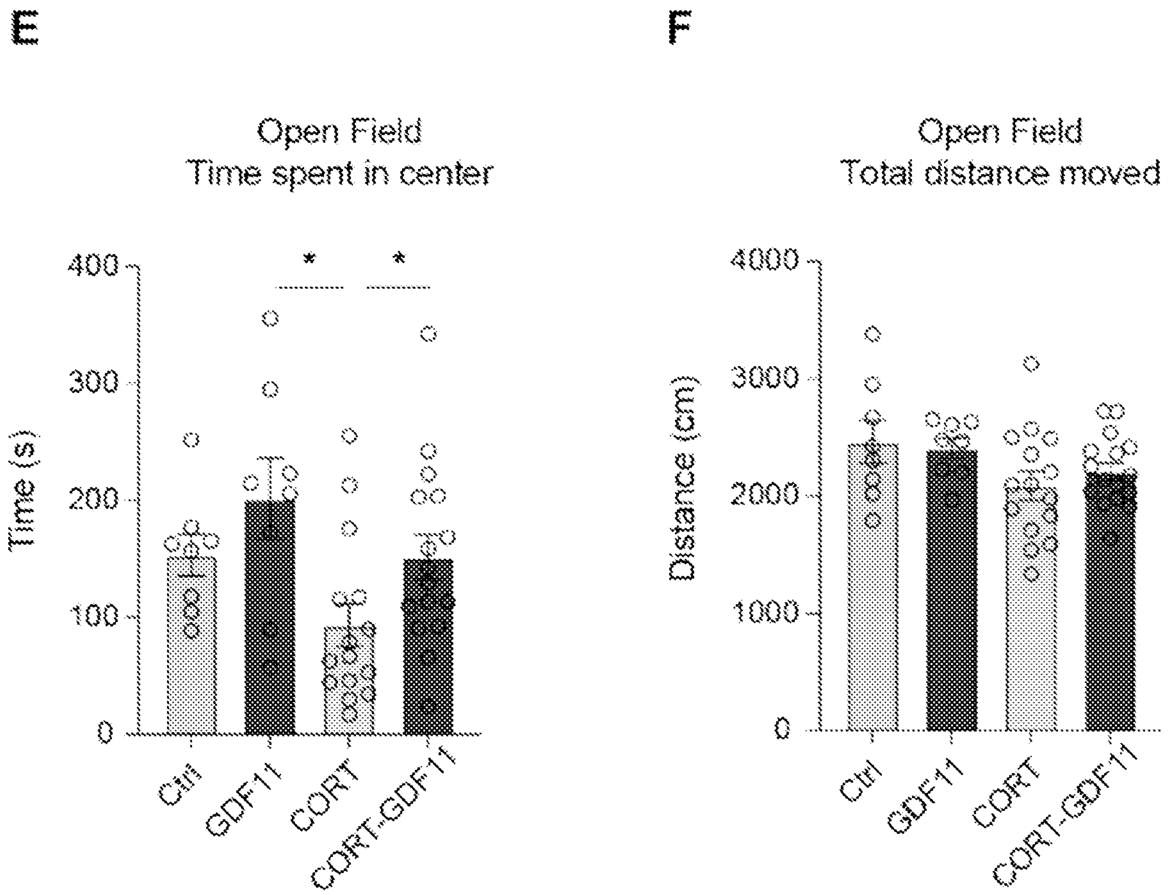

SEQUENCE LISTING

<160> NUMBER OF SEQ ID NOS: 5

<210> SEQ ID NO 1
<211> LENGTH: 407
<212> TYPE: PRT
<213> ORGANISM: homo sapiens
<220> FEATURE:
<221> NAME/KEY: MISC_FEATURE
<223> OTHER INFORMATION: human precursor of GDF11, NCBI Ref Seq: NP_005802

<400> SEQUENCE: 1

```
Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
    130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
        275                 280                 285

Val Leu Glu Asn Thr Lys Arg Ser Arg Arg Asn Leu Gly Leu Asp Cys
    290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
            340                 345                 350
```

Tyr Pro His Thr His Leu Val Gln Gln Ala Asn Pro Arg Gly Ser Ala
355 360 365

Gly Pro Cys Cys Thr Pro Thr Lys Met Ser Pro Ile Asn Met Leu Tyr
370 375 380

Phe Asn Asp Lys Gln Gln Ile Ile Tyr Gly Lys Ile Pro Gly Met Val
385 390 395 400

Val Asp Arg Cys Gly Cys Ser
405

<210> SEQ ID NO 2
<211> LENGTH: 383
<212> TYPE: PRT
<213> ORGANISM: homo sapiens
<220> FEATURE:
<221> NAME/KEY: MISC_FEATURE
<223> OTHER INFORMATION: human propeptide GDF11, 383 aa

<400> SEQUENCE: 2

Ala Glu Gly Pro Ala Ala Ala Ala Ala Ala Ala Ala Ala Ala Ala Ala
1 5 10 15

Ala Gly Val Gly Gly Glu Arg Ser Ser Arg Pro Ala Pro Ser Val Ala
20 25 30

Pro Glu Pro Asp Gly Cys Pro Val Cys Val Trp Arg Gln His Ser Arg
35 40 45

Glu Leu Arg Leu Glu Ser Ile Lys Ser Gln Ile Leu Ser Lys Leu Arg
50 55 60

Leu Lys Glu Ala Pro Asn Ile Ser Arg Glu Val Val Lys Gln Leu Leu
65 70 75 80

Pro Lys Ala Pro Pro Leu Gln Gln Ile Leu Asp Leu His Asp Phe Gln
85 90 95

Gly Asp Ala Leu Gln Pro Glu Asp Phe Leu Glu Glu Asp Glu Tyr His
100 105 110

Ala Thr Thr Glu Thr Val Ile Ser Met Ala Gln Glu Thr Asp Pro Ala
115 120 125

Val Gln Thr Asp Gly Ser Pro Leu Cys Cys His Phe His Phe Ser Pro
130 135 140

Lys Val Met Phe Thr Lys Val Leu Lys Ala Gln Leu Trp Val Tyr Leu
145 150 155 160

Arg Pro Val Pro Arg Pro Ala Thr Val Tyr Leu Gln Ile Leu Arg Leu
165 170 175

Lys Pro Leu Thr Gly Glu Gly Thr Ala Gly Gly Gly Gly Gly Gly Arg
180 185 190

Arg His Ile Arg Ile Arg Ser Leu Lys Ile Glu Leu His Ser Arg Ser
195 200 205

Gly His Trp Gln Ser Ile Asp Phe Lys Gln Val Leu His Ser Trp Phe
210 215 220

Arg Gln Pro Gln Ser Asn Trp Gly Ile Glu Ile Asn Ala Phe Asp Pro
225 230 235 240

Ser Gly Thr Asp Leu Ala Val Thr Ser Leu Gly Pro Gly Ala Glu Gly
245 250 255

Leu His Pro Phe Met Glu Leu Arg Val Leu Glu Asn Thr Lys Arg Ser
260 265 270

Arg Arg Asn Leu Gly Leu Asp Cys Asp Glu His Ser Ser Glu Ser Arg
275 280 285

Cys Cys Arg Tyr Pro Leu Thr Val Asp Phe Glu Ala Phe Gly Trp Asp
    290                 295                 300

Trp Ile Ile Ala Pro Lys Arg Tyr Lys Ala Asn Tyr Cys Ser Gly Gln
305                 310                 315                 320

Cys Glu Tyr Met Phe Met Gln Lys Tyr Pro His Thr His Leu Val Gln
                325                 330                 335

Gln Ala Asn Pro Arg Gly Ser Ala Gly Pro Cys Cys Thr Pro Thr Lys
            340                 345                 350

Met Ser Pro Ile Asn Met Leu Tyr Phe Asn Asp Lys Gln Gln Ile Ile
        355                 360                 365

Tyr Gly Lys Ile Pro Gly Met Val Val Asp Arg Cys Gly Cys Ser
    370                 375                 380

<210> SEQ ID NO 3
<211> LENGTH: 109
<212> TYPE: PRT
<213> ORGANISM: homo sapiens
<220> FEATURE:
<221> NAME/KEY: MISC_FEATURE
<223> OTHER INFORMATION: human mature form of GDF11

<400> SEQUENCE: 3

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 4
<211> LENGTH: 274
<212> TYPE: PRT
<213> ORGANISM: homo sapiens
<220> FEATURE:
<221> NAME/KEY: MISC_FEATURE
<223> OTHER INFORMATION: human N-terminal polypeptide GDF11

<400> SEQUENCE: 4

Ala Glu Gly Pro Ala Ala Ala Ala Ala Ala Ala Ala Ala Ala Ala Ala
1               5                   10                  15

Ala Gly Val Gly Gly Glu Arg Ser Ser Arg Pro Ala Pro Ser Val Ala
            20                  25                  30

Pro Glu Pro Asp Gly Cys Pro Val Cys Val Trp Arg Gln His Ser Arg
        35                  40                  45

Glu Leu Arg Leu Glu Ser Ile Lys Ser Gln Ile Leu Ser Lys Leu Arg
    50                  55                  60

-continued

Leu Lys Glu Ala Pro Asn Ile Ser Arg Glu Val Val Lys Gln Leu Leu
65 70 75 80

Pro Lys Ala Pro Pro Leu Gln Gln Ile Leu Asp Leu His Asp Phe Gln
85 90 95

Gly Asp Ala Leu Gln Pro Glu Asp Phe Leu Glu Glu Asp Glu Tyr His
100 105 110

Ala Thr Thr Glu Thr Val Ile Ser Met Ala Gln Glu Thr Asp Pro Ala
115 120 125

Val Gln Thr Asp Gly Ser Pro Leu Cys Cys His Phe His Phe Ser Pro
130 135 140

Lys Val Met Phe Thr Lys Val Leu Lys Ala Gln Leu Trp Val Tyr Leu
145 150 155 160

Arg Pro Val Pro Arg Pro Ala Thr Val Tyr Leu Gln Ile Leu Arg Leu
165 170 175

Lys Pro Leu Thr Gly Glu Gly Thr Ala Gly Gly Gly Gly Gly Gly Arg
180 185 190

Arg His Ile Arg Ile Arg Ser Leu Lys Ile Glu Leu His Ser Arg Ser
195 200 205

Gly His Trp Gln Ser Ile Asp Phe Lys Gln Val Leu His Ser Trp Phe
210 215 220

Arg Gln Pro Gln Ser Asn Trp Gly Ile Glu Ile Asn Ala Phe Asp Pro
225 230 235 240

Ser Gly Thr Asp Leu Ala Val Thr Ser Leu Gly Pro Gly Ala Glu Gly
245 250 255

Leu His Pro Phe Met Glu Leu Arg Val Leu Glu Asn Thr Lys Arg Ser
260 265 270

Arg Arg

<210> SEQ ID NO 5
<211> LENGTH: 109
<212> TYPE: PRT
<213> ORGANISM: mus musculus
<220> FEATURE:
<221> NAME/KEY: MISC_FEATURE
<223> OTHER INFORMATION: monomer of GDF11 injected in murin model

<400> SEQUENCE: 5

Asn Leu Gly Leu Asp Cys Asp Glu His Ser Ser Glu Ser Arg Cys Cys
1 5 10 15

Arg Tyr Pro Leu Thr Val Asp Phe Glu Ala Phe Gly Trp Asp Trp Ile
20 25 30

Ile Ala Pro Lys Arg Tyr Lys Ala Asn Tyr Cys Ser Gly Gln Cys Glu
35 40 45

Tyr Met Phe Met Gln Lys Tyr Pro His Thr His Leu Val Gln Gln Ala
50 55 60

Asn Pro Arg Gly Ser Ala Gly Pro Cys Cys Thr Pro Thr Lys Met Ser
65 70 75 80

Pro Ile Asn Met Leu Tyr Phe Asn Asp Lys Gln Gln Ile Ile Tyr Gly
85 90 95

Lys Ile Pro Gly Met Val Val Asp Arg Cys Gly Cys Ser
100 105

USE OF GDF11 TO DIAGNOSE AND TREAT ANXIETY AND DEPRESSION

BACKGROUND OF THE INVENTION

It is estimated that 792 million people are living with a mental health disorder, accounting for 11% of our global population (Ritchie & Roser, 2018[18]). Bipolar disorder (BD), major depressive disorder (MDD), and anxiety disorders account for 594 million of the mental health disorder population and are associated with a high level of disability and a reduced life expectancy in comparison to the general population (Chesney, Goodwin, & Fazel, 2014[12]). Although the longitudinal course of mood disorders is heterogeneous, there is evidence suggesting clinical progression in a subset of patients with mood disorders. In addition, a recent study showed that progressive functional deterioration occurs in about 50% of patients with BD (Lopez-Villarreal et al., 2019[17]). These patients experience a higher number of relapses and hospitalizations, as well as worse neurocognitive functioning (López-Villarreal et al., 2019[17]).

Furthermore, mood disorders have been considered as diseases of accelerated aging (Squassina, Pisanu & Vanni, 2019[19]; Fries et al., 2020[14]). They are associated with a shortened life span compared to the general population, which has been related to chronic health conditions usually associated with aging, such as cardiovascular, respiratory, and infectious diseases, hypertension, and diabetes. A published systematic review and meta-analysis showed that almost 70% of deaths among people with psychiatric disorders are due to natural causes (Walker, McGee, & Druss, 2015[20]). Most of these deaths are accounted for by chronic physical medical conditions that are usually associated with aging, such as cardiovascular, respiratory, and infectious diseases, diabetes, and hypertension.

Studies have begun to focus on the distinction between chronological and biological age. Of particular relevance, mood disorders have been associated with biological aging markers such as telomere length, inflammatory markers, oxidative stress, DNA methylation, and genetic markers (Fries et al., 2020[14]). In a previous study using mouse models, scientists from Institut Pasteur observed that injecting aged mice with blood from young mice rejuvenated blood vessels in the brain, and consequently improved cerebral blood flow, while increasing neurogenesis and cognition (Katsimpardi et al, 2014[2]). They thereafter examined the molecule GDF11, which belongs to the GDF (Growth Differentiation Factor) protein family. GDF11 was already known for its ability to rejuvenate the aged brain: by injecting this molecule into aged mouse models, they noticed an increase in neurogenesis and blood vessel remodeling (Katsimpardi et al, 2015[15]). Of wide interest for mental health is the relation existing between depression and adult neurogenesis. The identification of systemic factors related to age-dependent brain impairments, including the degree of adult neurogenesis, may constitute the basis for new therapies of psychiatric disorders.

A need exists to both identify new mechanisms to treat mood disorders (including depression and bipolar disorder) and anxiety disorders, and new ways to prognose and/or diagnose patients suffering from these disorders and patients who will respond to unique treatments.

Chronic mood and anxiety disorders have been considered risk factors for accelerated aging. In addition, mood and anxiety disorders are associated with high rates of conversion to dementia. These disorders are associated with a shortened life span compared to the general population, which has been related to chronic health conditions usually associated with aging, such as cardiovascular, hypertension, and diabetes. Of particular relevance, mood and anxiety disorders have been associated with biological aging markers such as telomere length. Another need exists to identify the accelerated aging process among these patients and to have specific therapeutic compound that treat these disorders and prevent or reverse the accelerated aging effects of such conditions.

The invention disclosed herein meet these and other needs.

SUMMARY OF THE INVENTION

In both rodents and humans, levels of GDF11 decline with age. The data presented by the inventors in the examples demonstrates that GDF11 levels are a biomarker for anxiety/mood disorder, including depression, and a useful tool for diagnosis, treatment and prognosis for mood and/or anxiety disorders and mental health in general.

In a first aspect, this invention provides methods for the detection of GDF11 in a subject having or suspected of having a mood and/or anxiety disorder. The method may comprise providing a sample from a subject having or suspected of having a mood and/or anxiety disorder; contacting the sample with a GDF11-binding molecule; and detecting bound GDF11. In a particular embodiment, the disorder is a mood disorder. In a preferred embodiment, the mood disorder is a major depressive disorder. In a particular embodiment, the subject has been clinically diagnosed with the mood and/or anxiety disorder. In a particular embodiment, the subject is undergoing treatment for the mood and/or anxiety disorder. In a particular embodiment, the subject is a human. In a particular embodiment, the subject is less than 65 years old. In a particular embodiment, the sample is plasma or serum. In a particular embodiment, the GDF11-binding molecule is an anti-GDF11 antibody or a molecule comprising an antigen-binding fragment of an anti-GDF11 antibody. In a particular embodiment, the method comprises an enzyme-linked immunosorbent assay (ELISA) or an ultrasensitive single molecule array (Simoa) technology. In a particular embodiment, the methods further comprise measuring the GDF11 levels in the subject sample. In a particular embodiment, the levels of GDF11 in the sample are significantly lower than a healthy reference level. In a particular embodiment, the levels of GDF11 in the sample are not significantly lower than a healthy reference level.

In another aspect, this invention provides a method for prognosing or diagnosing or characterizing a mood and/or anxiety disorder, and optionally the accelerated aging associated therewith, in a subject. The method may comprise measuring GDF-11 levels in the subject and comparing the measured levels of GDF11 to healthy reference levels. In a particular embodiment, the health reference point will be a composite/combination of several parameters: telomere length, C-reative protein (CRP) value, and possibly scores on mood and anxiety questionnaires. In a particular embodiment, biological age as defined by the health reference described above, will prevail over chronological age.

The method may comprise providing a sample from a subject; contacting the sample with a GDF11-binding molecule; detecting bound GDF11; and comparing the levels of detected bound GDF11 to healthy reference levels. In a particular embodiment, if the levels of detected bound GDF11 are significantly lower than healthy reference levels, the subject is prognosed or diagnosed with the mood and/or anxiety disorder. In a particular embodiment, if the levels of detected bound GDF11 are not significantly lower than healthy reference levels the subject is not prognosed nor diagnosed as having the mood and/or anxiety disorder. In a particular embodiment, the mood disorder is a depressive disorder. In a particular embodiment, the mood disorder is a major depressive disorder. In a particular embodiment, the subject is undergoing treatment for the mood and/or anxiety disorder. In a particular embodiment, the subject is a human. In a particular embodiment, the subject is less than 65 years old. In a particular embodiment, the sample is plasma or serum. In a particular embodiment, the GDF11-binding molecule is an anti-GDF11 antibody or a molecule comprising an antigen-binding fragment of an anti-GDF11 antibody. In a particular embodiment, the method comprises an enzyme-linked immunosorbent assay (ELISA) or an ultra-sensitive single molecule array (Simoa) technology.

In another aspect, this invention provides a method of treating or preventing a mood and/or anxiety disorder, and optionally reducing or reversing the accelerated aging associated therewith, in a subject in need thereof, comprising administering to the subject an agent or composition which increases GDF11 polypeptide levels in the subject.

In a particular embodiment, the disorder is a mood disorder. In a particular embodiment, the mood disorder is a depressive disorder. In a particular embodiment, the mood disorder is a major depressive disorder. In a particular embodiment, the agent or composition comprises an agonist antibody that increases expression of GDF11. In a particular embodiment, the agent or composition comprises a GDF11 polypeptide.

In a particular embodiment, the GDF11 polypeptide is detected by ELISA kit from R&D Systems (Human GDF-11/BMP-11 DuoSet ELISA; Catalog #: DY1958-05).

In a particular embodiment, the GDF11 polypeptide comprises or consists of the amino acid sequence of SEQ ID NO:1, SEQ ID NO:2, or SEQ ID NO:3. In a particular embodiment, the agent or composition comprises homodimers of GDF11 polypeptides comprising the amino acid sequence of any of SEQ ID NOs: 1, 2, or 3. In a particular embodiment, the agent or composition comprises complexes of GDF11 polypeptides comprising the amino acid sequence of at least one of SEQ ID NOS: 1, 2, or 3. In a particular embodiment, the agent or composition comprises a nucleic acid encoding a GDF11 polypeptide or a functional fragment or variant thereof. In a particular embodiment, the GDF11 polypeptide comprises a modified GDF11 polypeptide. In a particular embodiment, the GDF11 polypeptide comprises a tag. In a particular embodiment, the modified GDF11 polypeptide comprises a modification selected from the group consisting of fusion to an Fc fragment, PEGylation, conjugation to albumin, an amino acid mutation that prevents or reduces proteolytic degradation, an amino acid mutation that prolongs half-life, and any combination thereof. In a particular embodiment, the composition is administered via a route selected from the group consisting of intravenously, subcutaneously, intra-arterially, and intra-muscularly. In a particular embodiment, the GDF11 polypeptide levels increase by at least 25%, 50%, 75% or 100% of a healthy reference level. In a particular embodiment, the subject does not suffer from a neurodegenerative disorder. In a particular embodiment, the subject being treated is prognosed or diagnosed with the mood disorder by a method of the invention prior to administering the agent or composition to the subject. In a particular embodiment, the effectiveness of the treatment or prevention is characterized by a method of the invention.

In another aspect, this invention provides methods of screening a compound. The method may comprise administering a test compound to a subject having a mood disorder and/or an anxiety disorder and detecting GDF-11 in the subject. The methods may comprise administering a test compound to a subject having a mood disorder and/or an anxiety disorder; obtaining a sample from the subject; contacting the sample with a GDF11-binding molecule; and detecting bound GDF11. In a particular embodiment, the mood disorder is a depressive disorder. In a particular embodiment, the mood disorder is a major depressive disorder. In a particular embodiment, the subject is a human. In a particular embodiment, the subject is less than 65 years old. In a particular embodiment, the sample is plasma or serum. In a particular embodiment, the GDF11-binding molecule is an anti-GDF11 antibody or a molecule comprising an antigen-binding fragment of an anti-GDF11 antibody. In a particular embodiment, the method comprises an enzyme-linked immunosorbent assay (ELISA) or an ultra-sensitive single molecule array (Simoa) technology. In a particular embodiment, the methods further comprise measuring GDF11 levels in the subject sample. In a particular embodiment, the levels of GDF11 in the sample are significantly lower than healthy reference levels and the test compound is not identified as having a mood disorder treating activity. In a particular embodiment, the levels of GDF11 in the sample are not significantly lower than healthy reference levels and the test compound is identified as having a mood disorder treating activity.

BRIEF DESCRIPTION OF THE DRAWINGS

FIG. 1*f*). Mann-Whitney test for two-group comparisons; *P<0.05, mean and interquartile range.

FIG. 2. Systemic GDF11 administration reverses age-associated decline in neurogenesis and autophagy and decreases senescence. (a) Representative confocal images of the dentate gyrus of the hippocampus immunostained for Sox2 (red) and DAPI (blue); Scale bar: 100 μm. (b) Quantification of $Sox2^+$ NSCs in the SGL of the dentate gyrus ($n_Y$=6, $n_{GDF11}$=8, $n_O$=7 mice per group). (c) Quantification of $DCX^+$ neuroblasts in the SGL of the dentate gyrus ($n_Y$=4, $n_{GDF11}$=8, $n_O$=9 mice per group). (d-e) Real-time qPCR for hallmarks of senescence showing fold changes in mRNA levels of ARF (d) and p16 (e) for old GDF11 and old control, relative to young control ($n_Y$=8, $n_{GDF11}$=4, $n_O$=9 mice per group). (f) Western blot of hippocampal lysates from young, old and GDF11-treated old mice after 9 days of treatment. (g j) Quantification of Western blots by optical intensity for Foxo3a ($n_{GDF11}$=5, $n_O$=4 mice per group) (g), Beclin ($n_Y$=3, $n_{GDF}$=5, $n_O$=3 mice per group) (h), LC3 ($n_{GDF11}$=5, $n_O$=4 mice per group) (i) and p62 ($n_{GDF11}$=5, $n_O$=4 mice per group) (i). Mann-Whitney test for two-group comparisons; *P<0.05, **P<0.01; mean±S.E.M.

FIG. 3. GDF11 directly activates neurons and enhances neuronal activity. (a) Schematic representation of the neuronal culture in vitro (b) Western blot of hippocampal lysates from hippocampal neurons treated with GDF11 or control. (c-f) Quantification of Western blots by optical density for phosphoSMAD (n=4 mice per group) (c), Beclin (n=8 mice per group) (d), LC3 (n=4 mice per group) (e), and p62 (n=4 mice per group) (f). (g) Representative confocal images of GFP+ dendrites and spines from hippocampal neurons in culture. (h) Representative confocal images of hippocampal neurons in vitro immunostained with cFos (green) and Hoechst (blue). (i) Quantification of dendritic spine density (g) after a 2-hour stimulation with either GDF11 or cLTP (number represents number of spines for every 10 um of primary dendrite). (j) Quantification of (h) cFos+ neurons per field. Mann-Whitney test for two-group comparisons; *P<0.05, **P<0.01; mean±S.E.M.

(A) Measurement of time spent in the open arms of the Elevated Plus Maze (n=10-12 mice per group). (B) Measurement of sucrose preference index (amount of sweetened water consumed divided by total amount of liquids consumed) (n=10-12 mice per group). (C) Measurement of time spent on exploring the stimulus mouse/intruder by sniffing the face (n=3 mice per group). (D) Measurement of time spent avoiding contact with the stimulus mouse/intruder (n=3 mice per group). (E) Measurement of the time mice spent hanging on the wire for a total duration of 6 min (n=10-12 mice per group). (F) Evaluation of nest-building capacity by scoring the quality of the nest (n=10-12 mice per group). (G) Evaluation of burrowing behavior by measuring the weight of the pellets removed divided by the initial weight of the pellets in the burrowing tubes (n=10-12 mice per group). One-way ANOVA and Tukey's post hoc test for multiple comparisons; *P<0.05, P<0.01; *P<0.001; ****P<0.0001; mean±S.E.M.

Figure 12:
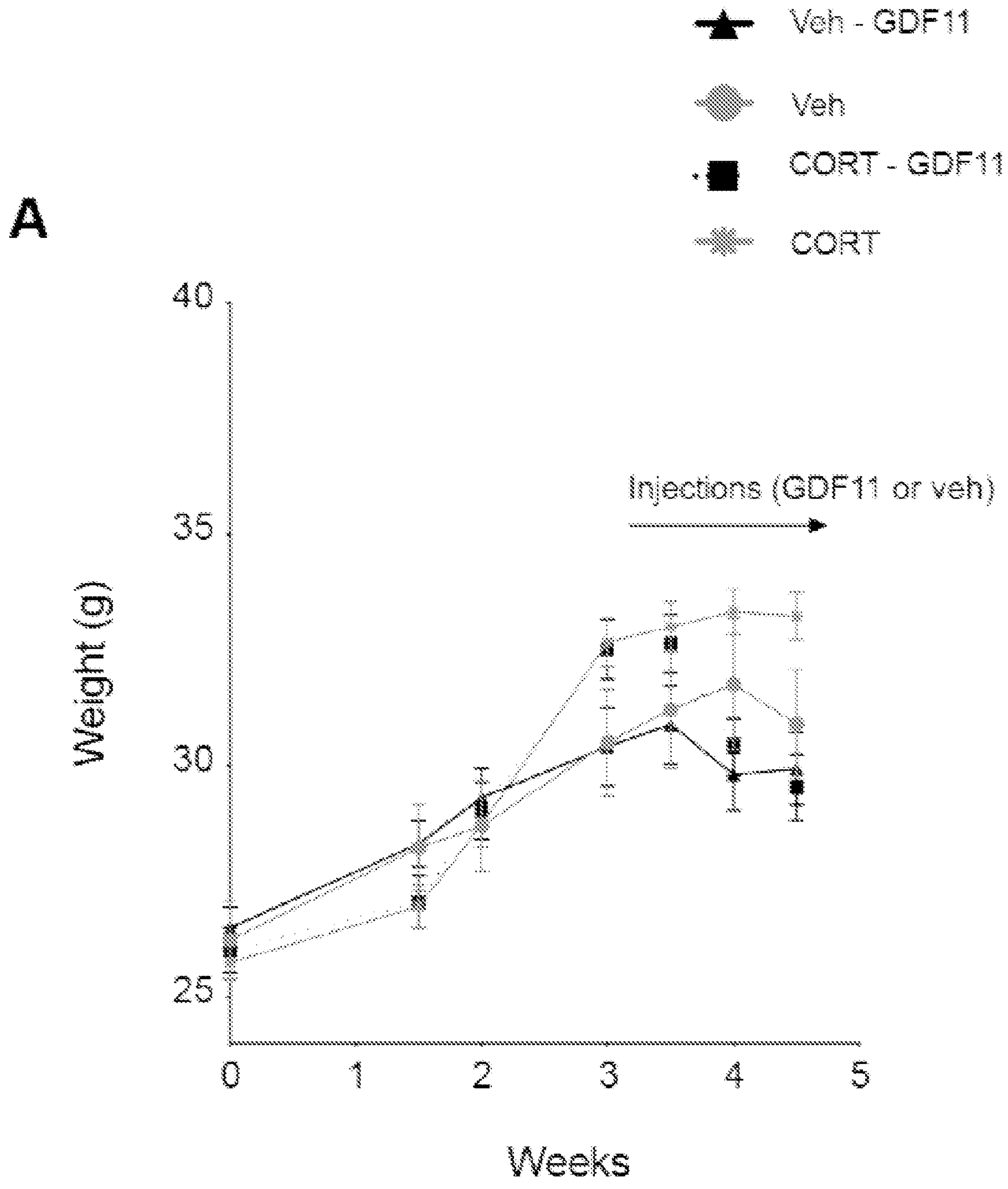

FIG. 12. Systemic GDF11 administration induces weight loss and attenuates anxiety in a mouse model of depression.

(A) Graph showing weekly weight measurements during administration of CORT or vehicle. The arrow indicates the start of daily GDF11 or saline (veh) injections (n=8-16 mice per group). (B) Same graph as in (A) depicting only the mice undergoing CORT treatment (n=8-16 mice per group). (C) Measurement of weight in CORT mice after 10 days of GDF11 or saline injections (n=16 mice per group). (D) Representative traces of the four different conditions in the Open Field test (CORT (CORT administration, no GDF11), Ctrl (no CORT, no GDF11), CORT-GDF11 (CORT administration and GDF11 treatment, and GDF11 (no CORT, GDF11 treatment). (E) Measurement of the time mice spent in the center of the arena during the Open Field test (n=8-16 mice per group). (F) Measurement of the total distance traveled by mice in the arena during the Open Field test (n=8-16 mice per group). Mann-Whitney test for two-group comparisons; One-way ANOVA and Tukey's post hoc test for multiple comparisons; *P<0.05, P<0.01; *P<0.001; ****P<0.0001; mean±S.E.M.

DETAILED DESCRIPTION OF THE INVENTION

Definitions

For convenience, certain terms employed herein are collected here. Unless otherwise defined, all technical and scientific terms used herein have the meaning commonly understood by one of skill in the art.

As used herein, "GDF11" refers to "Growth and Differentiation Factor 11," a member of the Transforming Growth Factor-beta superfamily of growth factors. GDF11 is known to bind TGFP3 superfamily type I receptors including ALK4, ALK5, and ALK7. For signaling in mammalian development, GDF11 predominantly uses ALK4 and ALK5. In a particular embodiment, GDF11 signaling can also occur via the ACVR2B receptor.

GDF11 is also closely related to GDF8 (also known as myostatin). GDF11 can also be referred to as bone morphogenetic protein 11, i.e. BMP 11. As used herein, "GDF11" can include the human precursor polypeptide (SEQ ID NO: 1, NCBI Ref Seq: NP 005802); the human pro-peptide (SEQ ID NO: 2); the human N-terminal polypeptide (SEQ ID NO: 4), and the human mature (SEQ ID NO: 3) forms of GDF11 as well as homologs from other species, including but not limited to bovine, dog, cat, chicken, murine, rat, porcine, bovine, turkey, horse, fish, baboon, and other primates. The terms also refer to fragments or variants of GDF11 that inhibit mood disorder and cognitive decline via autophagy and/or inflammation or that maintain at least 80% of the neurogenesis and angiogenesis increasing effect of the full length GDF11 of SEQ ID NO: 2, SEQ ID NO: 1, or SEQ ID NO: 3, e.g. as measured in an appropriate animal model (e.g., heterochronic parabiosis of aged mice).

In a particular embodiment, the GDF11 polypeptide is injected to a murin model and consists of the amino acid sequence (monomer): NLGLDCDEHS SESRCCRYPL TVDFEAFGWD WIIAPKRYKA NYCSGQCEYM FMQKYPHTHL VQQANPRGSA GPCCTPTKMS PINMLYFNDK QQIIYGKIPG MVVDRCGCS (https://www.peprotech.com/en/recombinant-humanmurinerat-gdf-11, SEQ ID NO:5).

As used herein, a "mood disorder" is a mental disorder characterized by alterations in mood, and including without limitation major depressive disorder (MDD) (commonly called clinical depression, unipolar depression, or major depression), bipolar disorder (BD) (formerly known as manic depression), dysthymic disorder (similar to but milder than MDD), cyclothymic disorder (similar to but milder than BD). Additional non-limiting examples of mood disorder comprise depressive disorders including atypical depression, melancholic depression, psychotic major depression, catatonic depression, postpartum depression, premenstrual dysphoric disorder, seasonal affective disorder, dysthymia, double depression, depressive disorder not otherwise specified, depressive personality disorder, recurrent brief depression, and minor depressive disorder.

As used herein, an "anxiety disorder" is a mental disorder characterized by significant feelings of anxiety and fear, and including without limitation generalized anxiety disorder, specific phobia, panic disorder, social anxiety disorder, post-traumatic stress disorder, separation anxiety disorder, situational disorder, obsessive-compulsive disorder, agoraphobia, panic disorder, and selective mutism.

The terms "decrease", "reduce", "reduced", "reduction", "decreased", and 'inhibit" are all used herein to generally mean a decrease by a statistically significant amount relative to a reference. In a preferred embodiment, a decrease is measured relative to a "healthy reference level".

The terms "increased", "increase" or "enhance" or "activate" are all used herein to generally mean an increase by a statically significant amount relative to a reference. In a preferred embodiment, an increase is measured relative to a "healthy reference level".

As used herein, a "healthy reference level" is a level measured in a control population or subject. For measured levels of GDF11, the healthy reference level in a population is the mean concentration of GDF11 protein measured in a particular defined type of sample from a group of healthy subjects used for comparison. A skilled artisan will understand that the group of healthy subjects should be chosen to have relevant defined features in common. Exemplary healthy cohorts are described in the examples below. For measured levels of GDF11, the healthy reference level in a subject may be for example the mean concentration of GDF11 protein measured in this subject when this subject does not have or is not suspected of having a mood disorder and/or an anxiety disorder used for comparison.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "sample" as used herein denotes a sample taken or isolated from a subject, e.g., cerebral tissue, cerebrospinal fluid, blood sample, plasma/serum sample, cell lysate, a homogenate of a tissue sample from a subject, or a fluid sample from a subject. Exemplary biological samples include, but are not limited to, brain and skin biopsies, cerebrospinal fluid, and blood and/or plasma/serum samples that have been collected by non-invasive means. In a particular embodiment, the sample is from a resection, biopsy, or core needle biopsy. In a particular embodiment, the sample is blood or a blood component, such as plasma. In addition, fine needle aspirate samples can be used. The term "sample" also includes untreated or pretreated (or preprocessed) samples. In a particular embodiment, the sample is an untreated sample. The sample can be obtained by removing a sample of cells and/or liquid from a subject, but can also be accomplished by using previously isolated cells and/or liquid (e.g. isolated at a prior time point and isolated by the same or another person).

As used herein, the phrase "therapeutically effective amount", "effective amount" or "effective dose" refers to an amount that provides a therapeutic benefit in the treatment, prevention, or management of a mood disorder, such as a depressive disorder or an anxiety disorder.

As used herein, "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes at least slowing of progress or worsening of symptoms that would be expected in the absence of treatment.

As used herein, the term "administering," refers to the placement of the agent or composition which increases GDF11 polypeptide levels in the subject, in particular the composition comprising a GDF11 polypeptide, as disclosed herein into a subject by a method or route which results in delivery to a site of action. The pharmaceutical composition comprising the agent, especially a GDF11 polypeptide, which increases GDF11 polypeptide levels in the subject can be administered by any appropriate route which results in an effective treatment in the subject.

As used herein, a "subject" means a human or other mammal. Usually the mammal is a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. The terms "patient", "individual" and "subject" are used interchangeably herein. The mammal can be a human, non-human primate, mouse, rat, dog, cat, horse, or cow. Mammals other than humans can be advantageously used, for example, as subjects that represent animal models of, for example, mood disorders. In addition, the methods described herein can be used to treat domesticated animals and/or pets. A subject can be male or female. A subject can be one who has been previously diagnosed with or identified as suffering from or having a condition in need of treatment (e.g., a mood disorder and/or an anxiety disorder) or one or more complications related to such a condition, but need not have already undergone treatment for a condition or the one or more complications related to the condition. Alternatively, a subject can also be one who has not been previously diagnosed as having a condition in need of treatment or one or more complications related to such a condition. Rather, a subject can include one who exhibits one or more risk factors for a condition, or one or more complications related to a condition. A "subject in need" of treatment for a particular condition can be a subject having that condition, diagnosed as having that condition, or a subject which is at increased risk of developing that condition, relative to a given reference population.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, including antigen-binding portions, which retains the essential epitope binding features of an Ig molecule. It can also be a single-domain antibody molecule named Alpaca-derived VHH nanobody. Such mutant, variant, or derivative antibody formats are known in the art.

As used herein, the terms "proteins" and "polypeptides" are used interchangeably to designate a series of amino acid residues connected to the other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when refining to a gene product and fragments thereof. Thus, exemplary polypeptides or proteins include gene products, naturally occurring proteins, homologs, orthologs, paralogs, fragments and other equivalents, variants, and analogs of the foregoing.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

The term "statistically significant" or "significantly" refers to statistical significance and generally means a "p" value less than 0.05 (calculated by the relevant statistical test). Those skilled in the art will readily appreciate that the relevant statistical test for any particular experiment depends on the type of data being analyzed. Additional definitions are provided in the text of individual sections below.

Definitions of common terms in cell biology and molecular biology can be found in "The Merck Manual of Diagnosis and Therapy", 19th Edition, published by Merck Research Laboratories, 2006 (ISBN 0-91 191 0-19-0); Roberts. Porter et al. (eds.), The Encyclopedia of Molecular Biology, published by Blackwell Science Ltd., 1994 (ISBN 0-632-021 82-9); The ELISA guidebook (Methods in molecular biology 149) by Crowther J. R. (2000); Immunology by Werner Luttmann, published by Elsevier, 2006. Definitions of common terms in molecular biology can also be found in Benjamin Lewin, Genes X, published by Jones & Bartlett Publishing, 2009 (ISBN—1 0: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001) and Davis et al., Basic Methods in Molecular Biology, Elsevier Science Publishing, Inc., New York, USA (1995) which are both incorporated by reference herein in their entireties.

Methods for Detecting GDF11 in a Subject Having or Suspected of Having a Mood Disorder and/or an Anxiety Disorder and/or for Diagnosing or Characterizing a Mood Disorder and/or an Anxiety Disorder in a Subject Provided are in vitro methods for the detection of GDF11 in a subject having or suspected of having a mood disorder and/or an anxiety disorder. The method may comprise providing a sample from a subject having or suspected of having a mood disorder and/or an anxiety disorder; contacting the sample with a GDF11-binding molecule; and detecting bound GDF11. In a particular embodiment, the mood disorder is a depressive disorder. In a preferred embodiment, the mood disorder is a major depressive disorder. In a particular embodiment, the subject has been clinically diagnosed with mood disorders and/or anxiety disorder. In a particular embodiment, the subject is undergoing treatment for the mood disorder and/or an anxiety disorder. In a particular embodiment, the subject is a human. In a particular embodiment, the subject is less than 65 years old. In a particular embodiment, the sample is plasma or serum. In a particular embodiment, the GDF11-binding molecule is an anti-GDF11 antibody or a molecule comprising an antigen-binding fragment of an anti-GDF11 antibody. In a particular embodiment, the method comprises an enzyme-linked immunosorbent assay (ELISA) or an ultrasensitive single molecule array (Simoa) technology. In a particular embodiment, the methods further comprise measuring GDF11 levels in the subject sample. In a particular embodiment, the levels of GDF11 in the sample are significantly lower than healthy reference levels. In a particular embodiment, the levels of GDF11 in the sample are not significantly lower than healthy reference levels.

In a particular embodiment, the subject is under 30, 35, 40, 45, 50, 55, 60, 65, or 70 years of age.

In a particular embodiment, the subject is one who is not suffering from a neurodegenerative disorder.

In a particular embodiment, the subject is not suffering from cognitive impairment, in particular, is not having a memory disorder nor experiencing a loss of memory.

Also provided are methods for prognosing or diagnosing or characterizing a mood disorder and/or an anxiety disorder in a subject. The methods comprise measuring GDF11 levels in the subject sample.

The method may comprise providing a sample from a subject; contacting the sample with a GDF11-binding molecule; detecting bound GDF11; and comparing the levels of detected bound GDF11 to control levels. In a particular embodiment, if the levels of GDF11 in the sample are significantly lower than healthy reference levels, the subject is diagnosed with a mood disorder and/or an anxiety disorder. In another particular embodiment, if the levels of GDF11 in the sample are significantly lower than healthy reference levels, then the subject is prognosed as at risk of developing a mood disorder and/or an anxiety disorder, or is likely to develop a mood disorder or an anxiety disorder in a short future. Conversely, if the levels of detected bound GDF11 are not significantly lower than healthy reference levels, then the subject is not diagnosed as having a mood disorder and/or an anxiety disorder, nor is he/she likely to suffer from same in a short future. In a particular embodiment, the disorder is a mood disorder. In a particular embodiment, the mood disorder is a major depressive disorder. In a particular embodiment, the subject is undergoing treatment for the mood disorder and/or an anxiety disorder. In a particular embodiment, the subject is a human. In a particular embodiment, the subject is less than 65 years old. In a particular embodiment, the sample is plasma or serum. In a particular embodiment, the GDF11-binding molecule is an anti-GDF11 antibody or a molecule comprising an antigen-binding fragment of an anti-GDF11 antibody. In a particular embodiment, the method comprises an enzyme-linked immunosorbent assay (ELISA) or an ultrasensitive single molecule array (Simoa) technology.

In a particular embodiment of these methods, the levels of detected bound GDF11 are reduced by at least 10%, 20%, 30%, 40%, 50%, 60%, 70%, 80%, 90%, or 95% in comparison to healthy reference levels. In a particular embodiment of these methods, the levels of detected bound GDF11 are reduced by from 20% to 40%, from 40% to 60%, from 60% to 80%, or from 80% to 95% in comparison to healthy reference levels.

In a particular embodiment of these methods, the healthy reference levels are 75 pg/ml, 70 pg/ml, 65 pg/ml, 60 pg/ml, 55 pg/ml, 50 pg/ml, 45 pg/ml, or 40 pg/ml. In an embodiment, the healthy reference levels are 76.40 pg/ml or higher.

In a particular embodiment of these methods, the levels of detected bound GDF11 are 10 pg/ml or 5 pg/ml. In an embodiment the detected bound GDF11 is 3.89 pg/ml or lower.

The methods may utilize GDF11 binding proteins, such as human GDF11 binding proteins, and more particularly anti-GDF11 antibodies, or antigen-binding portions thereof, that bind GDF11. Various aspects of the disclosure relate to antibodies and antibody fragments, and pharmaceutical compositions thereof.

In a particular embodiment, the GDF11 binding protein used in the diagnostic, prognostic or therapeutic methods of the invention is an antibody, which will be described now. In a particular embodiment, the GDF11 antibody is polyclonal. In a particular embodiment, the GDF11 antibody is monoclonal.

In one embodiment, polyclonal or monoclonal antibodies are generated in rabbits or mice.

In one embodiment, the GDF11 binding protein is a single-domain antibody molecule named VHH nanobody, as this type of antibody is able to cross the blood brain barrier (BBB) (Li T et al. 2016[16]. VHH antibodies are generated, for example in alpaca.

The invention encompasses a polyclonal or monoclonal antibody or fragment thereof directed against GDF11 protein. In a particular embodiment, the polyclonal or monoclonal antibody or fragment thereof specifically binds to a polypeptide comprising the amino acid sequence of at least one of SEQ ID NO: 1, SEQ ID NO:2, SEQ ID NO:3, and SEQ ID NO:4.

In one embodiment, antibodies can be obtained by immunization of an animal with a GDF11 protein as disclosed above. The antibodies can serve as reagents to bind to native GDF11 proteins of subjects in immunoassays. The invention encompasses polyclonal antibodies, monoclonal antibodies, chimeric antibodies, and fragments thereof (e.g., Fab, Fv, scFv) or VHH nanobodies directed against the GDF11 protein.

For the purposes of the present invention, the expression chimeric antibody is understood to mean, in relation to an antibody of a particular animal species or of a particular class of antibody, an antibody of said particular animal species or class of antibody comprising all or part of a heavy chain and/or of a light chain of an antibody of another animal species or of another class of antibody.

In a particular embodiment, purified proteins are used to produce antibodies by conventional techniques. In a particular embodiment, recombinant or synthetic proteins or peptides are used to produce antibodies by conventional techniques.

Antibodies can be synthetic, semi-synthetic, monoclonal, or polyclonal and can be made by techniques well known in the art. Such antibodies specifically bind to proteins and polypeptides via the antigen-binding sites of the antibody (as opposed to non-specific binding). Purified or synthetic proteins and peptides can be employed as immunogens in producing antibodies immunoreactive therewith. The proteins and peptides contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, Immuno Biology 2:14 (Garland Publishing Inc., 2nd ed. 1996). Epitopes can be identified by any of the methods known in the art. Such epitopes or variants thereof can be produced using techniques well known in the art such as solid-phase synthesis, chemical or enzymatic cleavage of a polypeptide, or using recombinant DNA technology.

Antibodies are defined to be specifically binding if they bind proteins or polypeptides with a Ka of greater than or equal to about $10^7$ $M^{-1}$. Affinities of binding partners or antibodies can be readily determined using conventional techniques, for example those described by Scatchard et al., Ann. N.Y. Acad. Sci., 51:660 (1949).

Polyclonal antibodies can be readily generated from a variety of sources, for example, horses, cows, goats, sheep, dogs, chickens, alpaca, camels, rabbits, mice, or rats, using procedures that are well known in the art. In general, a purified protein or polypeptide that is appropriately conjugated is administered to the host animal typically through parenteral injection. The immunogenicity can be enhanced through the use of an adjuvant, for example, Freund's complete or incomplete adjuvant. Following booster immunizations, small samples of serum are collected and tested for reactivity to proteins or polypeptides. Examples of various assays useful for such determination include those described in Antibodies: A Laboratory Manual, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. 4,902,614, 4,543,439, and 4,411,993; Monoclonal Antibodies, Hybridomas: A New Dimension in Biological Analyses, Plenum Press, Kennett, McKeam, and Bechtol (eds.), 1980.

For example, the host animals, such as mice, can be injected intraperitoneally at least once and preferably at least twice at about 3 week intervals with isolated and purified proteins or conjugated polypeptides, for example a peptide comprising or consisting of the specific amino acids set forth above. Mouse sera are then assayed by conventional dot blot technique or antibody capture (ABC) to determine which animal is best to fuse. Approximately two to three weeks later, the mice are given an intravenous boost of the protein or polypeptide. Mice are later sacrificed, and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as a labeled protein or polypeptide, is added to each well followed by incubation. Positive wells can be subsequently detected. Positive clones can be grown in bulk culture and supernatants are subsequently purified over a Protein A column (Pharmacia).

The monoclonal antibodies of the invention can be produced using alternative techniques, such as those described by Alting-Mees et al.[21] which is incorporated herein by reference. Similarly, binding partners can be constructed using recombinant DNA techniques to incorporate the variable regions of a gene that encodes a specific binding antibody. Such a technique is described in Larrick et al., Biotechnology, 7:394 (1989).

Antigen-binding fragments of such antibodies, which can be produced by conventional techniques, are also encompassed by the present invention. Examples of such fragments include, but are not limited to, Fab and F(ab')2 fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies can be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (Nature 332:323, 1988), Liu et al. (PNAS 84:3439, 1987), Larrick et al. (Biotechnology 7:934, 1989), and Winter and Harris (TIPS 14:139, May, 1993). Procedures to generate antibodies transgenically can be found in GB 2,272,440, U.S. Pat. Nos. 5,569,825 and 5,545,806.

Antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Publication No. WO 87/02671; Akira, et al. European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., Science 240:1041 1043, 1988; Liu et al., PNAS 84:3439 3443, 1987; Liu et al., J. Immunol. 139:3521 3526, 1987; Sun et al. PNAS 84:214 218, 1987; Nishimura et al., Canc. Res. 47:999 1005, 1987; Wood et al., Nature 314:446 449, 1985; and Shaw et al., J. Natl. Cancer Inst. 80:1553 1559, 1988); Morrison, S. L., Science 229:1202 1207, 1985; Oi et al., BioTechniques 4:214, 1986; Winter U.S. Pat. No. 5,225,539; Jones et al., Nature 321:552 525, 1986; Verhoeyan et al., Science 239:1534, 1988; and Beidler et al., J. Immunol. 141:4053 4060, 1988.

In connection with synthetic and semi-synthetic antibodies, such terms are intended to cover but are not limited to antibody fragments, isotype switched antibodies, humanized antibodies (e.g., mouse-human, human-mouse), hybrids, antibodies having plural specificities, and fully synthetic antibody-like molecules.

In one embodiment, the invention encompasses single-domain antibodies (sdAb), also known as nanobodies. A sdAb is a fragment consisting of a single monomeric variable antibody domain that can bind selectively to a specific antigen.

In one embodiment, the sdAbs are from heavy-chain antibodies found in camelids (VHH fragments), or cartilaginous fishes (VNAR fragments), or are obtained by splitting dimeric variable domains into monomers.

The antibody may be selected from polyclonal antibodies, monoclonal antibodies, fragments thereof, such as F(ab')2 and Fab fragments, single-chain variable fragments (scFvs), single-domain antibody fragments (VHHs or Nanobodies), bivalent antibody fragments (diabodies), as well as any recombinantly and synthetically produced binding partners. In a preferred embodiment, the antibody is a VHH, preferably from an alpaca.

In a particular embodiment a commercially available anti-GDF11 antibody is used. Antibodies specific for GDF11 are commercially available and may be used in embodiments of the invention disclosed herein. As of the filing date of this application several such commercial anti-GDF11 antibodies are available. Non-limiting examples include the Human GDF-11/BMP-11 Antibody, MAB19581, available from R&D systems. In a particular embodiment, the antibodies are antibodies which do not cross-react with GDF8. In a particular embodiment, the antibodies are selective GDF11 monoclonal antibodies.

In the context of the invention, GDF11 polypeptide and the levels of the GFD11 polypeptide can be detected by any means (any form of GDF11 leading to the information on GDF11 polypeptide or GDF11 levels). In a particular embodiment, the levels of the GDF11 polypeptide can thus also be determined by measuring the levels of an mRNA encoding a GDF11 polypeptide. In a particular embodiment, the levels of GDF11 can be measured as described in Souza et al.[22], which is incorporated by reference herein in its entirety.

In one embodiment, the method comprises providing a sample from a subject having or suspected of having a mood disorder; contacting the sample with a GDF11-binding molecule; and detecting bound GDF11. Generally, bound GDF11 is detected by detecting, directly or indirectly, the GDF11-binding molecule bound to the GDF11. This may be achieved, for example, by visualizing or otherwise detecting GDF11-binding molecule:GDF11 complexes. In a preferred embodiment, the GDF11-binding molecule is an anti-GDF11 antibody or antibody fragment, and antigen-antibody complexes are detected. Preferably, the method comprises an ELISA assay or an ultrasensitive single molecule array (Simoa) technology.

Preferably, the detection reagent comprises a label selected from a chemiluminescent label, an enzyme label, a fluorescence label, and a radioactive (e.g., iodine) label. Most preferably, the detection reagent is a labeled antibody or antibody fragment.

Preferred labels include a fluorescent label, such as FITC, a chromophore label, an affinity-ligand label, an enzyme label, such as alkaline phosphatase, horseradish peroxidase, or β galactosidase, an enzyme cofactor label, a hapten conjugate label, such as digoxigenin or dinitrophenyl, a Raman signal generating label, a magnetic label, a spin label, an epitope label, such as the FLAG or HA epitope, a luminescent label, a heavy atom label, a nanoparticle label, an electrochemical label, a light scattering label, a spherical shell label, semiconductor nanocrystal label, wherein the label can allow visualization with or without a secondary detection molecule.

Preferred labels include suitable enzymes such as horseradish peroxidase, alkaline phosphatase, beta-galactosidase, or acetylcholinesterase; members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, Texas Red, dichlorotriazinylamine fluorescein, dansyl chloride, phycoerythrin, fluorescent lanthanide complexes such as those including Europium and Terbium, cyanine dye family members, such as Cy3 and Cy5, molecular beacons and fluorescent derivatives thereof, as well as others known in the art; a luminescent material such as luminol; light scattering or plasmon resonant materials such as gold or silver particles or quantum dots; or radioactive material include $^{14}C$, $^{123}I$, $^{124}I$, $^{125}I$, $^{32}P$, $^{33}P$, $^{35}S$, or $^{3}H$.

In one embodiment, the antibody or an antibody fragment that binds to GDF11 binds specifically to human GDF11. In one embodiment, the antibody or an antibody fragment that binds to human GDF11 binds specifically to a polypeptide comprising or consisting of SEQ ID NO: 1, SEQ ID NO: 2, SEQ ID NO: 3, SEQ ID NO: 4, or any combination thereof.

In one embodiment, the method comprises an immunocapture method. In one embodiment, the method comprises attaching a first monoclonal or polyclonal antibody or a fragment thereof, directed against GDF11 (capture antibody), incubating the antibody with a biological sample containing GDF11 protein, and detecting the antigen-antibody complexes formed, preferably with a monoclonal antibody (visualizing antibody).

In one embodiment, the biological sample is mixed with the visualizing monoclonal antibody prior to being brought into contact with the capture antibody. A visualizing molecule may be a radioactive atom, a dye, a fluorescent molecule, a fluorophore, an enzyme; a visualizing particle may be for example: colloidal gold, a magnetic particle or a latex bead.

In one embodiment, microtiter plates can be coated by incubation overnight at 4° C. with 5 μg/ml of N proteins. Plates can be washed with 0.1% Tween 20 in PBS buffer. Serum or purified Igs can be diluted in PBS containing 0.5% gelatin and 0.1% Tween. After 1 h incubation at 37° C., plates can be washed again. The bound antibodies can be detected by adding rabbit polyclonal anti-IgGs (obtained by immunizing rabbits with IgGs isolated on protein A and protein G columns) followed by Alkaline Phosphatase labeled goat anti-rabbit immunoglobulins. Enzymatic activity can be quantified using pNPP (para-NitroPhenylPhosphate, SigmaAldrich) substrate according to the manufacturers protocol.

In a particular embodiment, the levels of GDF11 polypeptide are the levels of GDF11 in the systemic circulation of a subject. In a preferred embodiment, the levels of GDF11 in the systemic circulation of a subject are determined by a method comprising obtaining a serum sample of a subject and determining the levels of GDF11 in the serum sample. In a particular embodiment, the levels of GDF11 polypeptide are the levels of GDF11 in the cerebral vasculature of a subject. In a preferred embodiment, the levels of GDF11 in the systemic circulation of a subject are determined by a method comprising obtaining a plasma sample of a subject and determining the levels of GDF11 in the plasma sample. In a preferred embodiment, the levels of GDF11 in the systemic circulation of a subject are determined by a method comprising obtaining a platelet-rich plasma sample of a subject and determining the levels of GDF11 in the platelet-rich plasma sample. In a particular embodiment, the levels of GDF11 polypeptide are the levels of GDF11 in the neurovasculature of a subject. In a particular embodiment, the levels of GDF11 polypeptide are the levels of GDF11 in the cerebral tissue of a subject. In a particular embodiment, the levels of GDF11 polypeptide are the levels of GDF11 in the cerebrospinal fluid of a subject. In a particular embodiment, the levels of GDF11 polypeptide are the levels of GDF11 in the lateral ventricles of a subject. In a particular embodiment, the levels of GDF11 polypeptide are the levels of GDF11 in the subventricular zone neurovascular niche of a subject.

In a particular embodiment, levels of GDF11 in a subject are determined. Levels may be determined by obtaining a sample from the subject and determining the levels of GDF11 in the sample. Methods for determining the levels of a polypeptide in a subject or a sample obtained from a subject are well known in the art and include, but are not limited to, ELISA, radioimmunoassay, immunohistochemistry, methods involving a labeled antibody specific for GDF11, dot blot analysis, functional bioassays, Northern blot, in-situ hybridization, and RT-PCR, aptamer-based proteomic technology (e.g., SOMAscan™ commercially available from SomaLogic, Inc.), western blot, flow cytometry, bead-based immunoassay such as Luminex technology, or ultrasensitive single molecule array (Simoa) technology, among others.

Methods of Treating or Preventing a Mood and/or Anxiety Disorder and Optionally Accelerated Aging In another aspect, this invention provides a method of treating or preventing a mood and/or anxiety disorder, and optionally the accelerated aging associated therewith, in a subject in need thereof, comprising administering to the subject an agent or composition which increases the levels of GDF11 polypeptide in the subject. Said composition contains advantageously agents that can increase the levels and/or activity of GDF11 (such as agonist antibodies). In a particular embodiment, the mood disorder is a depressive disorder or an anxiety disorder. In a particular embodiment, the disorder is a major depressive disorder. In a particular embodiment, the agent or composition comprises an agonist antibody that increases levels of GDF11. In a particular embodiment, the agent or composition comprises a GDF11 polypeptide or a functional fragment or variant thereof. In a particular embodiment, the GDF11 polypeptide comprises or consists of the amino acid sequence of SEQ ID NO:1, SEQ ID NO:2, or SEQ ID NO:3. In a particular embodiment, the agent or composition comprises homodimers of GDF11 polypeptides comprising the amino acid sequence of any of SEQ ID Nos: 1, 2, or 3. In a particular embodiment, the agent or composition comprises complexes of GDF11 polypeptides comprising the amino acid sequence of at least one of SEQ ID NOS: 1, 2, or 3. In a particular embodiment, the functional variant is as disclosed in WO2019/144053. In a particular embodiment, the agent or composition comprises a nucleic acid encoding a GDF11 polypeptide or a functional fragment or variant thereof. In a particular embodiment, the GDF11 polypeptide comprises a modified GDF11 polypeptide. In a particular embodiment, the modified GDF11 polypeptide comprises a modification selected from the group consisting of fusion to an Fc fragment, PEGylation, conjugation to albumin, an amino acid mutation that prevents or reduces proteolytic degradation, an amino acid mutation that prolongs half-life, and any combination thereof. In a particular embodiment, the composition is administered via a route selected from the group consisting of intravenously, subcutaneously, intra-arterially, and intra-muscularly. In a particular embodiment, GDF11 polypeptide levels are increased by at least 25%, 50%, 75% or 100% of healthy reference levels. In a particular embodiment, the subject does not suffer from a neurodegenerative disorder. In another particular embodiment, the subject does not suffer from a cognitive impairment or decline, in particular, is not having a memory disorder nor experiencing a loss of memory. In a particular embodiment, the subject being treated was prognosed to suffer from a mood disorder or an anxiety disorder prior to administering the agent or composition of the invention. In this way, the onset of said disorders could be prevented or at least delayed. In a particular embodiment, the subject being treated is diagnosed with the mood disorder or the anxiety disorder by a method of the invention prior to administering the agent or composition to the subject. In a particular embodiment, the effectiveness of the treatment or prevention is characterized by a method of the invention.

In another aspect, this invention provides a method of treating or preventing an accelerated aging in a subject in need thereof, comprising administering to the subject an agent or composition which increases the levels of GDF11 polypeptide in the subject. In a particular embodiment, the agent or composition comprises an agonist antibody that increases levels of GDF11. In a particular embodiment, the agent or composition comprises a GDF11 polypeptide or a functional fragment or variant thereof. In a particular embodiment, the GDF11 polypeptide comprises or consists of the amino acid sequence of SEQ ID NO:1, SEQ ID NO:2, or SEQ ID NO:3. In a particular embodiment, the agent or composition comprises homodimers of GDF11 polypeptides comprising the amino acid sequence of any of SEQ ID NOs: 1, 2, or 3. In a particular embodiment, the agent or composition comprises complexes of GDF11 polypeptides comprising the amino acid sequence of at least one of SEQ ID NOS: 1, 2, or 3. In a particular embodiment, the functional variant is as described in WO2019/144053. In a particular embodiment, the agent or composition comprises a nucleic acid encoding a GDF11 polypeptide or a functional fragment or variant thereof. In a particular embodiment, the GDF11 polypeptide comprises a modified GDF11 polypeptide. In a particular embodiment, the modified GDF11 polypeptide comprises a modification selected from the group consisting of fusion to an Fc fragment, PEGylation, conjugation to albumin, an amino acid mutation that prevents or reduces proteolytic degradation, an amino acid mutation that prolongs half-life, and any combination thereof. In a particular embodiment, the composition is administered via a route selected from the group consisting of intravenously, subcutaneously, intra-arterially, and intra-muscularly. In a particular embodiment, GDF11 polypeptide levels are increased by at least 25%, 50%, 75% or 100% of healthy reference levels. In a particular embodiment, the subject does not suffer from a neurodegenerative disorder. In another particular embodiment, the subject does not suffer from a cognitive impairment or decline, in particular, is not having a memory disorder or experiencing a loss of memory. In a particular embodiment, the subject being treated was prognosed to suffer from a mood disorder or an anxiety disorder prior to administering the agent or composition of the invention. In this way, the onset of said disorders could be prevented or at least delayed. In a particular embodiment, the subject being treated is diagnosed with the mood or anxiety disorder by a method of the invention prior to administering the agent or composition to the subject. In a particular embodiment, the effectiveness of the treatment or prevention is characterized by a method of the invention.

In a particular embodiment, the methods comprise administering to a subject an agent or a composition which increases the levels of GDF11 polypeptide in the subject.

In a particular embodiment, the agent or composition increases the levels of GDF11 polypeptide in at least one of the subject's systemic circulation, cerebral vasculature, cerebrospinal fluid, cerebral tissue, lateral ventricles, neurovasculature, and subventricular zone neurovascular niche.

In a particular embodiment, the subject is one in need of treatment or prevention of a mood and/or anxiety disorder.

In a particular embodiment, the subject is one who has been prognosed or diagnosed as having a mood and/or anxiety disorder by a medical professional.

In a particular embodiment, the mood disorder is a depressive disorder. In a particular embodiment, the mood disorder is selected from the group consisting of major depressive disorder (MDD) (commonly called clinical depression, unipolar depression, or major depression), bipolar disorder (BD) (formerly known as manic depression), dysthymic disorder (similar to but milder than MDD), cyclothymic disorder (similar to but milder than BD), atypical depression, melancholic depression, psychotic major depression, catatonic depression, postpartum depression, premenstrual dysphoric disorder, seasonal affective disorder, dysthymia, double depression, depressive disorder not otherwise specified, depressive personality disorder, recurrent brief depression, and minor depressive disorder. In a preferred embodiment, the mood disorder is MDD.

In a particular embodiment, the depressive disorder is an age-related depression.

In a particular embodiment, the disorder is an anxiety disorder. In a particular embodiment, the anxiety disorder is selected from the group consisting of generalized anxiety disorder, specific phobia, panic disorder, social anxiety disorder, post-traumatic stress disorder, separation anxiety disorder, situational disorder, obsessive-compulsive disorder, agoraphobia, panic disorder, and selective mutism.

In a particular embodiment, the subject is under 30, 35, 40, 45, 50, 55, 60, 65, or 70 years of age.

In a particular embodiment, the subject is one who is not suffering from a neurodegenerative disorder.

In a particular embodiment, the subject is not suffering from cognitive impairment or decline, in particular, is not having a memory disorder nor experiencing a loss of memory.

In a particular embodiment, the subject is one who is not exhibiting symptoms of a neurodegenerative disorder, wherein the symptoms comprise or consist of at least one of difficulty lifting the front part of the foot and toes; weakness in arms, legs, feet, or ankles; hand weakness or clumsiness; slurring of speech; difficulty swallowing; muscle cramps; twitching in arms, shoulders, and tongue; difficulty chewing; difficulty breathing; muscle paralysis; partial or complete loss of vision; double vision; tingling or pain in parts of body; electric shock sensations that occur with head movements; tremor; unsteady gait; fatigue; dizziness; loss of memory; disorientation; misinterpretation of spatial relationships; difficulty reading or writing; difficulty concentrating and thinking; difficulty making judgments and decisions; difficulty planning and performing familiar tasks; depression; anxiety; social withdrawal; mood swings; irritability; aggressiveness; changes in sleeping habits; wandering; dementia; loss of automatic movements; impaired posture and balance; rigid muscles; bradykinesia; slow or abnormal eye movements; involuntary jerking or writhing movements (chorea); involuntary, sustained contracture of muscles (dystonia); lack of flexibility; lack of impulse control; changes in appetite; and all possible combinations thereof.

In a particular embodiment, the subject has not been diagnosed with a neurological injury or damage to the CNS or the PNS associated with physical injury, ischemia, certain medical procedures or exposure to biological or chemical toxins or poisons, tumors, infections, metabolic or nutritional disorders, cognition or mood disorders, and various medical conditions associated with neural damage or destruction.

In a particular embodiment, the subject has not been diagnosed with a neurovascular disorder. In a particular embodiment, the subject does not exhibit hypertension, platelet aggregation, altered cerebrovascular architecture (e.g., narrowing, stiffness, deformation), sudden blood pressure shifts, facial weakness, visual impairment, loss of coordination, or balance, a sudden headache, and mental confusion with unintelligible speech.

The methods and compositions described herein relate to increasing the levels of GDF11 polypeptide in a subject. In a particular embodiment, this is achieved by administering a GDF11 polypeptide or a functional fragment or variant thereof to a subject. The GDF11 polypeptide may be selected from the human precursor polypeptide (SEQ ID NO: 1, NCBI Ref Seq: NP 005802); the human pro-peptide (SEQ ID NO: 2), and the human mature (SEQ ID NO: 3) forms of GDF11 as well as homologs from other species, including but not limited to bovine, dog, cat, chicken, murine, rat, porcine, bovine, turkey, horse, fish, baboon and other primates. In a particular embodiment, the administered peptide is a fragment or variant of GDF11 that inhibit mood disorder and cognitive decline via autophagy and/or inflammation or that maintain at least 80% of the neurogenesis and angiogenesis increasing effect of the full length GDF11 of SEQ ID NO: 2, SEQ ID NO: 1, or SEQ ID NO: 3, e.g. as measured in an appropriate animal model (e.g., heterochronic parabiosis of aged mice).

Conservative substitution variants that inhibit mood disorder and cognitive decline via autophagy and/or inflammation or that maintain any of the neural stem cell and/or progenitor cell rejuvenating effect, the neurogenesis effect, or the angiogenesis effect of wild type GDF11 will include a conservative substitution as defined herein. The identification of amino acids most likely to be tolerant of conservative substitution while maintaining at least 80% of the activity of the wild type GDF11 is guided by, for example, sequence alignment with GDF11 homologs or paralogs from other species. Amino acids that are identical between GDF11 homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants can be tested for activity, for example, by administering the variant to an appropriate animal model (e.g., aged mice).

For human GDF11, the pro-peptide plus signal sequence (e.g. the precursor polypeptide, e.g., SEQ ID NO: 1) is 407 amino acids long. Cleavage of the 24 amino acid signal peptide generates a pro-peptide (e.g., SEQ ID NO: 2) of 383 amino acids and cleavage of the pro-peptide results in a mature GDF11 polypeptide (e.g., SEQ ID NO: 3) of 109 amino acids that corresponds to the C-terminal of the pro-peptide. The mature polypeptide forms a disulfide-linked homodimer. Cleavage of the pro-peptide also generates the N-terminal polypeptide (e.g., SEQ ID NO: 4) comprising amino acids 25-298 of SEQ ID NO: 1. The N-terminal GDF11 polypeptide can antagonize the activity of, e.g., the polypeptides of SEQ ID NOs: 2 and 3, at least in vitro by forming a complex with other forms of GDF11 polypeptides and can thus be used to modulate the activity of GDF11 compositions as described herein. Thus, to the extent that GDF11 polypeptides as described herein treat or prevent a mood and/or anxiety disorder, and to the extent the N-terminal GDF11 polypeptide of, e.g., SEQ ID NO: 4, can antagonize such effects, the polypeptide of SEQ ID NO: 4 can be excluded from the meaning of "GDF11 polypeptide" as that term is used herein (i.e., for the treating methods of the invention).

As used herein, "pro-peptide" used in reference to GDF11 refers to a GDF11 polypeptide in which the signal domain (e.g. amino acids 1-24 of SEQ ID NO:1) has been cleaved off during formation of the mature and/or active forms of GDF11. As used herein, "precursor peptide" used in reference to GDF11 refers to a GDF11 polypeptide comprising the signal domain, e.g., a polypeptide comprising the amino acid sequence of SEQ ID NO:1.

In a particular embodiment, the levels of GDF11 in a subject are increased by administering an agent or composition comprising a GDF11 agonist that increases the levels or activity of GDF11 in the subject. Exemplary GDF11 agonists are described in U.S. Pat. No. 8,323,964.

In a particular embodiment, levels of GDF11 in a subject are increased by administering an agent or composition comprising an agonist antibody that increases levels of GDF11 in the subject. Any antibody that is capable of increasing expression of GDF11 in the subject can be used. As used herein "antibody" includes, but is not limited to, full length antibodies, antibody fragments, single chain antibodies, bispecific antibodies, minibodies, domain antibodies, VHH/nanobodies, synthetic antibodies (sometimes referred to herein as "antibody mimetics"), chimeric antibodies, humanized antibodies, antibody fusions (sometimes referred to as "antibody conjugates"), and fragments of each, respectively. Exemplary antibody fragments include, but are not limited to, (i) the Fab fragment consisting of VL, VH, CL and CH I domains, (ii) the Fd fragment consisting of the VH and CHI domains, (iii) the Fv fragment consisting of the VL and VH domains of a single antibody, (iv) the dAb fragment, which consists of a single variable domain, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulfide bridges linking the VH and VL domains. Examples of antibody formats and architectures are described in Holliger & Hudson[23], 2006, Nature Biotechnology 23(9): 1 126-1 136, and Carter[24] 2006, Nature Reviews Immunology 6:343-357 and references cited therein, all expressly incorporated by reference. Exemplary GDF11 agonist antibodies include the GDF11 agonist antibodies described in PCT International Application Publication WO2002/010214.

In a particular embodiment, the levels of GDF11 in a subject are increased by administering an agent or composition comprising a GDF11 polypeptide and/or a nucleic acid encoding a GDF11 polypeptide. A GDF11 polypeptide administered to a subject according to the methods described herein can comprise a GDF11 polypeptide as described herein above, e.g. a pro-peptide or mature form. In a particular embodiment, the GDF11 polypeptide comprises the amino acid sequence of SEQ ID NO: 1. In a particular embodiment, the GDF11 polypeptide comprises the amino acid sequence of SEQ ID NO: 2. In a particular embodiment, the GDF11 polypeptide comprises the amino acid sequence of SEQ ID NO: 3.

In a particular embodiment, the agent or composition administered to the subject can comprise GDF11 polypeptide homodimers comprising polypeptides of the amino acid sequence of SEQ ID NO: 3. In a particular embodiment, the agent or composition administered to the subject can comprise GDF11 polypeptide homodimers comprising polypeptides of the amino acid sequence of SEQ ID NO: 2. In a particular embodiment, the agent or composition administered to the subject can comprise GDF11 polypeptide homodimers comprising polypeptides of the amino acid sequence of SEQ ID NO: 1. In a particular embodiment, the agent or composition administered to the subject can comprise GDF11 polypeptide heterodimers comprising polypeptides of any of the amino acid sequence of SEQ ID NO: 3, SEQ ID NO: 2, and/or SEQ ID NO: 1.

In a particular embodiment, a functional variant or fragment of a GDF11 polypeptide can be administered to a subject. In a particular embodiment, the variant of GDF11 is a conservatively modified variant. In a particular embodiment of any of the aspects described herein, the subject can be administered a variant or fragment (e.g. a conservatively modified variant or a functional fragment or a nucleic acid encoding such a polypeptide). Examples of variants includes the variants described in WO2019/144053.

In a particular embodiment, the GDF11 polypeptide can be a variant of a sequence described herein, e.g. a variant of a GDF11 polypeptide comprising the amino acid sequence of SEQ ID NO: 3, SEQ ID NO: 1, or SEQ ID NO: 2. In a particular embodiment, the variant is a conservative substitution variant. Variants can be obtained by mutations of native nucleotide sequences, for example. A "variant", as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encodes a variant protein or fragment thereof that retains the relevant biological activity relative to the reference protein, i.e., can inhibit mood disorder and cognitive decline via autophagy and/or inflammation or can rejuvenate neural stem cells and/or progenitor cells at least 50% as well as wild type GDF11. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of wild type GDF11, e.g. 110%, 125%, 150%, 175%, 200%, or more.

One method of identifying amino acid residues which can be substituted is to align, for example, human GDF11 to a GDF11 homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. Similarly, alignment with a related polypeptide from the same species, e.g. GDF8, which does not show the same activity, can also provide guidance with respect to regions or structures required for GDF11 activity. The variant amino acid or DNA sequence can be at least 90%, at least 95%, at least 96%, at least 97%, at least 98%, at least 99%, or more, identical to a native or reference sequence, e.g. SEQ ID NO: 3, SEQ ID NO: 1, or SEQ ID NO: 2 or a nucleic acid encoding one of those amino acid sequences. The degree of homology (percent identity) between a native and a mutant sequence can be determined, for example, by comparing the two sequences using freely available computer programs commonly employed for this purpose on the World Wide Web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide web at http://blast.ncbi.nlm.nih.gov), with default parameters set.

It is noted that the mature GDF11 polypeptide includes likely intrachain disulfide bonds between, e.g. amino acid 313 and 372; 341 and 404; and 345 and 406 (numbered relative to the full length polypeptide, including the signal sequence) and that amino acid 371 likely participates in interchain disulfide bonding.

A given amino acid can be replaced by a residue having similar physicochemical characteristics, e.g., substituting one aliphatic residue for another (such as Ile, Val, Leu, or Ala for one another), or substitution of one polar residue for another (such as between Lys and Arg; Glu and Asp; or Gin and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically, conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In a particular embodiment, the GDF11 polypeptide administered to a subject can comprise one or more amino acid substitutions or modifications. In a particular embodiment, the substitutions and/or modifications can prevent or reduce proteolytic degradation and/or prolong half-life of the polypeptide in the subject. In a particular embodiment, a GDF11 polypeptide can be modified by conjugating or fusing it to other polypeptide or polypeptide domains such as, by way of non-limiting example, transferrin (WO06096515), albumin (Yeh et al., 1992), growth hormone (US2003104578); cellulose (Levy and Shoseyov, 2002); and/or Fc fragments (Ashkenazi and Chamow, 1997).

In a particular embodiment, a GDF11 polypeptide as described herein can comprise at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta (aminoalkyl)-phenylacetic acid, thioamide, tetrazole, boronic ester, olefinic group, and derivatives thereof.

In a particular embodiment, a GDF11 polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gin (Q), Asp (D), Glu (E), Lys (K), Arg (R), and His (H). In a particular embodiment, a GDF11 polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mereapto-D-valine), ornithine, citruline, alpha-methyl-alanine, parabenzoylphenylalanine, para-amino phenylalanine, p-fluorophenylalanine, phenylglycine, propargylglycine, sarcosine, and tert-butylglycine), diaminobutyric acid, 7-hydroxytetrahydroisoquinoline carboxylic acid, naphthylalanine, biphenylalanine, cyclohexylalanine, aminoisobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-lcyclopentanecarboxylic acid, 1-amino-1-cyclohexanecarboxylic acid, amino-benzoic acid, aminonaphthoic acid, gamma-aminobutyric acid, difluorophenylalanine, nipecotic acid, alpha-anlino butyric acid, thienyl-alanine, t-butylglycine, trifluorovaline; hexafluoroleucine; fluorinated analogs; azidemodified amino acids; alkyne-modified amino acids; cyano-modified amino acids; and derivatives thereof.

In a particular embodiment, a GDF11 polypeptide can be modified, e.g. by addition of a moiety to one or more of the amino acids comprised in the peptide. In a particular embodiment, a GDF11 polypeptide as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In a particular embodiment, a GDF11 polypeptide as described herein can comprise one or more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In a particular embodiment, an end-capping modification can comprise acetylation at the N-terminus, N-terminal acylation, and N-terminal formylation. In a particular embodiment, an end-capping modification can comprise amidation at the C terminus, introduction of C-terminal alcohol, aldehyde, ester, and thioester moieties. The half-life of a GDF11 polypeptide can be increased by the addition of moieties, e.g. PEG or albumin.

In a particular embodiment, the GDF11 polypeptide administered to the subject can be a functional fragment of one of the GDF11 amino acid sequences described herein. As used herein, a "functional fragment" is a fragment or segment of a peptide which can inhibit mood disorder and cognitive decline via autophagy and/or inflammation or can rejuvenate neural stem cells and/or progenitor cells or increase neurogenesis in a subject in accordance with the work described herein. A functional fragment can comprise conservative substitutions of the sequences disclosed herein. In a particular embodiment, a functional fragment can comprise the 12.5 kDa C-terminus of GDF11. In a particular embodiment, the 12.5 kDa C-terminus of GDF11 (e.g., SEQ ID NO:3) can function as a monomer. In a particular embodiment, the 12.5 kDa C-terminus of GDF11 can function as a homodimer. In a particular embodiment, the 12.5 kDa C-terminus of GDF11 can function as a heterodimer with the GDF11 pro-peptide.

Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42: 133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. In a particular embodiment, a GDF11 polypeptide as described herein can be chemically synthesized and mutations can be incorporated as part of the chemical synthesis process.

In a particular embodiment, a GDF11 polypeptide as described herein can be formulated as a pharmaceutically acceptable prodrug. As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See: Design of Prodrugs, H. Bundgaard, Elsevier (1985); Wang et al. "Prodrug approaches to the improved delivery of peptide drug" in Curr. Pharm. Design. 5(4):265-287 (1999); Pauletti et al. (1997) Improvement in peptide bioavailability: Peptidomimetics and Prodrug Strategies, Adv. Drug. Delivery Rev. 27:235-256.

In a particular embodiment, a GDF11 polypeptide as described herein can be a pharmaceutically acceptable solvate. The term "solvate" refers to a peptide as described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The peptides of the present invention can be synthesized by using well known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 2d Ed, Vols 1 to 8, Cold Spring Harbor, N.Y. (1989); M. W. Pennington and B. M. Dunn, Methods in Molecular Biology: Peptide Synthesis Protocols, Vol 35, Hurnana Press, Totawa, N.J. (1994), contents of both of which are herein incorporated by reference. Peptides can also be chemically synthesized using methods well known in the art, see e.g. in N. L. Benoiton, Chemistry of Peptide Synthesis, CRC Press, Boca Raton, FL (2005).

In a particular embodiment, the levels of GDF11 in the subject are increased by at least 20% over the levels of GDF11 in the subject prior to treatment, e.g. 20% or more, 30% or more, 40% or more, 50% or more, 100% or more, 150% or more, 200% or more, 250% or more, 300% or more, or 350% or more. In a particular embodiment, the levels of GDF11 in the subject are increased by at least 100% over the levels of GDF11 in the subject prior to treatment. In a particular embodiment, the levels of GDF11 in the subject are increased by at least 200% over the levels of GDF11 in the subject prior to treatment. In a particular embodiment, the levels of GDF11 in the subject are increased by about 250% over the levels of GDF11 in the subject prior to treatment. In a particular embodiment, the levels of GDF11 in the subject are increased to at least 50% of healthy reference levels, e.g. 50% or more, 60% or more, 70% or more, 80% or more, 90% or more, or 100% or more of healthy reference levels. In a particular embodiment, the levels of GDF11 in the subject are increased to at least 60% of healthy reference levels. In a particular embodiment, the levels of GDF11 in the subject are increased to at least 75% of healthy reference levels. In a particular embodiment, the levels of GDF11 in the subject are increased to at least 90% of healthy reference levels.

In a particular embodiment, healthy reference levels can be the average levels of GDF11 in a population of human subjects not exhibiting any signs or symptoms of a mood or anxiety disorder. In a particular embodiment, the human subjects are under the age of 30, 35, 40, 45, 50, 55, 60, 65, or 70 years of age. In a particular embodiment, the human reference subjects are not suffering from a neurodegenerative disorder. In another particular embodiment, the human reference subjects do not suffer from a cognitive impairment or decline, in particular, are not having a memory disorder nor experiencing a loss of memory.

In a particular embodiment, healthy reference levels can be the average levels of GDF11 in a population of human subjects not exhibiting any signs or symptoms of a mood or anxiety disorder and who are under the age of 70.

In a particular embodiment, healthy reference levels can be the average levels of GDF11 in a population of human subjects not exhibiting any signs or symptoms of a mood or anxiety disorder and who are under the age of 65.

In a particular embodiment, healthy reference levels can be the average levels of GDF11 in a population of human subjects not exhibiting any signs or symptoms of a mood or anxiety disorder and who are under the age of 60. In a particular embodiment, healthy reference levels can be the average levels of GDF11 in a population of human subjects not exhibiting any signs or symptoms of a mood or anxiety disorder and who are under the age of 55. In a particular embodiment, healthy reference levels can be the average levels of GDF11 in a population of human subjects not exhibiting any signs or symptoms of a mood or anxiety disorder and who are under the age of 50. In a particular embodiment, healthy reference levels can be the average levels of GDF11 in a population of human subjects not exhibiting any signs or symptoms of a mood or anxiety disorder and who are under the age of 45. In a particular embodiment, healthy reference levels can be the average levels of GDF11 in a population of human subjects not exhibiting any signs or symptoms of a mood or anxiety disorder and who are under the age of 40. In a particular embodiment, healthy reference levels can be the average levels of GDF11 in a population of human subjects not exhibiting any signs or symptoms of a mood or anxiety disorder and who are under the age of 35. In a particular embodiment, healthy reference levels can be the average levels of GDF11 in a population of human subjects not exhibiting any signs or symptoms of a mood or anxiety disorder and who are under the age of 30. In a particular embodiment, healthy reference levels can be the average levels of GDF11 in a population of human subjects not exhibiting any signs or symptoms of a mood or anxiety disorder and who are under the age of 25. In a particular embodiment, healthy reference levels can be the average levels of GDF11 in a population of human subjects not exhibiting any signs or symptoms of a mood or anxiety disorder and who are under the age of 20.

In a particular embodiment, the methods described herein can comprise selecting a subject with levels of GDF11 lower than healthy reference levels and administering a treatment as described herein.

In a particular embodiment, the levels of GDF11 in a subject are increased in order to treat a mood disorder and/or an anxiety disorder in a subject.

In another aspect, the present invention provides a method for treating or preventing a mood disorder and/or an anxiety disorder, as well as reversing accelerated aging in a subject, comprising administering to the subject an effective amount of an agent or composition which increases the levels of GDF11 polypeptide in the subject, thereby treating the mood disorder and/or an anxiety disorder in the subject.

Aspects of the technology described herein relate to agents and compositions of the invention, which increase levels of GDF11 polypeptide (e.g., compositions comprising a GDF11 polypeptide as described herein or a nucleic acid encoding a GDF11 polypeptide as described herein). In a particular embodiment, the composition is a pharmaceutical composition. As used herein, the term "pharmaceutical composition" a composition containing the active agent of the invention (which increases levels of GDF11 polypeptide) in combination with a pharmaceutically acceptable carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A still further aspect of the invention provides a pharmaceutical composition according to the invention, containing the agent of the invention, for use for treating or preventing a mood disorder or an anxiety disorder in a subject in need thereof. Said pharmaceutical composition or agent can also be used for treating or preventing accelerated aging in a subject suffering from mood disorder or from anxiety disorder.

In a particular embodiment, the mood disorder is a depressive disorder, preferably an age-related depression.

The present invention also provides an agent of the invention (which increases levels of GDF11 polypeptide) for the preparation of a medicament intended to be administered to patients suffering from mood disorder or an anxiety disorder, in particular to reverse accelerated aging in said subject.

The preparation of a pharmacological composition that contains active ingredients dissolved or dispersed therein is well understood in the art and generally need not be limited based on formulation. Typically such compositions are prepared as injectable either as liquid solutions or suspensions, however, solid forms suitable for solution, or suspension, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents, and the like which enhance the effectiveness of the active ingredient. The therapeutic composition of the present invention can include pharmaceutically acceptable salts of the components therein.

Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine, and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline.

Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In a particular embodiment, the agents and compositions of the invention, which increase levels of GDF11 polypeptide, especially a GDF11 polypeptide or nucleic acid encoding a GDF11 polypeptide as described herein, can be administered by controlled- or delayed-release means. Controlled release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled-release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like.

Advantageously, controlled-release formulations can be used to control a drug's onset of action, duration of action, plasma levels within the therapeutic window, and peak blood levels. In particular, controlled or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B 1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS© (Alza Corporation, Mountain View, Calif., USA)), or a combination thereof to provide the desired release profile in varying proportions.

In a particular embodiment, the technology described herein relates to a syringe comprising a therapeutically effective amount of a composition e.g. a pharmaceutical preparation comprising an agent and of the invention, especially a GDF11 polypeptide, which increases levels of GDF11 polypeptide as described herein.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

In one aspect, the technology described herein relates to a method comprising administering an agent which increases levels of GDF11 polypeptide, especially a GDF11 polypeptide or a nucleic acid encoding a GDF11 polypeptide, to a subject. In a particular embodiment, the subject is in need of treatment for a mood disorder and/or for an anxiety disorder.

Administration may be via the intravenously, intranasally, intraarterially, orally, by inhalation, intraperitoneally, intramuscularly, subcutaneously, intracavity, or by other means known by those skilled in the art. The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The dosage ranges for the agent depends upon the potency, and are amounts large enough to produce the desired effect e.g., reducing or eliminating a mood or anxiety disorder in a subject. The dosage should not be so large as to cause unacceptable adverse side effects.

Generally, the dosage will vary with the age, condition, and sex of the patient and can be determined by one of skill in the art. The dosage can also be adjusted by the individual physician in the event of any complication. Typically, the dosage can range from 0.001 mg/kg body weight to 0.5 mg/kg body weight. In one embodiment, the dose range is from 5 ng/kg body weight to 30 μg/kg body weight.

Administration of the doses recited above can be repeated. In a particular embodiment, the doses are given once a day, or multiple times a day, for example, but not limited to, three times a day. In a particular embodiment, the doses recited above are administered daily for weeks or months. The duration of treatment depends upon the subject's clinical progress and responsiveness to therapy. Without wishing to be bound by theory, the data reported herein demonstrate that in certain embodiments treatment may be effective at reducing or eliminating a mood or anxiety disorder in a subject after cessation of treatment for a period of at least one week, two weeks, one month, two months, three months, six months or longer.

Precise amounts of the active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent administration. Alternatively, continuous intravenous infusions sufficient to maintain concentrations in the blood in the ranges specified for in vivo therapies are contemplated. In a particular embodiment, the dosage range is sufficient to maintain concentrations in the blood in the range found in the blood of a population of normal, healthy human subjects (e.g. those with no signs, symptoms, or markers of mood disorders and/or anxiety) under the age of 70. In a particular embodiment, the dosage range is sufficient to maintain concentrations in the blood in the range found in normal, healthy human subjects under the age of 65. In a particular embodiment, the dosage range is sufficient to maintain concentrations in the blood in the range found in normal, healthy human subjects under the age of 60. In a particular embodiment, the dosage range is sufficient to maintain concentrations in the blood in the range found in normal, healthy human subjects under the age of 55. In a particular embodiment, the dosage range is sufficient to maintain concentrations in the blood in the range found in normal, healthy human subjects under the age of 50. In a particular embodiment, the dosage range is sufficient to maintain concentrations in the blood in the range found in normal, healthy human subjects under the age of 45. In a particular embodiment, the dosage range is sufficient to maintain concentrations in the blood in the range found in normal, healthy human subjects under the age of 40. In a particular embodiment, the dosage range is sufficient to maintain concentrations in the blood in the range found in normal, healthy human subjects under the age of 35. In a particular embodiment, the dosage range is sufficient to maintain concentrations in the blood in the range found in normal, healthy human subjects under the age of 30. In a particular embodiment, the dosage range is sufficient to maintain concentrations in the blood in the range found in normal, healthy human subjects under the age of 25.

A therapeutically effective amount is an amount of an agent that is sufficient to produce a statistically significant, measurable change in, for example, a mood or anxiety disorder. In addition, efficacy of an agent can be measured by an increase in GDF11 polypeptides or fragments thereof in a subject being treated with an agent which increases GDF11 levels, especially a GDF11 polypeptide.

In a particular embodiment, the agent or composition comprises an agonist antibody that increases expression of GDF11. In a particular embodiment, the agent or composition binds to, activates or signals through receptors such as the ALK4/5. In a particular embodiment, the agent or composition comprises a GDF11 polypeptide. In a particular embodiment, the agent or composition comprises a GDF11 polypeptide comprising the amino acid sequence of SEQ ID NO: 1. In a particular embodiment, the agent or composition comprises a GDF11 polypeptide comprising the amino acid sequence of SEQ ID NO: 2. In a particular embodiment, the agent or composition comprises a GDF11 polypeptide comprising the amino acid sequence of SEQ ID NO: 3.

In a particular embodiment, the agent or composition comprises a GDF11 polypeptide comprising an amino acid sequence at least 80%, 85%, 90%, or 95% identical to the amino acid sequence of SEQ ID NO: 1. In a particular embodiment, the agent or composition comprises a GDF11 polypeptide comprising an amino acid sequence at least 80%, 85%, 90%, or 95% identical to the amino acid sequence of SEQ ID NO: 2. In a particular embodiment, the agent or composition comprises a GDF11 polypeptide comprising an amino acid sequence at least 80%, 85%, 90%, or 95% identical to the amino acid sequence of SEQ ID NO: 3.

In a particular embodiment, the agent or composition comprises a GDF11 polypeptide consisting of the amino acid sequence of SEQ ID NO: 1. In a particular embodiment, the agent or composition comprises a GDF11 polypeptide consisting of the amino acid sequence of SEQ ID NO: 2. In a particular embodiment, the agent or composition comprises a GDF11 polypeptide consisting of the amino acid sequence of SEQ ID NO: 3.

In a particular embodiment, the agent or composition comprises homodimers of GDF11 polypeptides comprising the amino acid sequence of any of SEQ ID NOs: 1, 2, 3 or 4. In a particular embodiment, the agent or composition comprises complexes of GDF11 polypeptides comprising the amino acid sequence of any of SEQ ID NOs: 1, 2, 3 or 4. In a particular embodiment, the agent or composition comprises a nucleic acid encoding a GDF11 polypeptide or a functional fragment or variant thereof.

In a particular embodiment, the GDF11 variant is as described in WO2019/144053.

In a particular embodiment, the GDF11 polypeptide comprises a modified GDF11 polypeptide. In a particular embodiment, the modified GDF11 polypeptide comprises a modification selected from the group consisting of fusion to an Fc fragment, pegylation, conjugation to albumin, an amino acid mutation that prevents or reduces proteolytic degradation, an amino acid mutation that prolongs half-life, and any combination thereof.

In a particular embodiment, the composition is administered via a route selected from the group consisting of intravenously, subcutaneously, intra-arterially, and intramuscularly.

In a particular embodiment, the levels of GDF11 polypeptide are increased by at least 100% of healthy reference levels. In a particular embodiment, the levels of GDF11 polypeptide are increased to at least 75% of healthy reference levels.

In a particular embodiment, the composition increases the levels of GDF11 polypeptide in at least one of the subject's systemic circulation, cerebral vasculature, cerebrospinal fluid, cerebral tissue, lateral ventricles, neurovasculature, and subventricular zone neurovascular niche.

In a particular embodiment, the composition comprises an isolated or recombinant GDF11 polypeptide. In a particular embodiment, the isolated or recombinant GDF11 polypeptide comprises a modification selected from the group consisting of fusion to an Fc fragment, pegylation, conjugation to albumin, an amino acid mutation that prevents or reduces proteolytic degradation, an amino acid mutation that prolongs half-life, and any combination thereof.

In a particular embodiment, a molecule that increases GDF11 levels, especially a GDF11 polypeptide or functional fragment or variant thereof, activates or modulates the ALK4/5 receptor. In a particular embodiment, a GDF11 polypeptide or functional fragment or variant thereof, modulates the SMAD signaling cascade.

In a particular embodiment, the levels of GDF11 polypeptide are increased in at least one of the subject's systemic circulation, cerebral vasculature, cerebral tissue, cerebrospinal fluid, lateral ventricles, neurovasculature, and subventricular zone neurovascular niche.

Methods of Screening

Also provided are methods of screening a compound, e.g., a test candidate chemical compound. The methods may comprise administering a test compound to a subject having a mood disorder and/or anxiety disorder; obtaining a sample from the subject; contacting the sample with a GDF11-binding molecule; and detecting bound GDF11. In a particular embodiment, the disorder is a mood disorder or an anxiety disorder. In a particular embodiment, the mood disorder is a major depressive disorder. In a particular embodiment, the subject is a human. In a particular embodiment, the subject is less than 65 years old. In a particular embodiment, the sample is plasma. In a particular embodiment, the GDF11-binding molecule is an anti-GDF11 antibody or a molecule comprising an antigen-binding fragment of an anti-GDF11 antibody. In a particular embodiment, the method comprises an enzyme-linked immunosorbent assay (ELISA) or an ultrasensitive single molecule array (Simoa) technology.

In a particular embodiment, the screening methods comprise measuring the levels of GDF11 in samples obtained from said subject. Said samples can be obtained prior to and/or after the administration of the test compound. In a particular embodiment, if the levels of GDF11 in the sample collected after the administration of the compound are significantly lower than healthy reference levels or not significantly higher than the initial GDF11 levels measured in the sample collected prior to the administration of the compound, then the test compound is not identified as having a mood disorder and/or anxiety disorder treating activity. Conversely, if the levels of GDF11 in the sample collected after the administration of the compound are not significantly lower than healthy reference levels or are significantly higher than the initial GDF11 levels measured in the sample collected prior to the administration of the compound, then the test compound is identified as having a mood disorder and/or anxiety disorder treating activity. Specifically, if the levels of GDF11 in the sample collected after the administration of the compound are significantly higher than healthy reference levels or than the initial GDF11 levels measured in the sample collected prior to the administration of the compound, then the test compound is identified as having a mood disorder and/or anxiety disorder treating activity.

In the context of these methods, the test compound may be any type of chemical entity suitable for use as a therapeutic.

EXAMPLES

I. Material and Methods (for Examples 1-5)

Human Study Design and Participants

This is a cross-sectional study nested in a large cohort study including a community sample of young adults. Full details of the original study were published previously (Moreira F P et al[25]). Briefly, all participants were assessed using the Mini International Neuropsychiatric Interview (MINI), a structured psychiatric interview based on the Diagnostic and Statistical Manual of Mental Disorders (DSM-IV) diagnostic criteria. In addition, the severity of depressive symptoms was assessed using the Montgomery-Asberg Depression Rating Scale (MADRS). Height was measured without shoes to the nearest 0.1 cm. Weight was measured in kilograms to the nearest 0.1 kg. Body Mass Index (BMI) was calculated using the weight (in kilograms) and height (in meters), according to the formula: $Kg/m^2$ (World Health Organization (WHO), 2008. Waist circumference and waist-hip ratio, Report of a WHO Expert Consultation, World Health Organization Geneva, Switzerland). For the purpose of the present study, 57 young adults were selected with Major Depressive Disorder (MDD) and 51 healthy controls without mood disorders (MDD or bipolar disorder), anxiety disorders (panic disorder, agoraphobia, social phobia, generalized anxiety disorder), Obsessive-Compulsive Disorder, Posttraumatic Stress Disorder, or Attention deficit hyperactivity disorder. The groups were matched by gender, age, years of education, and BMI.

Blood Collection from Human Subjects

Ten milliliters of blood were withdrawn from each subject by venipuncture into a free-anticoagulant vacuum tube. The blood was immediately centrifuged at 3,500 g for 15 minutes, and serum was kept frozen at −80° C. until analysis.

GDF11 Level Quantification in Human Serum

GDF11 serum levels were determined by sandwich-ELISA using the Human GDF-11/BMP-11 DuoSet ELISA kit according to the manufacturers instructions (R&D Systems, USA). Briefly, microtiter plates (96-well flat-bottom) were coated overnight at room temperature with the anti-human GDF11 capture antibody at 4 μg/mL in PBS. Thereafter, the plates were washed three times with a wash buffer and blocked with 1% BSA solution for 2 hours at room temperature. After washing, the plates were incubated overnight at 4° C. with the samples and the standard curve ranged from 15.65 to 2,000 pg/mL of GDF11. Plates were washed and a biotinylated anti-human GDF11 detection antibody at 400 ng/mL was added, which was incubated for 2 hours at room temperature. After washing, incubation with streptavidin-peroxidase conjugate (diluted 1:40 in 1% BSA solution) for 20 minutes at room temperature was performed and subsequently, plates were washed again and incubated with the substrate solution for 20 minutes at room temperature. Finally, the stop solution (2N sulfuric acid) was added and the amount of GDF11 was determined by measuring absorbance at 450 nm with correction at 540 nm. The standard curve demonstrates a direct relationship between optical density and GDF11 concentration.

It is important to note that the GDF8 (also called myostatin) was used as a control for the specificity of the GDF11 kit. The GDF8 (Peprotech, USA) was tested at the same concentration as the highest GDF11 standard (2,000 pg/mL)

as well as at a middle value of the GDF11 standard curve (500 pg/mL). GDF8 was not detected at any concentration (for detailed information see Katsimpardi et al., Aging Cell, 2019[1]).

Animals

Young (3 months) and aged (22 months) C57BL/6JRj mice were obtained from Janvier Labs (France). All animals were group housed and provided free access to water. All animal procedures were performed in accordance with French legislation and in compliance with the European Communities Council Directives (2010/63/UE), according to the regulations of Institut Pasteur Animal Care Committees.

GDF11 Administration in Mice

GDF11 (Peprotech, Cat #120-11) was dissolved in water, further diluted according to the manufacturer's instructions and injected at a concentration of 1 mg/kg, as previously described in Katsimpardi et al, Aging Cell, 2019[1]. Control mice (young or aged) were injected with equivalent volumes of saline. All mice were injected daily at 7 pm for the duration of the experiment.

Mini-osmotic pump implantation and intracerebroventricular (ICV) GDF11 infusion in mice Twenty-four hours before implantation, programmable and refillable mini-osmotic pumps (iPrecio, SMP-300) were filled with saline, under sterile conditions, and programmed to deliver the infusion at a constant rate of 1 μl/hour. Twenty-four hours later, mini-osmotic pumps were implanted into the right lateral ventricle of 21-month old mice (AP −0.5; ML+1.0; DV −2.0). The pumps were refilled with GDF11 solution (0.3 mg/kg rGDF11 in saline) or saline every four days for a total volume of 120 μl.

Behavioral Tests in Mice

Novel Object Recognition test (NORT): Four gray arenas (45×45 cm) with high walls were used and luminosity was set at 30 lux throughout the habituation and the test phases. Mouse cages were placed in the behavior room for habituation 30 min prior to the test. Mice were habituated to the arenas for 3 consecutive days as follows. On Habituation Day 1, mice housed in the same cage were place in one arena for 30 min. Then each mouse was individually placed in one arena for 10 min each. On Days 2 and 3 mice were individually placed in an arena for 10 min each. On Day 4 (NORT), mice were individually placed in the arena where 2 identical objects were placed at equal distances from the walls and from each other, and the mice were left to explore for 10 min and put back in their home cage. Two hours later, mice were placed back in the arena where one of the two objects was replaced with a novel object, and the mice were left to explore for 10 min. A camera above the arena automatically captured the locomotor activity of each mouse, and its behavioral pattern was measured and analyzed using EthoVision XT software (Noldus) and confirmed by a blind manual measurement of the time spent sniffing the objects. To exclude a spontaneous preference towards one of the objects, several pairs of objects had previously been tested with different sets of naive young and aged animals, and objects with no preference were chosen for the experiment.

Splash test: Mouse cages were placed in the behavior room for habituation 30 min prior to the experiment. Then, all mice, except for the experimental mouse, were transferred to a different cage. The experimental mouse was given a spray shot of a 10% sucrose solution on the lower back and then put back in the home cage. The viscosity of the sucrose solution dirties the fur, inducing a grooming behavior. The mouse was observed for 6 minutes during which the frequency of grooming, the latency to first groom and the total grooming times were measured. After the test, the experimental mouse was placed in a different cage until all the mice of the cage had been subjected to the test.

Tail suspension test (TST): Mouse cages were placed in the behavior room for habituation 30 min prior to the experiment. One mouse per condition was placed in the TST apparatus by applying tape on the mouse's tail and using it to hang the mouse upside down. The test lasted for 6 minutes during which immobility time was measured by a blind observer.

Light/Dark box test: Time spent and frequency of entry in the light box (178 lux), were measured during 10 min. A camera above the arena automatically captured the locomotor activity of the mice, and their behavioral patterns were measured and analyzed using EthoVision XT software (Noldus).

II. Results (Examples 1-5)

Figure 1:
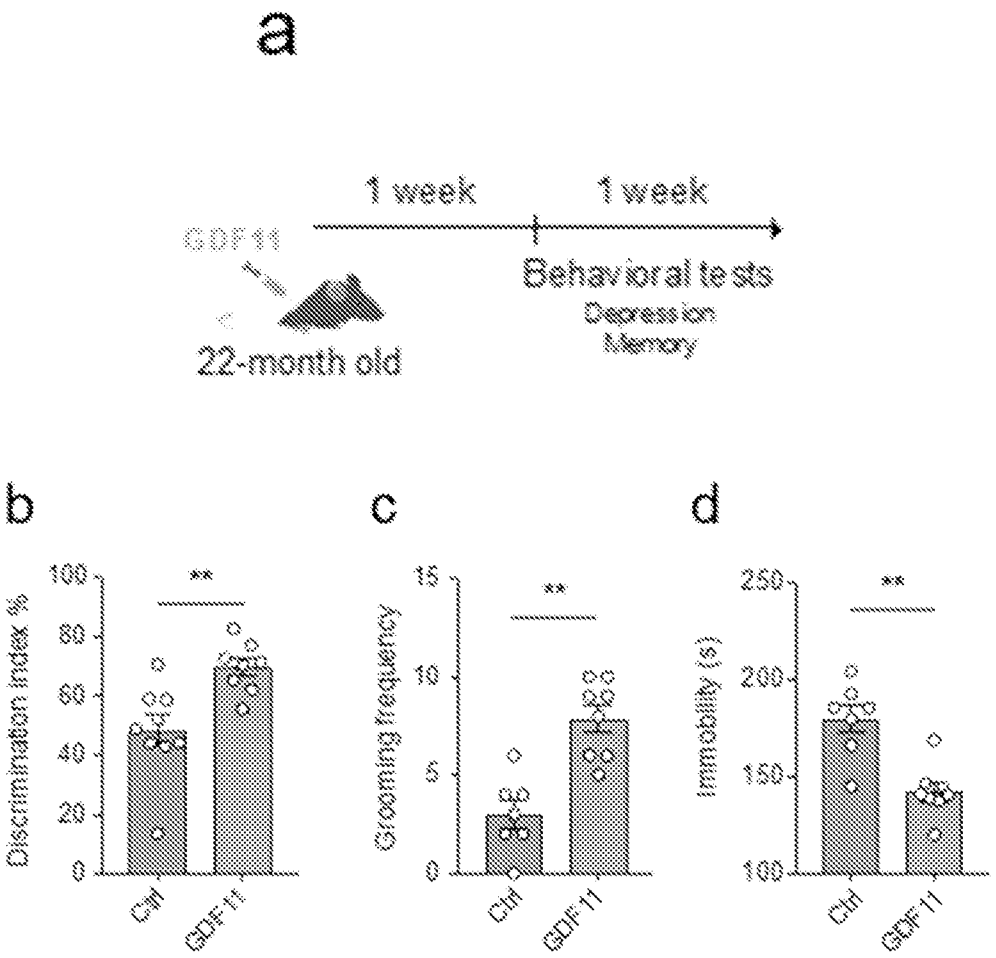
FIG. 1. Systemic GDF11 administration restores memory impairments and depression in aged mice and GDF11 levels are reduced in young people with MDD. (a) Schematic representation of the experimental procedure (b) Measurement of discrimination index during the NORT (percentage of time spent to observe the novel object divided by the percentage of total investigation time for both objects) ($n_Y$=10, $n_{GDF11}$=8, $n_O$=9 mice per group). (c) Measurement of grooming frequency during the Splash test ($n_Y$=7, $n_{GDF11}$=7, $n_O$=8 mice per group). (d) Measurement of immobility time during the TST ($n_Y$=8, $n_{GDF11}$=8, $n_O$=7 mice per group). (e) Table describing the clinical characteristics of the human sample. Young adults with MDD and healthy control participants were matched by sex, age, years of education, and BMI. (f) Measurement of GDF11 by ELISA immunoassay in the serum of human healthy controls or MDD patients ($Median_{CONTROL}$=22.69 pg/ml, $Median_{MDD}$=11.66 pg/ml.
Figure 6:
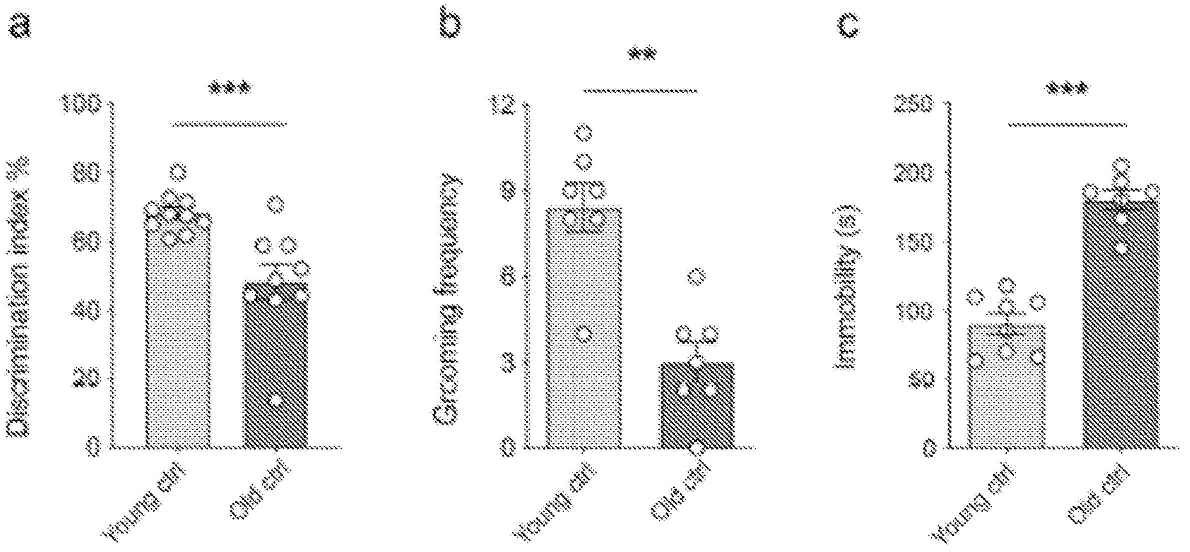
FIG. 6. Increased levels of GDF11 in the blood correlate with improved memory and mood state in aged mice. (a) Measurement of discrimination index during the NORT (percentage of time spent to observe the novel object divided by the percentage of total investigation time for both objects) ($n_Y$=10, $n_O$=9 mice per group). (b) Measurement of grooming frequency during the Splash test (n=7 mice per group). (c) Measurement of immobility time during the TST (n=7 mice per group). (d-f) Real-time qPCR for hallmarks of senescence showing fold changes in mRNA levels of p16 (d), p19 (e) and p21 (f) ($n_Y$=9, $n_{GDF11}$=5, $n_O$=9 mice per group). (g-h) Quantification of Western blots by optical intensity for Foxo3a (g) and Beclin (h) (n=3 mice per group). One-way ANOVA and Tukey's post hoc test; Mann-Whitney test for two-group comparisons; *P<0.05, P<0.01; *P<0.001; ****P<0.0001; mean±S.E.M.

1. GDF11 Levels in Blood Correlate With Improved Memory and Mood State in Aged Mice It was shown previously that GDF11 had a rapid effect on organismal metabolism, by inducing weight loss and a simultaneous increase in SVZ neurogenesis within 9 days of systemic treatment[1]. It was decided to investigate whether GDF11 treatment could restore age-associated cognitive impairments and a functional improvement on learning and memory, as well as mood states, all of which are affected by aging. 22-month old mice were injected with recombinant GDF11 (rGDF11) via daily intraperitoneal (IP) injections at a dose of 1 mg/kg ("Old GDF11"). Aged-matched control mice ("Old ctrl") were injected with equal volumes of saline. Both groups of mice were injected for 22 days and behavioral tests were run during the last days of the treatment (FIG. 1*a*). First their memory was tested using the novel object recognition test (NORT)[4]. As expected, control aged mice scored significantly lower than young mice, as they were unable to discriminate the novel object from the familiar one ($DI_{Youngctrl}$=64.52%; $DI_{Oldctrl}$=48.51%; DI=discrimination index; FIG. 6*a*). On the contrary, GDF11-treated aged mice presented a 47.8% increase in novel object discrimination index compared with the control aged mice ($DI_{OldGDF11}$=71.7%), suggesting a restoration of memory decline after GDF11 treatment in aged mice (FIG. 1*b*). Subsequently, mice were subjected to behavioral tests aimed at assessing the level of anhedonia and depression. During the Splash Test, which consists in spraying a 10% sucrose solution on the back of the mouse and measuring the number of grooming sessions the mouse performs as a behavioral measure of the animal's mood state[5], aged mice scored lower than young controls (FIG. 6*b*). Nevertheless, GDF11-treated aged mice showed a 2.5-fold higher grooming frequency than old control mice, which is similar to the score of young mice (FIG. 1*c*), suggesting an improved mood state. To further examine the reversal of the depression-like state after GDF11 treatment, the Tail Suspension Test was performed, which measures despair-like behavior. In this test, mice were hung upside down from their tails, and immobility time was measured during 6 minutes. Old GDF11-treated mice were significantly more mobile than old controls, which remained immobile longer than both young and GDF11-treated mice (FIG. 1*d* and FIG. 6*c*). These findings suggest that increased levels of GDF11 in the blood correlate with improved memory and mood state in aged mice.

2. Blood GDF11 Levels are Associated with Psychiatric Pathology in Humans

It was then assessed whether blood GDF11 levels would be associated with a related psychiatric pathology in humans. Patients with major depressive disorder (MDD) and healthy controls matched by sex, age and education levels were recruited (FIG. 1*e*). All participants were subjected to psychiatric evaluation to assess the MADRS score (FIG. 1*e*). Blood was collected from these MDD patients (n=57), as well as from the age-matched healthy controls (n=51) and serum was isolated and analyzed via a sandwich ELISA immunoassay for the detection of serum GDF11 levels. As previously described[1], the assay was first confirmed to exclusively detect GDF11 and not GDF8. Analysis of serum GDF11 levels showed a 48.6% decrease in MDD patients compared to healthy controls ($Median_{CONTROL}$=22.69 pg/ml, $Median_{MDD}$=11.66 pg/ml; FIG. 1*f*) and no statistical difference was observed between men and women (FIG. 1*e*). Taken together, the above data indicate an association between peripheral GDF11 levels and mood states in both mice and humans.

3. Cellular Changes in Brains of Aged Mice

Next, the cellular changes were evaluated in the brains of aged mice with or without GDF11 treatment. First, it was confirmed that GDF11 treatment restored neurogenesis in aged mice[2,3], but the earliest time point where these anti-aging effects could take place was examined. Already at 9 days of daily systemic GDF11 administration we found a 34.8% significant increase in $Sox2^+$ NSC populations in the subgranular layer (SGL) of the Old GDF11 dentate gyrus (DG) compared to old control mice (FIGS. 2*a* and *b*). At the same time point, analysis of DCX (doublecortin, a marker of immature neuroblasts) in the SGL of old and GDF11-treated old mice revealed a 52.9% increase in the number of $DCX^+$ neuroblasts in the neurogenic SGL of GDF11-treated aged mice compared to aged controls (FIGS. 2*a* and *c*). Senescence[7,8], a hallmark of aging, was also examined by quantifying the expression of Cdkn2a locus transcripts (encoding p16 and ARF) and p21, which are essential for the establishment of senescence, in the hippocampi of young, aged control and aged GDF11-treated mice by real-time qPCR. Consistent with previous reports[9], both p16 and ARF expression increased during aging (FIG. 6*d*). Remarkably, hippocampal senescence was significantly reduced in aged mice after only 9 days of GDF11 treatment compared to saline, as seen by p16 and ARF expression (FIG. 2*d,e*). In contrast, as previously reported[9], no significant changes were detected in p21 among the three groups (FIG. 6*e*). Because of the tight link between cognitive impairments and defects in the autophagic process, we next sought to examine the effect of GDF11 treatment on hippocampal autophagy. Western blot analysis of the hippocampal tissue showed that key proteins, such as FoxO3a and Beclin1, which are involved in the initiation of the autophagic process, were downregulated with aging in the hippocampus (FIG. 6*f*). However, upon systemic GDF11 treatment, a significant upregulation of FoxO3a, Beclin1 and Atg5 was observed (FIG. 2*g-h*, respectively). Moreover, the autophagic flux was evaluated by measuring the LC3I/II ratio (FIG. 2*i*), whereas no change was observed for p62 (FIG. 2*j*).

4. GDF11 Regulated Autophagy

Figure 4:
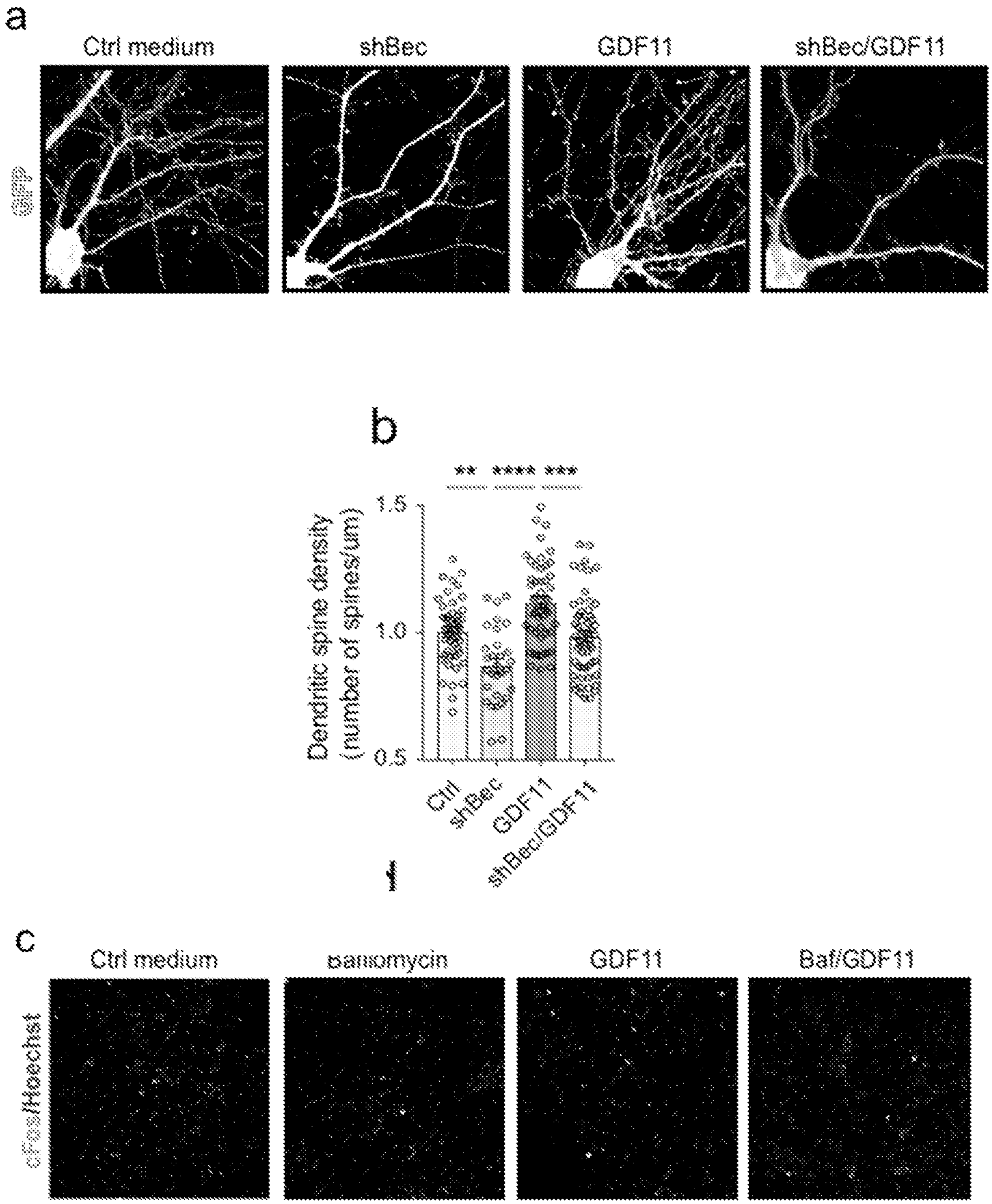
FIG. 4. GDF11 stimulation of neuronal activity is mediated through autophagy. (a) Representative confocal images of GFP+ dendrites and spines from hippocampal neurons in culture transfected with either shBeclin or GFP and treated with either GDF11 or control. (b) Quantification of dendritic spine density (g) after a 2-hour stimulation with either GDF11 or control (number represents number of spines for every 10 um of primary dendrite). (c) Representative confocal images of hippocampal neurons in vitro treated with either GDF11 or Bafilomycin or both and immunostained with cFos (green) and Hoechst (blue). (d) Quantification of (c) cFos+ neurons per field. (e) Oxygen consumption rate in hippocampal neurons in vitro treated with either GDF11 or Bafilomycin or both and measured with the Seahorse analyzer. Mann-Whitney test for two-group comparisons; *P<0.05, ** P<0.01; mean±S.E.M.

It was then evaluated whether the beneficial effect of systemic GDF11 on the aged brain resulted from a direct GDF11 action on neurons. Since the action of GDF11 on neuronal activity has never been investigated before, we examined whether GDF11: a) acts directly on neurons, b) affects neuronal activity and c) enhances autophagy in line with the in vivo findings. To address this question, in vitro cultures of hippocampal neurons were established. As described in FIG. 3*a*, hippocampal neurons were plated on Day 0 and were kept to mature for the next 18 days in vitro (DIV), and different treatments took place during this time period. First, the downstream signaling of GDF11, which typically activates the ALK4/5- SMAD2/3 pathway, was examined. On DIV18 neurons were treated with rGDF11 (20 ng/ml) or media change as a control. Cells were collected after 30 min of treatment and were immediately processed for protein isolation and quantification. Subsequent Western blot analysis showed that SMAD2/3 phosphorylation was enhanced when neurons were treated with rGDF11 compared to controls (FIG. 3*b*), demonstrating activation of the canonical GDF11 signaling pathway in these neurons. Next we examined whether GDF11 treatment directly activates hippocampal autophagy. Thus, the expression of Beclin, a protein which is activated at the initiation of the autophagy process, was tested, as well as LC3I/II and p62, which allowed to evaluate the autophagic flux. Western blot analysis of these markers revealed that a 30-minute GDF11 stimulation significantly increased the expression of Beclin by 1.4-fold (FIG. 3*d*), as well as the autophagic flux as seen with the combination of LC3I/II lipidation and p62 expression (FIGS. 3*e* and *f*, respectively). Consequently, it was examined whether GDF11 would also directly stimulate neuronal activity in hippocampal neurons. On DIV14, neurons were transfected with a GFP plasmid to allow subsequent visualization and quantification of the spines. On DIV18 neurons were stimulated with either GDF11 (20 ng/ml) or chemical LTP (cLTP; positive control) or media change (negative control) for 2 h. Measurement of the number spines on GFP+ neurons showed that, as expected, cLTP induced a significant increase of dendritic spines by 23% compared to the control (FIG. 3*g,i*). Surprisingly, GDF11 stimulation had a higher effect than cLTP as it significantly increased dendritic spine density by 48% compared to the control, and by 21% compared to cLTP (FIG. 3*g,i*). Consequently we examined activation of immediate early gene cFos, a marker for neuronal activity. For this, neurons were stimulated with either GDF11 (20 ng/ml) or cLTP or control for 30 min. Immunostaining for cFos revealed that cLTP significantly enhanced neuronal activity 11-fold compared to control neurons (FIG. 3*h,j*). Interestingly, GDF11 stimulation also significantly enhanced neuronal activity 7.5-fold compared to control neurons (FIG. 3*h,j*). Taken together, the above results show that GDF11 treatment on hippocampal neurons directly affects its canonical SMAD2/3 signaling pathway, enhances autophagy and stimulates neuronal activity. Consequently, it was assessed whether GDF11 action on neuronal function is mediated through the autophagic process. On DIV 14 neurons were transfected with either GFP plasmid alone, or both GFP and shBeclin. On DIV 18 neurons were treated with GDF11 or control for 2 hours to examine dendritic spine density. Similar to the above results, GDF11 alone increased numbers of spines, but blockage of autophagy together with GDF11 treatment resulted in a significant reduction in spine density (FIG. 4*a,b*).

In order to ensure that the autophagy process—and not Beclin itself—interferes with GDF11 action, autophagy was blocked at a later phase of the autophagic process (lysosome acidification) by using Bafilomycin A1 inhibitor. In this experiment, hippocampal neurons on DIV18 were treated with either Bafilomycin or GDF11 or both or nothing (media change) for 2 hours and cFos activation was measured. Immunohistochemical analysis of these neurons for cFos in GFP+ neurons exhibited a significant increase of cFos after GDF11 treatment, significant downregulation of cFos by Bafilomycin, and an intermediate state when cells are treated with GDF11 but autophagy is blocked (FIG. 4*a,b*), thereby demonstrating that changes in the autophagic flux, and not just the initial signaling, interfere with GDF11 action on hippocampal neuron activation. Since neuronal autophagy is tightly linked to the bioenergetic function of the cell, we also examined how GDF11 could affect the neuron's metabolic function. For this, in vitro hippocampal neurons were treated with Bafilomycin and/or GDF11 as described above, and their energy phenotype were examined using the Seahorse analyzer. Interestingly, Bafilomycin addition and GDF11 change the metabolic profile of neurons compared to control, but when both Baf and GDF11 are together the shift disappears (FIG. 4*e*). Taken together, these findings demonstrate that GDF11 acts directly on neurons to enhance neuronal activity and autophagy, but when autophagy is blocked, the action of GDF11 is reduced, thus providing evidence that the action of GDF11 is mediated through autophagy.

5. Direct Action of GDF on Neurons In Vivo

Figure 5:
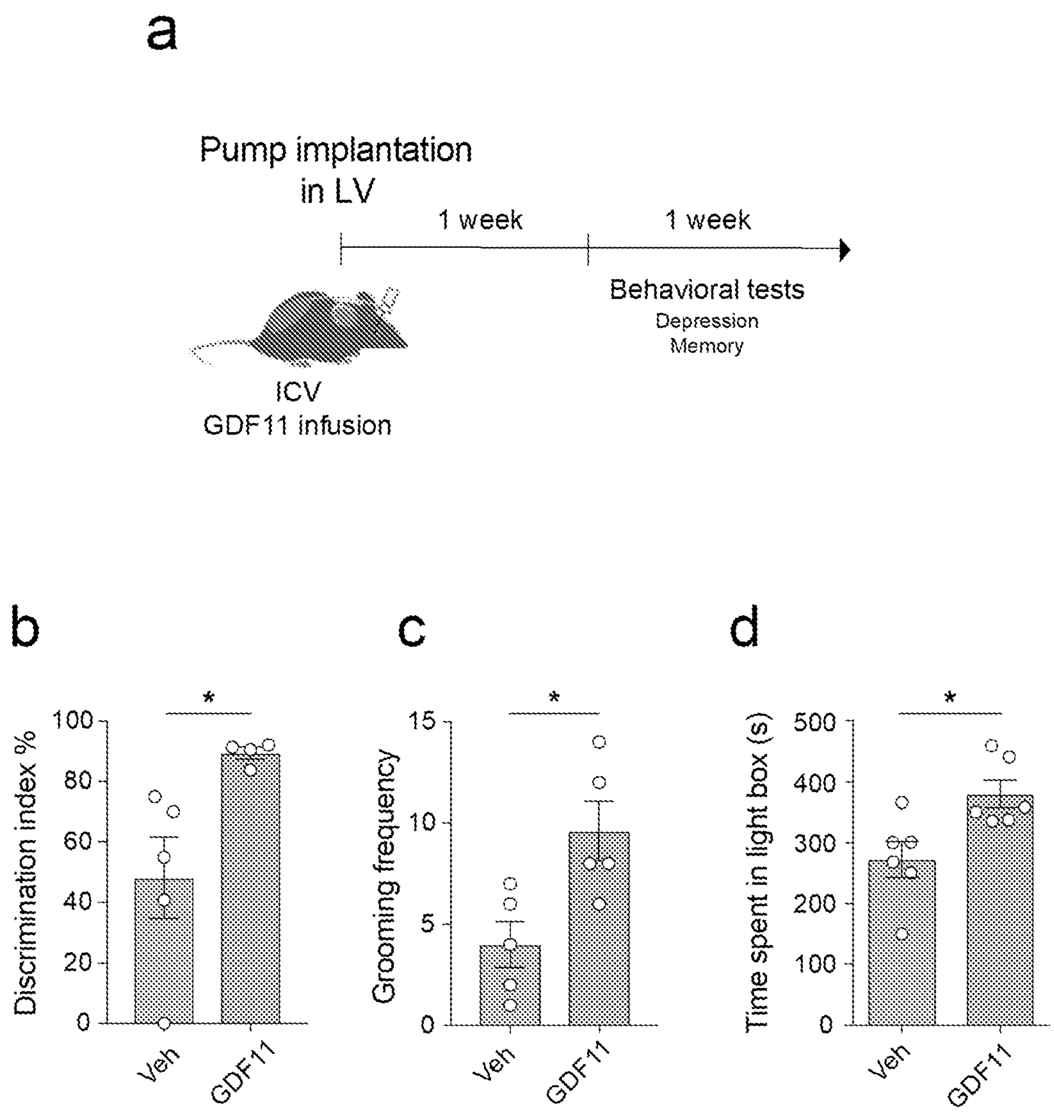
FIG. 5. GDF11 stimulation of neuronal activity is mediated through autophagy. (a) Schematic representation of the experimental procedure (b) Measurement of discrimination index during the NORT (percentage of time spent to observe the novel object divided by the percentage of total investigation time for both objects) (n=5 mice per group). (c) Measurement of grooming frequency during the Splash test (n=5 mice per group). (d) Measurement of time spent in the light box during the Light/Dark Box Test (n=6 mice per group). (e-h) Quantification of Western blots by optical density for Beclin (n=4-5 mice per group) (c), Atg5 (n=4-5 mice per group) (d), and Lamp1 (n=4-5 mice per group) (f). Mann-Whitney test for two-group comparisons; *P<0.05; mean±S.E.

Next, it was asked whether direct action of GDF11 on neurons in vivo would recapitulate the effects seen with systemic injections. To address this question, we intracerebroventricularly (ICV) implanted cannulas connected to mini-osmotic pumps in the lateral brain ventricle of 21-month old mice. The pumps continuously delivered rGDF11 (0.3 or 0.5 mg/kg) or saline (Veh) for the whole length of the treatment (2 weeks) (FIG. 5*a*). In each condition, behavioral tests were performed the last week of the experiment. the NORT was performed, as described above, and it was found that ICV GDF11 induced significant improvement of memory in old mice compared to ICV Veh (FIG. 5*b*). Behavioral tests were then performed to assess depression, such as the Splash test and the Light/Dark box test (to replace the TST, in order to avoid bias because of the implanted pumps). ICV GDF11 induced a significant improvement in grooming frequency compared to ICV Veh (FIG. 5*c*). Moreover, ICV GDF11-infused mice scored significantly better in the Light/Dark box test (FIG. 5*d*). Taken together, these findings demonstrate that GDF11 can improve cognitive deficits when infused directly in the brain.

Figure 7:
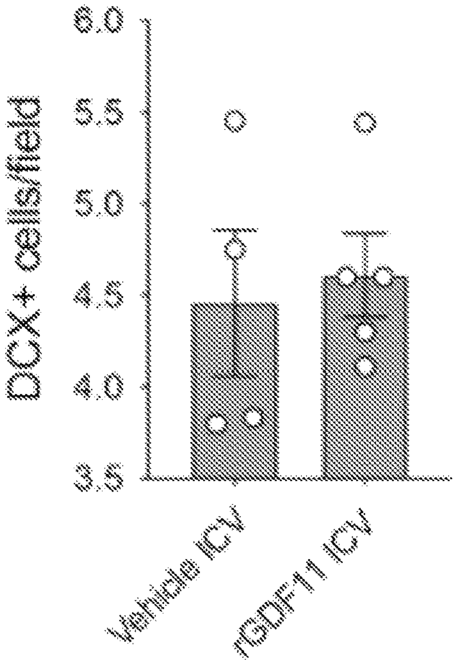
FIG. 7. Quantification of DCX+ neuroblasts in the SGL of the dentate gyrus ($n_{G/ICV}$=5, $n_{O/ICV}$=4 mice per group).

Next, the brains of these mice were analyzed and it was found that hippocampal neurogenesis remained unchanged after GDF11 ICV treatment (FIG. 7). However, Western blot analysis of the brains collected from the mice showed an increase in markers of autophagy, such as Beclin, Atg5 and Lamp1 (FIG. 5 *f-h* respectively), thereby showing that direct action of GDF11 in the brain can improve both memory impairments as well as age-related depression due to the increase of neuronal autophagy.

Example 6. Influence of the Type of Sample

To identify the best way to assay GDF11 levels in the context of the invention, it has been decided to measure and compare GDF11 levels among paired samples of serum, plasma (citrate and EDTA), and platelet-rich plasma on healthy individuals, to evaluate if the type of sample would improve the assay performance.

Methods: Blood from four healthy individuals was collected in different tubes: tube without anticoagulant to obtain serum and tubes with anticoagulant (EDTA or citrate) to obtain plasma, platelet poor plasma and platelet rich plasma. The tubes without anticoagulant and the tubes with the anticoagulant EDTA were centrifuged at 2000 g for 10 minutes at 4° C. to obtain serum and plasma (EDTA), respectively. From the tubes with the anticoagulant citrate, an aliquot of blood was taken and centrifuged at 2000 g for 10 minutes at 4° C. to obtain plasma (citrate)—Platelet Poor Plasma. The remaining blood from the citrate tubes was used to obtain Platelet Rich Plasma (PRP) following the method by Du et al, 2018[13], in two different conditions: (1) PRP-controlled temperature, which was performed under hypothermic conditions using precooled tubes and tips and refrigerated centrifuge; and (2) PRP—not controlled temperature, which was performed at room temperature. Briefly, the blood was first centrifuged at 200 g for 10 minutes at 4° C., then the obtained plasma was transferred to new tubes and centrifuged again at 1550 g for 10 minutes at 4° C. After the centrifugation, one milliliter of plasma at the bottom and precipitated platelets (PRP) were transferred to a new glass tube and then, for the first condition (PRP-controlled temperature) incubate for 15 minutes at 37° C. to activate the platelets. Aliquots of serum, plasma (EDTA), plasma (citrate), PRP-controlled temperature and PRP—not controlled temperature were stored at −80 C until GDF11 analysis. GDF11 was measured in these samples, in duplicate, by the same ELISA immunoassay (R&D Systems) previously used.

Quantification of GDF11 serum levels by ELISA method: GDF11 serum levels were determined by sandwich-ELISA using the Human GDF11/BMP-11 DuoSet ELISA kit according to the manufacturers instructions (R&D Systems, USA). Briefly, microtiter plates (96-well flat-bottom) were coated overnight at room temperature with the anti-human GDF11 capture antibody at 4 μg/mL in Phosphate-buffered saline (PBS). Thereafter, the plates were washed three times with a wash buffer and blocked with 1% Bovine Serum Albumin (BSA) solution for 2 hours at room temperature. After washing, the plates were incubated overnight at 4° C. with the samples and the standard curve ranged from 7.83 to 2,000 pg/mL of GDF11. Plates were washed and a biotinylated anti-human GDF11 detection antibody at 400 ng/mL was added, which was incubated for 2 hours at room temperature. After washing, incubation with streptavidin-peroxidase conjugate (diluted 1:40 in 1% BSA solution) for 20 minutes at room temperature was performed and subsequently, plates were washed again and incubated with the substrate solution for 20 minutes at room temperature. Finally, the stop solution (2N sulfuric acid) was added and the amount of GDF11 was determined by measuring absorbance at 450 nm with correction at 540 nm. The standard curve demonstrates a direct relationship between optical density and GDF11 concentration. It is important to note that the inventors used the GDF8 (also called myostatin) as a control for the specificity of the GDF11 kit. The GDF8 (Prepotech, USA) was tested at the same concentration as the highest GDF11 standard (2,000 pg/mL) as well as at a middle value of the GDF11 standard curve (500 pg/mL). GDF8 was not detected at any concentration. All GDF11 ELISA analysis described in this report followed the above-mentioned procedure.

Results: Preliminary analyses with a small sample size (n=4 healthy individuals) showed that the different sample types seem not to influence the detection of GDF11.

Example 7. Influence of the Dilution Factor

Sample dilution was also optimized, especially for samples with complex matrices, such as serum and plasma. Different dilution factors were therefore tested, to see if it would improve the assay performance.

Methods: GDF11 was measured by the same ELISA immunoassay (R&D Systems) previously used in eight serum samples (from patients with mood disorders) in duplicate and in different dilutions factors, as follows: 1:3, 1:5, 1:10, 1:50, and with no dilution.

Figure 8:
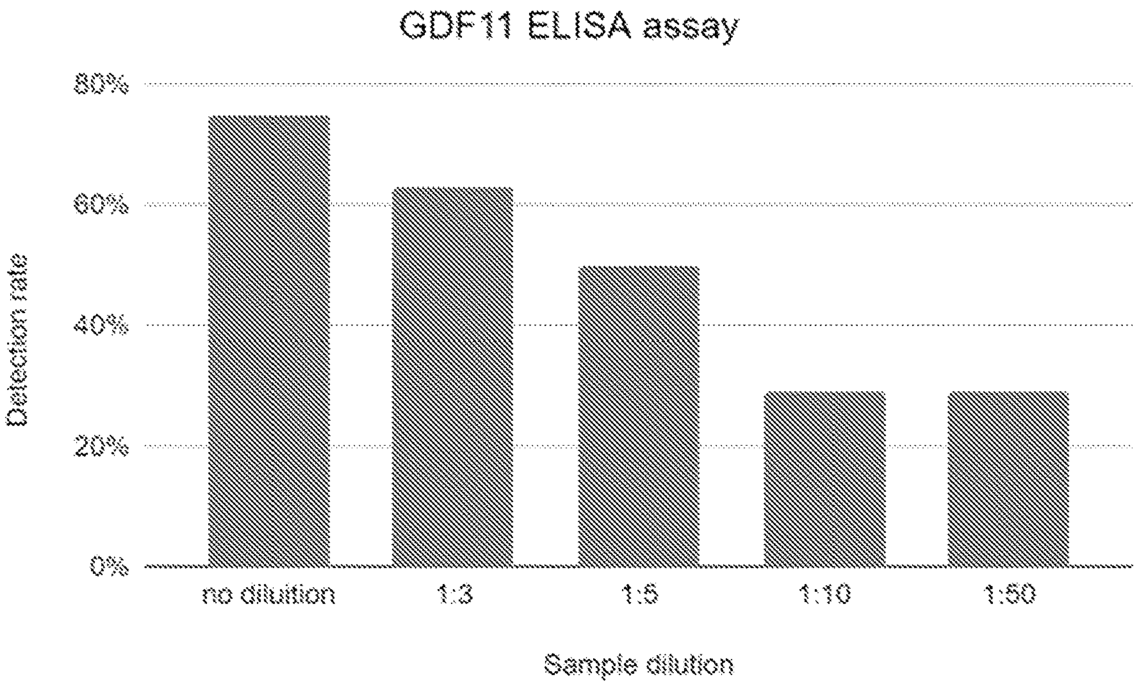
FIG. 8. Detection rate for GDF11 ELISA assay. GDF11 detection rate (%) by ELISA assay (R&D systems) in serum samples from individuals with mood disorders.

Results: The results showed that the condition with no dilution provided the best detection of GDF11 for serum samples (FIG. 8).

Example 8. Influence of the Sample Size

The serum GDF11 levels were assessed in a large sample (n=1,019) of young adults (21-32 years old). The methods and results of this experiment are described below.

Methods: This is the second wave of prospective cohort study, including a population-based sample of young adults. In the first wave (2007-2009), sampling was performed by clusters, considering a population of 39 667 people in the target age range (18-24 years-old), according to the current census of 448 sectors in the city Pelotas/Brazil. From these sectors, 89 census-based sectors were randomly selected. The home selection in the sectors was performed according to a systematic sampling, the first one being the house at the corner pre-established as the beginning of the sector, and the interval of selection was determined by skipping two houses. Therefore, the sample is representative of the target population due to the probabilistic sampling adopted. The first wave included 1560 young adults aged between 18-24. The second wave took place a mean of five years later (2012-2014), and all young adults included in the first wave were invited for a reassessment. This report describes only data from the second wave. In the second wave, the presence of a lifetime or current major depressive episode (unipolar or bipolar) was assessed using the Mini International Neuropsychiatric Interview-Plus (MINI-Plus) by trained psychologists. Importantly, our controls (individuals without a history of a major depressive episode) could have other psychological conditions. Height was measured without shoes to the nearest 0.1 cm. Weight was measured in kilograms to the nearest 0.1 kg. The Body Mass Index (BMI) was calculated as the weight (in kilograms) and height (in meters), according to the formula: Kg/m2. In addition, 10 mL of blood was withdrawn from each subject by venipuncture into a free-anticoagulant vacuum tube. The blood was immediately centrifuged at 3.500 g for 15 min, and the serum was kept frozen at −80° C. until analysis. GDF11 was measured using the same ELISA immunoassay (R&D Systems) previously used and the detection rate for GDF11 in this experiment was 87%. The statistical analysis was performed in the SPSS 21 using the chi-squared test, student t test, Man-Whitney U test, and the Spearman correlation.

Results: The study included 1,019 young adults aged between 21 and 32 years old. Regarding the sample characteristics, the majority were females (58.7%), the mean age was 25.83±2.16, and the mean years of education was 11.00±3.58. The prevalence of a lifetime or current major depressive episode (unipolar or bipolar) in this sample was 33.6% (n=342). Table 1 describes the sample characteristics and their association with a history of a major depressive episode.

TABLE 1

Sample characteristics and their association with a history of a major depressive episode.

| | History of a major depressive episode | | |
|---|---|---|---|
| | No<br>n = 677 | Yes<br>n = 342 | p-value |
| Sex | | | <0.001 |
| Male | 339 (50.1%) | 82 (24.0%) | |
| Female | 338 (49.9%) | 260 (76.0%) | |
| Age | 25.75 ± 2.17 | 25.99 ± 2.12 | 0.103 |
| Years of education | 11.26 ± 3.58 | 10.47 ± 3.49 | 0.001 |
| BMI | 26.22 ± 5.21 | 26.26 ± 5.68 | 0.896 |

Legend: BMI: Body Mass Index.

Females presented a higher prevalence of major depressive episodes as compared to males (p<0.001), and individuals with a history of a major depressive episode had less years of education as compared to individuals without a history of a major depressive episode (p=0.001). There was no significant difference between the groups regarding age and BMI. Table 2 shows the sample characteristics and their association with GDF11 levels.

TABLE 2

Sample characteristics and their association with GDF11 levels.

| | GDF11 levels (pg/mL) | p-value |
|---|---|---|
| Sex | | 0.309 |
| Male | 28.06 (11.40-105.43) | |
| Female | 24.48 (11.24-78.92) | |
| Age | r = −0.083 | 0.008 |
| Years of education | r = 0.145 | <0.001 |
| BMI | r = −0.077 | 0.017 |

Legend: BMI: Body Mass Index.

A negative correlation was found between age and GDF11 levels, which means that higher the age, lower the GDF11 levels. A negative correlation was also found between BMI and GDF11 levels, meaning that the higher the BMI, lower the GDF11 levels. Finally, a positive correlation was also found between years of education and GDF11 levels, and more years of education is associated with higher levels of GDF11 levels.

Figure 9:
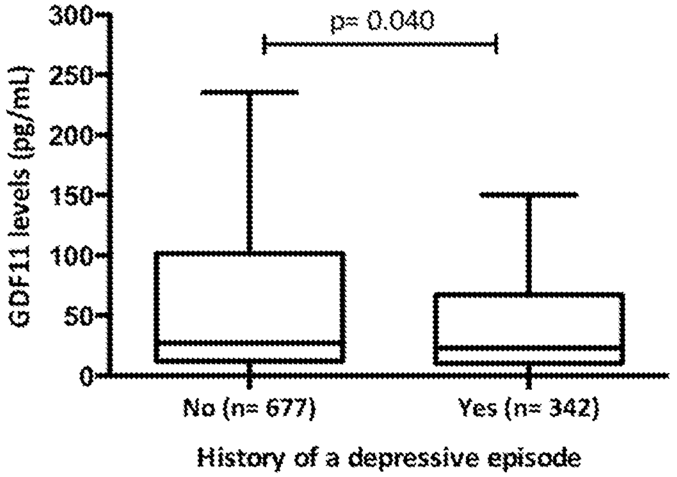
FIG. 9. Serum GDF11 levels and history of depressive episodes on a large cohort. Mann-Whitney U Test for two group comparisons was performed. Data is shown as Tukey boxplots, where the boxes represent the median and interquartile range.

FIG. 9 shows the comparison of serum GDF11 levels between individuals with and without a history of a major depressive episode. Individuals with history of a depressive episode had lower serum GDF11 levels (23.23 [IQR: 10.42-67.10]) than individuals without a history of major depressive episode (27.23 [IQR: 11.75-101.31], p=0.040).

Example 9. Optimization of the Detection Method

An important aspect of the invention of a new diagnostic tool is the development of a better GDF11 protein detection method. In this regard, the inventors have been exploring techniques that could offer a higher detection in serum samples. In this sense, twenty samples of controls individuals were selected from one of our ELISA analyses to be assayed, through a laboratory service in a US company, by an ultrasensitive single molecule array (Simoa) technology that allows detection of proteins and nucleic acids at lowest possible levels. The aim of this preliminary analysis was to compare the sensitivity and the data distribution between the ELISA assay and the Simoa technique, in order to evaluate whether this innovative technology will be a key one to pursue in future analysis.

Methods: Twenty serum samples from healthy individuals were shipped to Myriad RBM company in the US to be assayed by the Simoa technique.

Quantification of GDF11 Serum Levels by Simoa Technique

Method

The assay was processed using Quanterix's fully automated immunoassay platform: Simoa HD-1/HD-X Analyzer and Simoa technology. All incubations took place at room temperature inside the Simoa HD-1/HD-X analyzer. Capture antibody conjugated paramagnetic beads were incubated with standards, samples, controls, and biotinylated detection antibodies. The beads were then washed and incubated with streptavidin-R-galactosidase (SRG). After the final wash, the beads were loaded into the Simoa Disc with SRG, resorufin R-galactopyranoside (RGP). The fluorescence signals were compared to the standard curve and the quantity of target analyte was determined for each sample. The data was interpreted using proprietary software developed by Myriad RBM. For each assay, both calibrators and controls were included on each sample plate. Eight-point calibrators were used to form a standard curve in the first and last column of each plate and controls at 3 concentration levels were run in duplicate. QC for the standard curve, controls, and samples was performed to ensure proper assay performance.

Results

Figure 10:
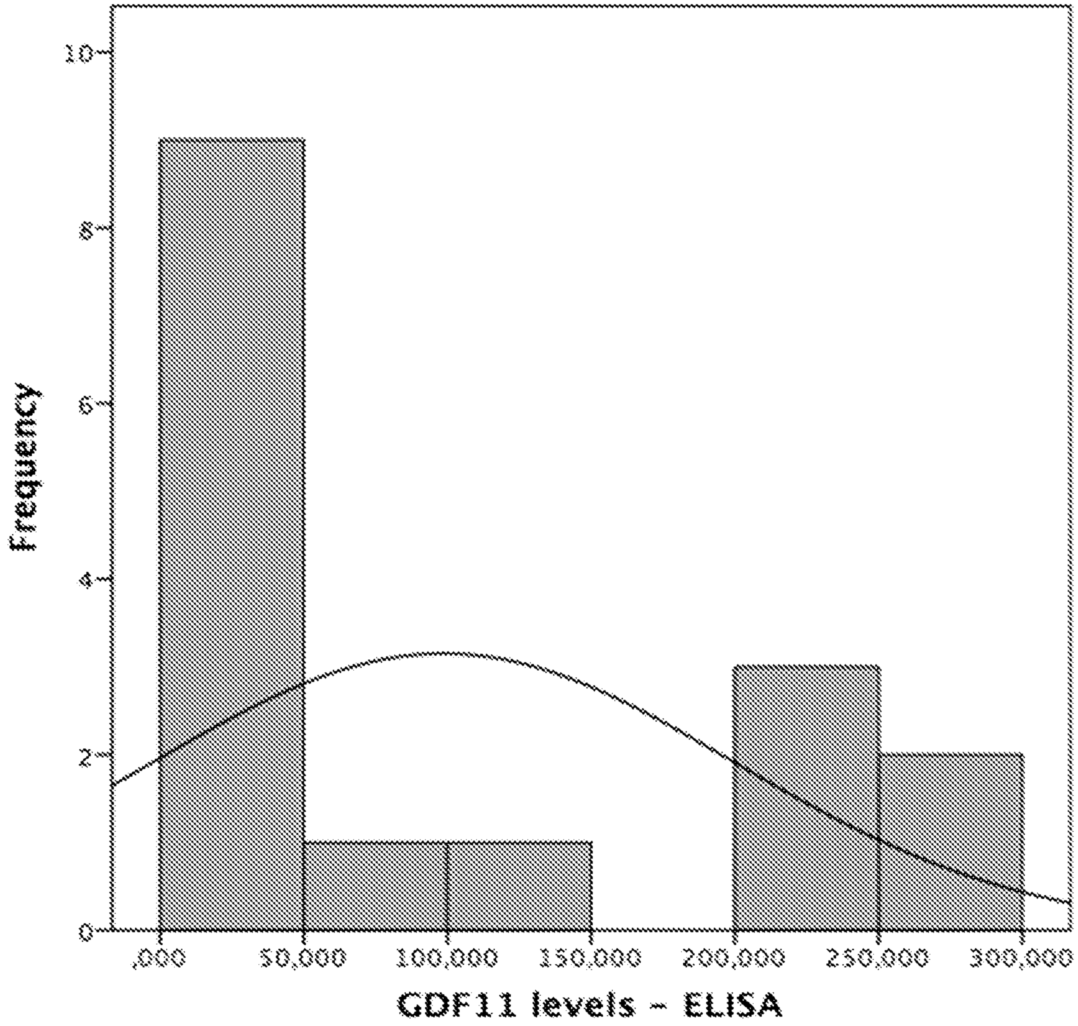
FIG. 10. Data distribution for GDF11 levels according to the technique. Analysis performed in serum from 20 healthy individuals by ELISA assay (A) and Simoa assay (B).

GDF11 was detected in all serum samples by the Simoa assay, while it was detected in only 16 samples in the ELISA experiment. The data distribution for GDF11 levels obtained by the Simoa was better (symmetric distribution in the Gauss curve) as compared to the data distribution (asymmetric) for GDF11 levels in the same samples by ELISA assay (R&D Systems). In addition, the standard deviation was lower as well as the low-high detection range among the samples in the Simoa assay compared to ELISA assay (FIG. 10).

It is also possible to use a camelid heavy-chain antibody (VHH, nanobody) directed against GDF11 in order to enhance the assay detection performance, as this type of antibody is able to cross the blood brain barrier (BBB) (Li T et al. 2016[16]).

Example 10. Efficiency of the Treatment of the Invention

1. Materials and Methods

Animals

Young (3 months) and aged (16 months) C57BL/6JRj mice were obtained from Janvier Labs (France). For the depression-like phenotype induction (CORT), mice were 3 months old and were obtained from Taconic Biosciences (Germany). All animals were group housed and provided free access to water. Mice were occasionally housed individually for the purposes of specific behavioral tests. All animal procedures were performed in accordance with French legislation and in compliance with the European Communities Council Directives (2010/63/UE), according to the regulations of Institut Pasteur Animal Care Committees.

GDF11 Administration in Mice:

GDF11 (Peprotech, Cat #120-11) was dissolved in water, further diluted according to the manufacturer's instructions and injected at a concentration of 1 mg/kg, as previously described in Katsimpardi et al, Aging Cell, 2019[1]. Control mice (young or aged) were injected with equivalent volumes of saline. All mice were injected daily at 4 pm for the duration of the experiment.

CORT-Induced Depression Model:

For the induction of a depression-like phenotype we followed the protocol from David et al[26]. Briefly, 2-month-old mice received corticosterone (CORT) in their drinking water for 6 weeks. CORT was dissolved in 0.45% (2-Hydroxypropyl) beta-Cyclodextrin 10% (β-CD 10%) solution at a final concentration of 35 μg/ml, equivalent to 5 mg/Kg/day. Control mice received equivalent volumes of β-CD 10% without CORT in their drinking water. Daily intraperitoneal GDF11 or vehicle injections started on the 3rd week and lasted for 3 weeks.

Behavioral Tests:

Open Field: Mouse cages were placed in the behavior room for habituation 30 min prior to the test. Four gray arenas (45×45 cm) with high walls were used and luminosity was set at 30 lux throughout the test phases. Each mouse was individually placed in one arena and was left to explore for 10 min. A camera above the arena automatically captured the locomotor activity of each mouse, and its behavioral pattern (distance moved, time spent in the center) was measured and analyzed using EthoVision XT software (Noldus).

Elevated Plus Maze (EPM):

Mouse cages were placed in the behavior room for habituation 1 hour prior to the experiment. The apparatus consists of an elevated cross with two closed arms, two open arms and a center area (intersection between closed and open arms). To measure stress and anxiety, each mouse was placed in the center of the EPM and left to explore the arms for 6 minutes. A camera above the apparatus automatically captured the activity of the mouse and its behavioral pattern, as well as the time spent in the open and closed arms. Measurements and analysis were done using EthoVision XT software (Noldus).

Sucrose Preference Test:

Mice were housed individually one night prior to the experiment. Two bottles containing water were put in each cage in order for the mouse to get familiar with them. The next evening the water in one of the two bottles was replaced with a solution of 2% sucrose. Each bottle was weighed before being placed in the cage. The next morning water and sucrose solution consumption were measured. Bottles were swapped in order to avoid preference. The second morning, water and sucrose solution consumption were measured again. Sucrose preference index was calculated as the total amount of sucrose solution consumed over 2 days divided by the total amount of water+sucrose solution consumed over 2 days.

Nest-Building Behavior.

Mice were housed individually prior to the experiment. Two cotton nestlets were put in each cage. The following morning nest-building capacity was measured by giving a score from 1 to 5 (1=flat nest and some material used, 5=fluffy nest and all material used).

Hanging Wire Test:

Mice were placed on a 20 cm-long wire, 30 cm from the floor. The total amount of time that the mice were able to stay on the wire was measured.

Burrowing Behavior:

Mice were housed individually prior to the experiment. Large burrowing tubes containing approximately 130 g of food pellets were first weighed and then placed in each cage. Mice were left to burrow for 30 min. At the end of the 30 min the burrowing tubes were weighed again to measure the amount of pellets that were dug out. Burrowing behavior was assessed as the percentage of removed pellets relative to initial weight.

Free Dyadic Social Interaction Test:

Mice were habituated in large gray arenas for a week before the beginning of the experiment. The day of the experiment mouse cages were placed in the behavior room for habituation 1 hour prior to the experiment. Four arenas were used at the same time and the experiment was recorded. In each arena one test mouse was placed in the center. Immediately after this, the stimulus mouse (intruder) was also brought in the center of the arena. Mice were left to interact socially for 5 min. Analysis was performed manually by an independent investigator blinded for the experimental conditions. The analysis included measuring the time of facial sniffing and active avoidance as follows. Facial sniffing was measured when there was an oral contact between the test and the stimulus mouse with clear separation of their bodies and mice were <1 cm apart. Active avoidance was measured when the stimulus mouse/intruder moved towards the test mouse and test mouse moved away by >3 cm.

Stimulus mice were purchased and housed separately, were not part of the experimental groups and had never been in contact with the test mice before this experiment.

2. Results

Figure 11:
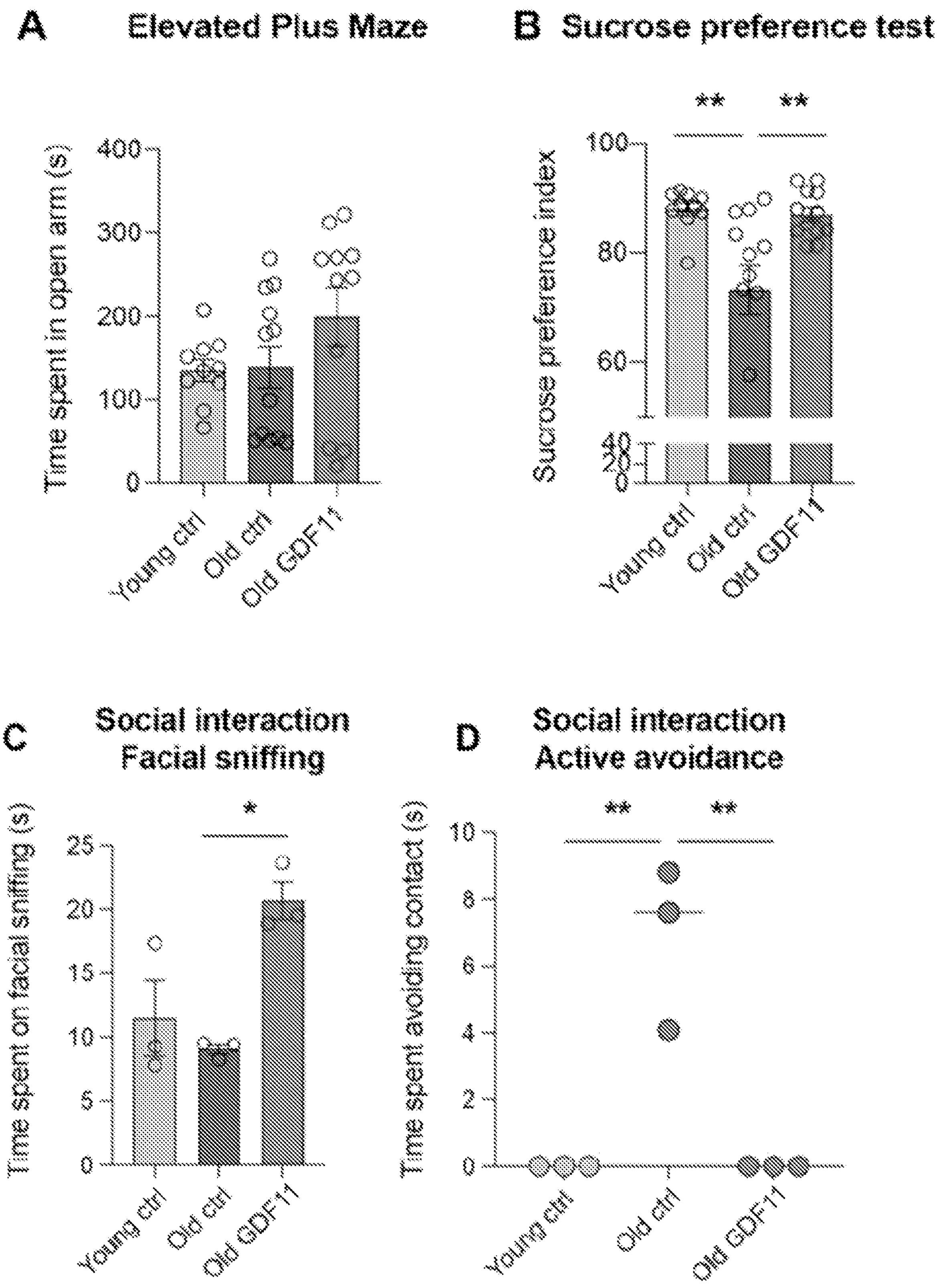
FIG. 11. Systemic GDF11 treatment rescues the depression-like phenotype in aged mice.

Systemic GDF11 Treatment in Aged Mice Rescues the Depression-Like Phenotype (FIG. 11)

In order to further confirm our previous results on the depression-like phenotype, we sought to further investigate mouse behavior after GDF11 treatment by including additional anxiety, depression and anhedonia-related tests. We performed the Elevated Plus Maze (EPM) experiment, where mice were placed on an elevated cross with two open and two closed arms. Based on the innate fear of heights and void that mice exhibit, this test is important to show anxiety levels. We found that, although not statistically significant, more GDF11-treated mice spent time in the open arms of the EPM than old control mice. In fact, it seems that 3 mice were outliers in this experiment, with the other 9 mice spending significantly more time in the open arms (FIG. 11A). These results suggest that there might be a reduction in anxiety with GDF11 treatment, but further analysis, with a higher statistical power, needs to be performed. Next, we measured the preference of mice for sweet with the sucrose preference test, a classical test to assess depressive behavior. This test is based on the premise that depressed mice will not distinguish or will not be interested in sweet taste, as opposed to non-depressed mice which prefer sweet taste. We measured the amount of sweetened water (2% sucrose solution) and normal drinking water that the animals drank over two days. The sucrose preference index was calculated by dividing the amount of sweetened water consumed over the total amount of liquids consumed. Interestingly, we found that both young non-depressed mice, as well as old GDF11-treated mice, exhibited a statistically higher sucrose preference index compared to old control mice (FIG. 11B). These results suggest that GDF11 treatment could attenuate the depression/anhedonia phenotype that comes with aging and confirm our previous results. Next, we sought to evaluate a different type of altered mood behavior, which involves impairments in social function and is linked to schizophrenia, depression and anxiety-related disorders. We used the spontaneous (or free dyadic) social interaction test, which explores the behavior of two mice (test/experimental mouse versus stimulus mouse/intruder) that are unfamiliar which each other and interact in a closed space. This test provides a measure of social interest, since mice with reduced interfacial sniffing and increased active avoidance are considered to be less social (Krauter et al., 2019). Interestingly, we found that GDF11-treated old mice spent significantly more time sniffing the intruder mouse compared to old control mice, showing a higher degree of sociability and reduced anxiety (FIG. 11C). Moreover, GDF11-treated animals never avoided contact with the intruder during the entire length of the experiment, contrary to old control mice (P=0.0025), suggesting a lower level of anxiety, fear and depression (FIG. 11**D).

Next, we sought to determine whether the beneficial effect of GDF11 was restricted specifically to mood changes or whether it could include a broader spectrum of phenotypes. To address this question, we performed additional behavioral tests assessing other characteristics such as strength and general well-being. To measure strength, we performed the hanging wire test, where mice were left to hang from an elevated wire. Because of their fear of the void, mice have the tendency to hold on to the wire for as long as possible. We found that all mice showed the same ability to hang on to the wire, regardless of their age or treatment (FIG. 11E). Furthermore, we performed the nest building test to assess their general well-being. Briefly, mice were housed separately the evening of the test, and new cotton nestlets were placed in each cage. The ability of the mice to construct a well-made or poorly-made nest was measured by a score from 1 to 5 (1: flat nest, material unused, 5: fluffy nest with high walls, all material used). All mice scored highly, with a trend for old control mice to score a bit lower (FIG. 11F). Finally, we performed the burrowing behavior test. Burrowing and digging are natural behaviors for mice and show their general well-being. In this test, mice house individually (after the nest building test) were given large burrowing tubes containing food pellets. We evaluated the burrowing capacity of the mice by measuring the amounts of pellets dug out of the tubes after 30 min. We found no difference in burrowing behavior between mice of all groups, suggesting that general well-being is not affected by GDF11 treatment.

Systemic GDF11 Administration Induces Weight Loss and Attenuates Anxiety in a Mouse Model of Depression (FIG. 12)

In order to further explore the effect of GDF11 as an anti-depressant we set up a model of induced depression. Young mice (8 weeks of age) received corticosterone (CORT, 32 mice/group) or vehicle (Ctrl, 16 mice/group). After 3 weeks of CORT or vehicle (β-CD 10%) administration, these mice were then subjected to intraperitoneal injections of either GDF11 or saline. Consequently, for the following 3 weeks and until the end of the experiment, mice were divided into 4 groups: Ctrl (no CORT, no GDF11; 8 mice), GDF11 (no CORT, GDF11 treatment; 8 mice), CORT (CORT administration, no GDF11; 16 mice), CORT-GDF11 (CORT administration and GDF11 treatment; 16 mice). We assessed the evolution of body weight of these mice during the treatment by weighing them twice a week. As described in our previous work (Katsimpardi et al., Aging Cell, 2020[27]), systemic GDF11 administration induces reduction in body weight after 1 week of treatment in both young and old animals, albeit to a lesser extent in young animals (4% loss of initial weight in young animals versus 8% loss of initial weight in older animals) (FIG. 12A). In this experimental procedure we also found that GDF11 induces weight loss in treated animals. Indeed, young GDF11-treated mice lost a minimal amount of weight as previously described (FIG. 12A). Interestingly, CORT-GDF11 mice lost approximately 10% of body weight compared to their CORT counterparts (FIG. 12B,C). These results show that systemic GDF11 administration induces a strong metabolic effect in mice, and suggest that its mode of action overlaps with—and possibly inhibits—pathways activated by corticosterone.

Furthermore, we performed the open field test, which measures locomotion capacity and symptoms of anxiety. Mice were individually placed in arenas for 10 min and their behavior was analyzed by the Noldus software by tracing the distance moved and the time that mice spent in the center (FIG. 12D). Depressed or anxious mice prefer to avoid the central part of the arena, thereby this measurement gives important information about the mood state of the animal. We found that GDF11 administration induced an attenuation of the anxiety-like behavior, since both control and CORT mice treated systemically with GDF11 spent more time in the center compared to their relative controls (FIG. 12E). In addition, all mice traveled approximately the same total distance (no statistical significance), suggesting that the preference for the central part of the arena was not due to changes in locomotor capacity but rather due to alterations in mood behavior (FIG. 12F).

Taken together, these results demonstrate that systemic administration of GDF11 specifically reduces symptoms of anxiety, anhedonia and depression, further confirming our initial hypothesis and results, and supporting the evidence that GDF11 could be used as a therapeutic agent against mood disorders.

REFERENCES CITED

1. Katsimpardi, L. et al. Systemic GDF11 stimulates the secretion of adiponectin and induces a calorie restriction-like phenotype in aged mice. Aging Cell, e13038, doi: 10.1111/acel.13038 (2019).
2. Katsimpardi, L. et al. Vascular and neurogenic rejuvenation of the aging mouse brain by young systemic factors. Science 344, 630-634, doi:10.1126/science.1251141 science. 1251141 [pii] (2014).
3. Ozek, C., Krolewski, R. C., Buchanan, S. M. & Rubin, L. L. Growth Differentiation Factor 11 treatment leads to neuronal and vascular improvements in the hippocampus of aged mice. Sci Rep 8, 17293, doi:10.1038/s41598-018-35716-6 (2018).
4. Leger, M. et al. Object recognition test in mice. Nat Protoc 8, 2531-2537, doi:10.1038/nprot.2013.155 (2013).
5. Santarelli, L. et al. Requirement of hippocampal neurogenesis for the behavioral effects of antidepressants. Science 301, 805-809, doi:10.1126/science.1083328 (2003).
6. Dong, W. et al. Autophagy involving age-related cognitive behavior and hippocampus injury is modulated by different caloric intake in mice. Int J Clin Exp Med 8, 11843-11853 (2015).
7. Chinta, S. J. et al. Cellular senescence and the aging brain. Exp Gerontol 68, 3-7, doi:10.1016/j.exger.2014.09.018 (2015).
8. Jurk, D. et al. Postmitotic neurons develop a p21-dependent senescence-like phenotype driven by a DNA damage response. Aging Cell 11, 996-1004, doi:10.1111/j.1474-9726.2012.00870.x (2012).
9. Krishnamurthy, J. et al. Ink4a/Arf expression is a biomarker of aging. J Clin Invest 114, 1299-1307, doi: 10.1172/JCI22475 (2004).
12. Chesney, E., Goodwin, G. M., & Fazel, S. (2014). Risks of all-cause and suicide mortality in mental disorders: A meta-review. World Psychiatry, 13(2), 153-160. doi: 10.1002/wps.20128
13. Du L, Miao Y, Li X, Shi P, Hu Z. A Novel and Convenient Method for the Preparation and Activation of PRP without Any Additives: Temperature Controlled PRP. Biomed Res Int. 2018 May 13; 2018:1761865.
14. Fries G R, Zamzow M J, Andrews T, Pink O, Scaini G, Quevedo J. Accelerated aging in bipolar disorder: A comprehensive review of molecular findings and their clinical implications. Neurosci Biobehav Rev. 2020 May; 112:107-116. doi: 10.1016/j.neubiorev.2020.01.035. Epub 2020 Feb. 1. PMID: 32018037.
15. Katsimpardi L, Rubin L L. Young systemic factors as a medicine for age-related neurodegenerative diseases. Neurogenesis (Austin). 2015 Feb. 3; 2(1):e1004971. doi: 10.1080/23262133.2015.1004971. PMID: 27502604; PMCID: PMC4973601.
16. Li T, Vandesquille M, Koukouli F, Dudeffant C, Youssef I, Lenormand P, Ganneau C, Maskos U, Czech C, Grueninger F, Duyckaerts C, Dhenain M, Bay S, Delatour B, Lafaye P. Camelid single-domain antibodies: A versatile tool for in vivo imaging of extracellular and intracellular brain targets. J Control Release. 2016 Dec. 10; 243:1-10. doi: 10.1016/j.jconrel.2016.09.019. Epub 2016 Oct. 6. PMID: 27671875.
17. López-Villarreal A, Sánchez-Morla E M, Jiménez-López E, Martinez-Vizcaíno V, Aparicio A I, Mateo-Sotos J, Rodriguez-Jimenez R, Vieta E, Santos J L. Progression of the functional deficit in a group of patients with bipolar disorder: a cluster analysis based on longitudinal data. Eur Arch Psychiatry Clin Neurosci. 2019 Aug. 17.
18. Ritchie, H., & Roser, M. (2018, January 20). Mental health. Retrieved May 6, 2021, from https://ourworldindata.org/mental-health
19. Squassina A, Pisanu C, Vanni R. Mood Disorders, Accelerated Aging, and Inflammation: Is the Link Hidden in Telomeres? Cells. 2019 Jan. 15; 8(1):52. doi: 10.3390/cells8010052. PMID: 30650526; PMCID: PMC6356466.
20. Walker, E. R., McGee, R. E., & Druss, B. G. (2015). Mortality in mental disorders and global disease burden implications. JAMA Psychiatry, 72(4), 334. doi:10.1001/jamapsychiatry.2014.2502.
21. Alting-Mees et al., "Monoclonal Antibody Expression Libraries: A Rapid Alternative to Hybridomas", Strategies in Molecular Biology 3:1-9 (1990)
22. Souza T. A. et al., Proteomic identification and functional validation of activins and bone morphogenetic protein 11 as candidate novel muscle mass regulators. Molecular Endocrinology 2008 22:2689-2702.
23. Holliger & Hudson, 2006, Nature Biotechnology 23(9): 1 126-1 136
24. Carter 2006, Nature Reviews Immunology 6:343-357
25. Moreira F P et al., Biological rhythms, metabolic syndrome and current depressive episode in a community sample. Psychoneuroendocrinology, 2016 October; 72:34-9.
26. David D J et al, Neurogenesis-dependent and -independent effects of fluoxetine in an animal model of anxiety/depression. Neuron, 2009 (PMID 19477151)
27. Katsimpardi L. et al., Systemic GDF11 stimulates the secretion of adiponectin and induces a calorie restriction-like phenotype in aged mice. Aging Cell. 2020 January; 19(1):e13038

The invention claimed is:

1. A method for treating or preventing a mood and/or anxiety disorder in a subject in need thereof, said method comprising administering to said subject an agent or a composition which increases the levels of the GDF11 polypeptide, wherein the agent or composition comprises an agonist antibody that increases levels of GDF11, a GDF11 polypeptide, homodimers of GDF11 polypeptides, complexes of GDF11 polypeptides or a nucleic acid encoding a GDF11 polypeptide or a functional fragment or variant thereof, wherein said GDF11 polypeptide comprises or consists of the amino acid sequence of SEQ ID NO:1, SEQ ID NO: 2, or SEQ ID NO:3.

2. The method according to claim 1, wherein the disorder is a mood disorder.

3. The method according to claim 1, wherein the GDF11 polypeptide which is administered is a modified GDF11 polypeptide.

4. The method according to claim 3, wherein the modified GDF11 polypeptide comprises a modification selected from the group consisting of fusion to an Fc fragment, pegylation, conjugation to albumin, an amino acid mutation that prevents or reduces proteolytic degradation, an amino acid mutation that prolongs half-life, and any combination thereof.

5. The method according to claim 1, wherein the subject does not suffer from a neurodegenerative disorder.

6. The method according to claim 1, wherein the disorder is major depressive disorder.

7. An in vitro method of screening a compound, comprising:

a) administering a test compound to a subject having a mood and/or anxiety disorder;

b) obtaining a sample from the subject;

c) contacting the sample with a GDF11-binding molecule; and d) detecting bound GDF11, and measuring the levels of GDF11 in the subject sample, and wherein if the levels of GDF11 in the sample are significantly lower than healthy reference levels, then the test compound is not identified as having a mood disorder treating activity or wherein if the levels of GDF11 in the sample are not significantly lower than healthy reference levels, then the test compound is identified as having a mood disorder treating activity.

8. The in vitro method of claim 7, wherein the disorder is a mood disorder.

9. The in vitro method of claim 7, wherein the subject is a less than 65 years old human.

10. The in vitro method of claim 7, wherein the disorder is major depressive disorder.

* * * * *